(12) United States Patent
Van Der Burg et al.

(10) Patent No.: US 10,253,073 B2
(45) Date of Patent: Apr. 9, 2019

(54) LONG PEPTIDES OF 22-45 AMINO ACID RESIDUES THAT INDUCE AND/OR ENHANCE ANTIGEN SPECIFIC IMMUNE RESPONSES

(71) Applicant: Academisch Ziekenhuis Leiden, Leiden (NL)

(72) Inventors: Sjoerd Hendrikus Van Der Burg, Waddinxveen (NL); Tom H. M. Ottenhoff, Oegstgeest (NL); Annemieke Geluk, Woubrugge (NL); Maria Johanna Philomena Schoenmaekers-Welters, Leiden (NL); Annemieke M. De Jong, Amsterdam (NL); Rienk Offringa, Leiden (NL); Cornelis Johannes Maria Melief, Haarlem (NL); Reinaldus Everardus Maria Toes, Leiden (NL)

(73) Assignee: Academisch Ziekenhuis Leiden, Leiden (NL)

( * ) Notice: Subject to any disclaimer, the term of this patent is extended or adjusted under 35 U.S.C. 154(b) by 0 days.

(21) Appl. No.: 15/581,035

(22) Filed: Apr. 28, 2017

(65) Prior Publication Data
US 2017/0320915 A1 Nov. 9, 2017

Related U.S. Application Data

(60) Continuation of application No. 14/832,060, filed on Aug. 21, 2015, now Pat. No. 9,650,423, which is a continuation of application No. 11/712,199, filed on Feb. 28, 2007, now Pat. No. 9,115,185, which is a division of application No. 10/433,936, filed as application No. PCT/NL01/00893 on Dec. 7, 2001, now Pat. No. 7,202,034.

(30) Foreign Application Priority Data

Dec. 8, 2000 (EP) .................................. 00204398
Aug. 31, 2001 (EP) .................................. 01203298

(51) Int. Cl.

| | | |
|---|---|---|
| *C07K 14/025* | (2006.01) | |
| *A61K 39/12* | (2006.01) | |
| *C07K 14/005* | (2006.01) | |
| *C12N 7/00* | (2006.01) | |
| *A61K 39/00* | (2006.01) | |
| *A61K 39/04* | (2006.01) | |
| *A61K 39/39* | (2006.01) | |
| *A61K 38/00* | (2006.01) | |

(52) U.S. Cl.
CPC ........ *C07K 14/005* (2013.01); *A61K 39/0011* (2013.01); *A61K 39/04* (2013.01); *A61K 39/12* (2013.01); *A61K 39/39* (2013.01); *C12N 7/00* (2013.01); *A61K 38/00* (2013.01); *A61K 39/00* (2013.01); *A61K 2039/515* (2013.01); *A61K 2039/525* (2013.01); *A61K 2039/55516* (2013.01); *A61K 2039/55522* (2013.01); *A61K 2039/55555* (2013.01); *A61K 2039/55561* (2013.01); *A61K 2039/55566* (2013.01); *A61K 2039/55572* (2013.01); *A61K 2039/57* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| 5,601,973 A | 2/1997 | Muller et al. |
|---|---|---|
| 6,183,745 B1 | 2/2001 | Tindle et al. |
| 6,306,397 B1 | 10/2001 | Edwards et al. |

(Continued)

FOREIGN PATENT DOCUMENTS

| EP | 0 344 940 | 12/1989 |
|---|---|---|
| EP | 0 451 550 | 10/1991 |

(Continued)

OTHER PUBLICATIONS

Azoury-Ziadeh et al., "T-Helper Epitopes Identified Within the E6 Transforming Protein of Cervical Cancer-Associated Human Papillomavirus Type 16", Viral Immunology, 1999, pp. 297-312, vol. 12. No. 4, Australia.
Bijker, M.S., et al., Eur. J. Immunol, 2008, vol. 38, pp. 1033-1042.
Bijker, M.S., et al., Journal of Immunology, 2007, vol. 179, pp. 5033-5040.
Bontkes, Hetty J. et al "Human papillomavirus type 16 E6/E7-specific cytotoxic T lymphocytes in women with cervical neoplasia" International Journal of Cancer, 88( 1):92-98, Oct. 1, 2000.

(Continued)

*Primary Examiner* — Nianxiang Zou
(74) *Attorney, Agent, or Firm* — Gilberto M. Villacorta; Sunit Talapatra; Foley & Lardner LLP

(57) ABSTRACT

Epitopes derived from human papilloma virus and peptides having a size of about 22-45 amino acid residues comprising minimal T cell epitopes are disclosed. Also disclosed are clinically relevant approaches for immunizing subjects against (Myco) bacterially and/or virally infected cells or tumor cells. Peptide sequences of 22-35 amino acid residues in length can induce both peptide-specific CD8+ cytolytic cells and CD4+ T-helper cells. Moreover, vaccination with 22-35 residue long peptides results in a more vigorous CD8+ cytolytic T-cell response than vaccination with peptides of the exact minimal CTL epitope length. The intrinsic capacity of certain minimal CTL epitopes which instead of activating cytolytic effector cells tolerize these cytolytic cells, can be overcome by use of these 22-35 amino acid long peptides. Also disclosed are clinically relevant approaches for vaccination and/or treatment of subjects against HPV and methods and uses suited to treat subjects suffering from progressive lesions and/or cervical cancer.

9 Claims, 20 Drawing Sheets

Specification includes a Sequence Listing.

(56) References Cited

U.S. PATENT DOCUMENTS 6,582,704 B2 6/2003 Urban et al.
6,783,763 B1 8/2004 Choppin et al.

FOREIGN PATENT DOCUMENTS

| JP | 02-096593 | 4/1990 |
|---|---|---|
| JP | 06-501542 | 2/1994 |
| JP | 06-503559 | 4/1994 |
| WO | WO-91/18294 | 11/1991 |
| WO | WO-92/10513 | 6/1992 |
| WO | WO-99/48917 | 9/1999 |
| WO | WO-00/75336 | 12/2000 |

OTHER PUBLICATIONS

Bourgault Villada, Isabelle et al. "Identification in humans of HPV-16 E6 and E7 protein epitopes recognized by cytolytic T lymphocytes in association with HLA-818 and determination of the HLA-818-specific binding motif." Europ Journal Immunol., 30(8):2281-2289, Aug. 2000.

Cao et al., "Successful adjuvant-free vaccination of BALB/c mice with mutated amyloid beta peptides", BMC Neuroscience, 2008, vol. 9, No. 25. pp. 1-11.

Chu et al., Clinical and Experimental Immunology, Aug. 2000, vol. 121, pp. 216-225.

Comerford, et al. "Identification of T- and B-cell epitopes of the E7 protein of human papillomavirus type 16" J. Virol (Sep. 1991) vol. 65, No. 9, pp. 4681-4690.

Extended European Search Report under Rule 62 EPC and Opinion (dated Sep. 24, 2009).

Feltkamp et al., Cytotoxic T Lympholytes Raised Against a Sub Dominant Epitope Offered as a Synthetic Peptide Eradicate Human Papillomavirus Type 16-Induced Tumors, European Journal of Immunology, vol. 25, No. 9, pp. 638-2642 (1955).

Feltkamp, et al. "Vaccination with cytotoxic T lymphotcyte epitope-containing peptide protects against a tumor induced by human papillomavirus type 16-transformed cells", Eur. J. Immunol. (1993), vol. 23, pp. 2242-2249.

GenBank: AHK23256.1. E6 [Human papillomavirus type 16], 158 aa, Mar. 3, 2014.

GenBank: AKN79013.1. E6 [Human papillomavirus type 16], 151 aa, Jul. 4, 2015.

Hariharan, et al. "Tumor regression in mice following vaccination with human papillomavirus E7 recombinant protein in PROVAX", International Journal of Oncology (1998), vol. 12, pp. 1229-1235.

Kadish et al., "Lymphoproliferative responses to Human Papillomavirus (HPV) type 16 proteins E6 and E7: Outcome of HPV infection and associated neoplasia", J Natl Cancer Inst, 1997, vol. 89, pp. 1285-1293.

Kast et al., "Role of HLA—A Motifs in Identification of Potential CTL Epitopes in Human Papillomavirus Type E6 and E7 Proteins", Journal of Immunology, 1994, pp. 3904-3912.

Lehtinen M et al. "Human T helper cell epitopes overlap B cell and putative cytotoxic T cell epitopes in the E2 protein of human papillomavirus type 16". Biochem Biophys Res Commun. Apr. 17, 1995;209 (2):541-6.

Londono LP et al. Immunisation of mice using *Salmonella typhimurium* expressing human papillomavirus type 16 E7 epitopes inserted into hepatitis B virus core antigen. Vaccine. Apr. 1996, 14(6):545-52.

Ossendorp et al., "Specific T Helper Cell Requirement for Optimal Induction of Cytotoxic T Lymphocytes against Major Histocompatibility Complex Class II Negative Tumors", J. Exp. Med., Mar. 2, 1998, pp. 693-702, vol. 187,No. 5, The Rockefeller University Press.

Ressing et al., "Human CTL Epitopes Encoded by Human Papillomavirus Type 16 E6 and E7 Identified Through In Vivo and In Vitro Immunogenicity Studies of HLA-A*0201-Binding Peptides", Journal of Immunology, 1995, pp. 5934-5942.

Ressing et al., Journal of Immunology, Mar. 2000, vol. 23, No. 2, pp. 255-266.

Selvakumar R et al. Immunization with nonstructural proteins El and E2 of cottontail rabbit papillomavirus stimulates regression of virus-induced papillomas. J Virol. Jan. 1995; 69(1 ): 602-605.

Shirai et al., "Helper-Cytotoxic T Lymphocyte (CTL) Determinant Linkage Required for Priming of Anti-HIV COB CTL in Vivo with Peptide Vaccine Constructs", Journal of Immunology, 1993, pp. 549-556.

Tillman BW et al. Adenoviral vectors targeted to CD40 enhance the efficacy of dendritic cell-based vaccination against human papillomavirus 16-induced tumor cells in a murine model. Cancer Res. Oct. 1, 2000;60(19):5456-63.

Tindle et al., "A 'public' T-helper epitope of the E7 transforming protein of human papillomarvirus 16 provides cognate help for several E7 B-cell epitopes from cervical cancer-associated human papillomavirus genotypes", Proc. Natl. Acad. Sci. USA, Jul. 1991, pp. 5887-5891, vol. 88.

Todd et al., "Human papillomavirus (HPV) type 16-specific CD8 T cell responses in women with high grade vulvar intraepithelial neoplasia", Int. J Cancer, Mar. 2004, vol. 108, No. 6, pp. 857-862.

Toes et al., "Enhanced Tumor Outgrowth after Peptide Vaccination", Journal of Immunology, 1996, pp. 3911-3918.

Toes et al., "Peptide vaccination can lead to enhanced tumor growth through specific T-cell tolerance induction", Proc. Natl. Acad. Sci. USA, Jul. 1996, pp. 7855-7860, vol. 93.

Toes, REM et al., Enhancement of Tumor Outgrowth Through CTL Tolerization After Peptide Vaccination is Avoided by Peptide Presentation on Dendritic Cells, J, Immunology, 16: 4449-445(1998).

Tsukui, Taka et al. Interleukin 2 production in vitro by peripheral lymphocytes in response to human papillomavirus-derived peptides: Correlation with cervical pathology Cancer Research, 56(17):3967-3974, 1996.

Van Den Hende et al., "Skin reactions to human papillomavirus (HPV) 16 specific antigens intradermally injected in healthy subjects and patients with cervical neoplasia", Int. J Cancer, Jul. 2008, vol. 123, No. 1, pp. 146-152.

Van Der Burg, Sjoerd H et al. "Natural T-Helper Immunity against human papillomavirus type 16(HPV16) E7-derived peptide epitopes in patients with HPV16-positive cervical lesions: identification of 3 human leukocyte antigen class II-restricted epitopes" Int. J. Cancer: 91, 612-618 (2001).

Weiner et al., "Immunostimulatory oligodeoxynucleotides containing the CpG motif are effective as immune adjuvants in tumor antigen immunization", Proc. Natl. Acad. Sci. USA, Sep. 1997, pp. 10833-10837, vol. 94.

Whitton et al. DNA immunization: mechanistic studies. Vaccine. Mar. 26, 1999;17(13-14):1612-9.

Yi-Qun et al., "Differential requirements for co-stimulatory signals from B7 family members by resting versus recently activated memory T cells towards soluble recall antigens", International Immunology, 1995, pp. 37-44, vol. 8, No. 1.

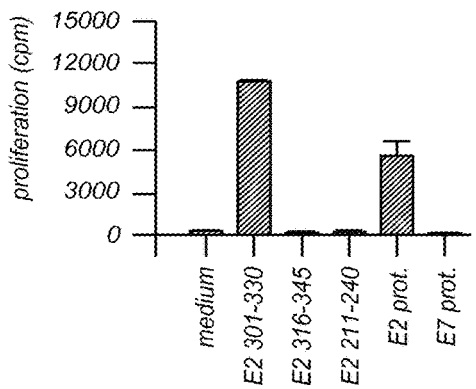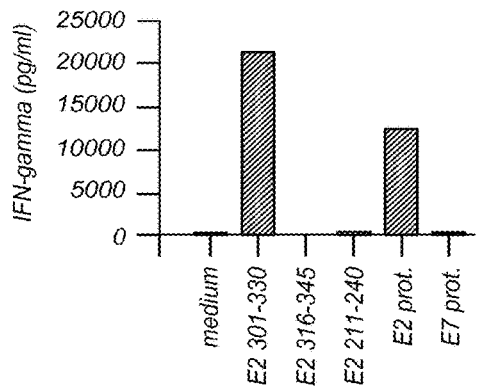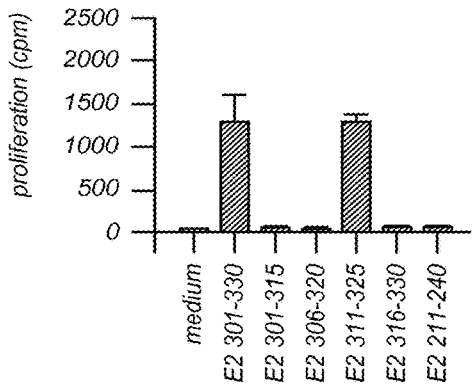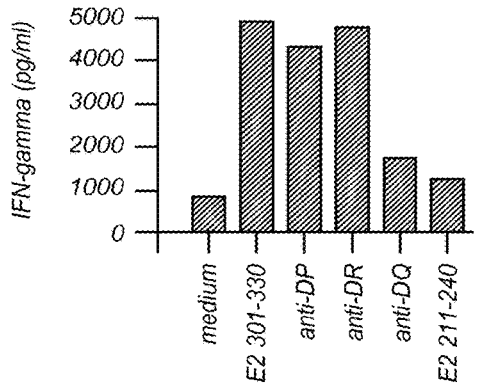

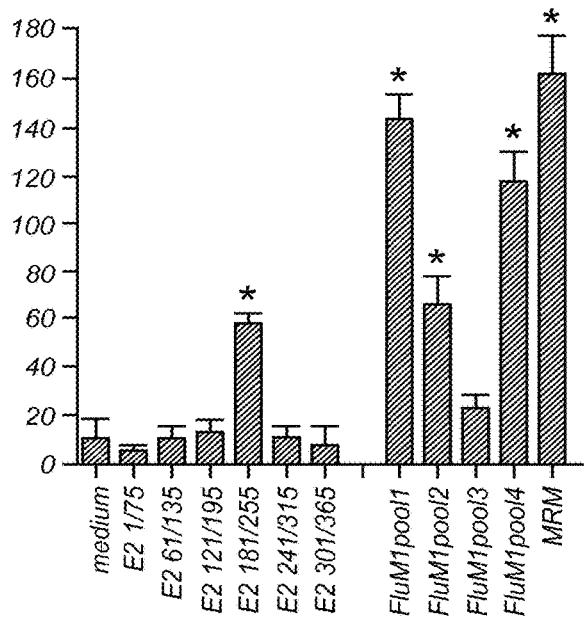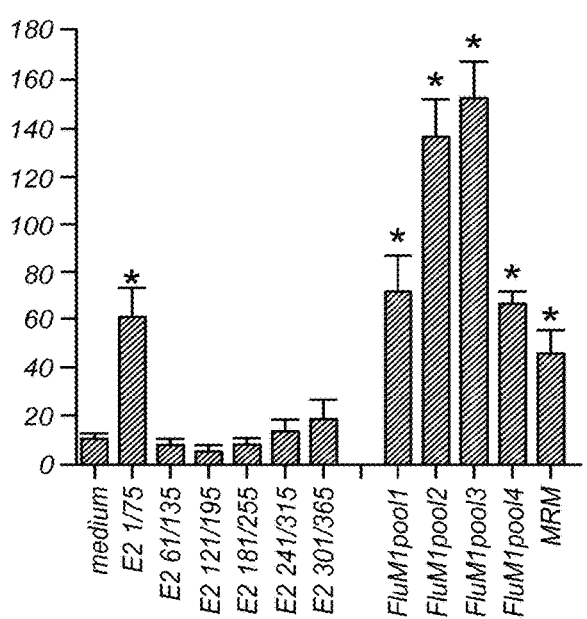

LONG PEPTIDES OF 22-45 AMINO ACID RESIDUES THAT INDUCE AND/OR ENHANCE ANTIGEN SPECIFIC IMMUNE RESPONSES

CROSS-REFERENCE TO RELATED APPLICATIONS

This application is a Continuation of U.S. patent application Ser. No. 14/832,060, filed Aug. 21, 2015, which is a Continuation of U.S. patent application Ser. No. 11/712,199, filed Feb. 28, 2007, now U.S. Pat. No. 9,115,185, which is a Division of U.S. patent application Ser. No. 10/433,936, filed Nov. 12, 2003, now U.S. Pat. No. 7,202,034, which is the U.S. National Stage Application of PCT/NL2001/00893, filed Dec. 7, 2001, which claims the benefit of European Patent Application No. 00204398.2, filed Dec. 8, 2000, and European Patent Application No. 01203298.3, filed Aug. 31, 2001, all of which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Apr. 12, 2017, is named sequence.txt and is 8 KB in size.

TECHNICAL FIELD

The present invention relates generally to the field of medicine, and more specifically to induction and/or enhancement of a T cell response directed towards an antigen, using peptides comprising specific epitopes for said antigen.

The invention is exemplified mainly by using HPV directed immunity as a model. However, the invention should not be read as being limited to HPV but rather as being relevant for a wide variety of immune related or relatable diseases.

BACKGROUND OF THE INVENTION

HPV infection is highly prevalent among young, sexually active male and female individuals. Large prospective studies showed that acquisition of HPV from male partners is common, occurring in 40-60% of subjects during a 3 year follow-up period (Koutsky et al., 1997, Ho et al., 1998, Marrazzo et al., 2000). Therefore, HPV is probably the most common sexually transmitted disease.

Papillomaviruses of the high-risk types (e. g. HPV16,18, 31,33, and 45) are responsible for cervical cancer (Bosch et al., 1995, Zur Hausen, 1996). Following infection of the basal epithelial cells, the immediate HPV early genes E1, E2, E5, E6 and E7 are expressed. The E1 and E2 genes regulate viral replication. Furthermore, the E2 protein controls the expression of the E6 and E7 oncoproteins. The E6 protein of the high-risk HPV types specifically binds to p53 and targets its rapid degradation through the ubiquitin pathway. P53 is involved in initiation of apoptosis and loss of this protein result in the prevention of apoptosis (Scheffner et al., 1990). The E7 protein of high-risk types binds to pRB, which normally prevents cells from entering the cell cycle by inactivating E2F, a protein needed for cell cycle entry (Dyson et al. 1989). E7 expression results in the failure of infected cells to withdraw from the cell cycle and differentiate. Prolonged and elevated expression of the E6 and E7 oncoproteins is tightly associated with HPV-induced dysplasia and transformation into cervical carcinoma.

The protective role of the immune system in the defence against HPV-related diseases and HPV-induced cancer in humans is suggested by the fact that compared to normal controls, immunosuppressed renal transplant patients and patients infected with HIV display a 17-fold greater incidence of genital HPV infection (Ho et al., 1994, Matorras et al. 1991, Halpert et al. 1986). The diminished capacity of immunosuppressed individuals to resolve HPV infection indirectly points towards a protective role of the immune system early in infection. Evidence of protection against HPV via immunity against the early antigens E2, E6 and E7 comes from the cottontail rabbit papillomavirus model which is the major animal model for cancer-associated papillomaviruses. Vaccination with the nonstructural proteins E1 and E2 induces the regression of virus-induced papillomas whereas viral tumor growth is suppressed. Furthermore, rabbits vaccinated with the combination of the E1, E2, E6, and E7 genes were completely protected against viral challenge (Han et al. 1999, Selvakumar et al.1995). These data indicate that immunity against E2, E6, and E7 can be effective as immunoprophylaxis of papillomavirus infection as well as therapeutically for HPVinduced lesions and cancer.

Considerable interest exists in the identification of epitopes involved in the immune response to HPV16, given the possibility to incorporate these as subunits into a vaccine or to use these epitopes to monitor vaccine induced immunity in vivo. Since most epithelial cells express MHC class I but not class II, the attention has so far been focused on the induction of tumoricidal HPV-specific CD8+ cytotoxic T lymphocytes (Melief et al., 2000; Ressing et al., 1995; Ressing et al., 2000; Ressing et al., 1996). HPVspecific CD8+ T-cell reactivity has been found in the peripheral blood of patients diagnosed with cervical intraepithelial neoplasia grade III (CIN III) lesions or cervical carcinoma (Nimako et al., 1997; Ressing et al., 1996) and in tumor-infiltrating T-cell populations isolated from patients with cervical cancer (Evans et al., 1997). Tumorspecific CD4+ T helper ("Th") immunity is now also considered pivotal for the efficient eradication of solid tumors, despite the fact that most of these tumors do not express MHC class II (reviewed in Melief et al., 2000; Pardoll and Topalian, 1998; Toes et al., 1999). Recent evidence indicates that CD4+ tumor specific T-cells are required not only for optimal induction of CD8+ tumor specific CTL but also for optimal exertion of local effector cell function by these CTL (Ossendorp et al., 1998, Toes et al., 1999). For induction of MHC class I restricted tumor-specific immunity, cross-presentation of antigens that have been captured by professional antigen presenting cells appears to play a dominant role. For proper induction of tumor-specific CTL by cross-priming tumor-specific CD4+ T cell help is required (Toes et al., 1999, Schoenberger et al., 1998).

A positive role for HPV-specific Th-immunity was suggested by the predomination of CD4+ T-cells in regressing genital warts (Coleman et al., 1994) as well as by the detection of delayed-type hypersensitivity responses to HPV16 E7 in the majority of subjects with spontaneous regressing CIN lesions (Hopfl et al., 2000). Furthermore, HPV16-specific CD4+ T-cells have been detected in the blood of patients with persistent HPV infections, high-grade CIN lesions or cervical cancer (de Gruijl et al., 1998). For the less prevalent oncogenic types HPV59 and HPV68, HLA-DR4 restricted Th-cells were isolated from the T-cells that infiltrated a cervical cancer lesion (Hohn et al., 1999). In contrast, despite the presence of HPV16 in the majority of progressive CIN lesions and cervical cancers, no in depth information is available concerning HLArestriction and epitope specificity of HPV16-specific T-helper responses. For a clinically relevant approach of immunizing subjects, for instance against (Myco) bacterially and/or virally infected cells or tumor cells, and HPV in particular, it is preferred that both specific T-helper cells and CTL are induced. We have already shown that immunization with minimal CTL epitopes results in protection against tumors in some models (Feltkamp et al. 1993, Kast et al. 1991) whereas, in other models, it can lead to tolerance or functional deletion of virus-and tumor-specific CTL that when otherwise induced are protective (Toes et al. 1996ab). The occurrence of tolerance or functional deletion decreases the effects of vaccination significantly. However, until the present invention there was no solution for this phenomenon. Epitopes involved with this effect were therefore not suitable for immunization purposes. Processing of exogenous antigens for presentation by MHC class I molecules by cross-priming as well as by other mechanisms is now widely recognized second pathway of processing for presentation by MHC class I, next to the well known endogenous route (Jondal et al. 1996, Reimann et al. 1997). The normal outcome of antigen processing via this pathway is CTL tolerance, unless APC activation by CD4+ T-cells takes place (Kurts et al., 1997).

Furthermore, in several studies with murine virus infections, a positive correlation was detected between the frequency of CTL precursors and protective immunity (Sedlik et al. 2000, Fu et al., 1999). For an optimal induction of CTL, presentation of CTL epitopes preferably takes place at the surface of professional antigen presenting cells (APC's) such as dendritic cells (Mellman e al. 1998, Rodriguez et al. 1999). Whereas minimal CTL-and Th-epitopes can, without the need of processing by professional antigen presenting cells, be presented to T-cells, proteins need to be taken up and processed for an optimal presentation of CTL and Th-epitopes in MHC class I and MHC class II, respectively, can occur (Manca et al. 1994).

SUMMARY OF THE INVENTION

The present invention is concerned with means and methods for improving antigen specific immune responses. To this end the invention provides a method for inducing and/or enhancing an antigen specific T cell response comprising providing a system capable of exhibiting said response with a peptide comprising a T cell epitope specific for said antigen, said peptide comprising 22-45 amino-acid residues. These peptides can be synthesized efficiently whereas they also allow efficient uptake by cells capable of processing said peptide and present processed epitopes in the context of MHC-1 or MHC-II. Preferably, said peptide is processed by a professional antigen presenting cell.

Antigen presenting cells and particularly professional antigen presenting cells such as dendritic cells are very efficient in processing and presenting epitopes, whereas they further comprise additional functionalities allowing efficient communication with T-cells which ultimately leads to improved induction and/or enhancement of said antigen specific T cell response. Thus in a preferred embodiment a method of the invention is provided wherein said peptide comprises a sequence capable of activating an antigen presenting cell. By a sequence capable of activating an antigen presenting cell is meant a sequence which is capable of at least partly activating an antigen presenting cell, preferably a professional antigen presenting cell. Said activation preferably leads to presentation of at least one epitope of said peptide at the surface of said APC. In a particularly preferred embodiment said peptide comprises at least two T cell epitopes for said antigen. The presence of two T cell epitopes for said antigen allows an even more efficient induction and/or enhancement of said antigen specific T cell response.

Preferably, at least one of said epitopes comprises a T-helper cell epitope for said antigen or a cytotoxic T lymphocyte (CTL) epitope for said antigen. Having at least one or the other epitope present on the peptide is favorable. Efficient induction and/or enhancement is achieved when said peptide comprises a T-helper activating sequence. By a T-helper activating sequence is meant herein a sequence capable of at least partly activating a T-helper cell. Said activation preferably leads to improved induction and/or enhancement of said antigen specific T cell response. In one embodiment said peptide comprises at least one T-helper cell epitope for said antigen and at least one cytotoxic T lymphocyte (CTL) epitope for said antigen. Surprisingly, it was found that with such peptides the problem of induction of (partial) tolerance against epitopes on said peptide does not, or to a lesser extent, occur whereas induction and/or enhancement of a specific T cell response for said antigen is very efficient. Thus in a particularly preferred embodiment of the invention said peptide comprises at least one T-helper cell epitope for said antigen and at least one cytotoxic T lymphocyte (CTL) epitope for said antigen.

An epitope for an antigen is capable of interacting with a T-cell receptor specific for said antigen, said T-cell receptor being specific for an MHC-I or MHC-II molecule presenting an antigen derived or derivable peptide comprising said epitope. Though said T-cell receptor must be capable of interacting with a peptide derived or derivable from said antigen, said epitope can be present on a wide variety of different compounds. Generally an epitope for antigen is present on an immunogenic part of said antigen, said part being at least 9 amino-acids long and capable of being presented by an MHC-I or MHC II molecule. With the current technology, however, it is possible to provide epitopes that are generated in an entirely different way or comprising different matter. For instance, once a fragment of said antigen is known to comprise an epitope, peptides can be generated that are different in one or more amino-acid positions. Subsequently the presence or absence of said epitope can easily be verified by, for instance, an ELISPOT assay using a T cell specific for said epitope. Epitopes for an antigen can be present on a variety of different molecules such as but not limited to peptides, modified peptides, peptidomimetics.

A peptide of the invention may comprise an epitope for any particular antigen. However, preferably said antigen comprises a (Myco) bacterial and/or viral protein or an immunogenic part, derivative and/or analogue thereof. In one aspect of the invention, said antigen comprises a *Mycobacterium* protein or an immunogenic part, derivative and/or analogue thereof. In a preferred embodiment of the invention said antigen comprises hsp65 369-412 (Ottenhof et al., 1991; Charo et al., 2001). Hsp65 369-412 comprises an HLA-A*0201 epitope at position 369-377, recognized by cytotoxic T-cells, and a DR3 epitope at position 390-412, recognized by T-helper cells. In another preferred embodiment, said antigen comprises a human papillomavirus (HPV) protein or an immunogenic part, derivative and/or analogue thereof. An immunogenic part, derivative and/or analogue of a protein comprises the same immunogenic capacity in kind not necessarily in amount as said protein itself. A derivative of such a protein can be obtained by preferably conservative amino acid substitution.

More preferably, said protein comprises E2, E6 and/or E7. Regions were identified in the E2, E6 and E7 sequence that were most immunogenic. Furthermore, a number of naturally processed Th-epitopes mapping in this region were identified. Methods included respectively short and long-term PBMC cultures derived from healthy blood donors. The PBMC cultures were stimulated with peptides of 22-35 amino acid residues in length. In parallel, the in vivo induced E2, E6 and E7-specific immunity, as detected by IFNγ ELISPOT assays, was analysed in healthy subjects as well as subjects diagnosed with HPV16+ lesions.

Pathogen and tumor-specific T helper immunity was found to play a pivotal role in the natural and vaccine-induced immune defence against viral infections and tumors. The Th response against the human papilloma virus type 16 (HPV16) E2, E6 and E7 proteins was investigated in detail. By means of short and long term PBMC cultures from HLA-typed healthy donors, we identified three separate regions in the E2 protein (E2 31-120; E2 151-195 ; E2 271-365), the C-terminal part of HPV16 E6 (E6 81-158) and the central part of HPV16 E7 (E7 31-77) as the major immunogenic region within these antigens. Furthermore, we mapped ten distinct Th-epitopes within these proteins (DR1/E2 351-365, DR2/E2 316-330, DR2/E2 346-355, DR4/E2 51-70, E2 61-76, DQ6/E2 311-325, DR15/E7 50-62, DR3/E7 43-77, DQ2/E7 35-50, DR1/E6 127-142). By employing the IFNγ ELISPOT analysis, we detected in the CD45RO+ T-cell memory subset Th-immunity against HPV16 E2 and HPV16 E6 in healthy individuals, suggesting E2 and E6 directed protective immunity against previous HPV infection. Furthermore, Th-immunity was detected towards HPV16 E7 in subjects with HPV16+ lesions. Several of these responses matched with the three E7-derived Th-epitopes defined in this study. A number of other HPV16+ subjects did not display any E7specific type 1-cytokine producing T cell immunity, indicating failure of the immune response.

We have demonstrated that long peptides containing both CTL and Th-epitopes do not only induce antigen specific TH-cells but can induce antigen-specific CTL as well. Such peptides can also enhance antigen specific CTL responses. In contrast with immunization of C57/B16 mice with the minimal E1A-derived CTL epitope (SGPSNTPPEI) (SEQ. ID. NO. 1) which results in enhanced tumor outgrowth, immunization with the HPLC purified 32 amino acid long peptides containing this minimal CTL epitope of adenovirus E1 A protein (RECNSSTDSCDSGPSNTPPEIHPVVRLC-PIIKP) (SEQ. ID. NO. 2) resulted in protection against a challenge with adenovirus E1 A +RAS transformed tumor cells. Furthermore, HPV16 specific H-2Db-restricted CTL were induced upon immunization with 35 amino acid residue long peptides, containing the minimal 9 amino acid long CTL epitope RAHYNIVTF (SEQ. ID. NO. 3) as shown by the presence of H-2Db-RAHYNIVTF (SEQ. ID. NO. 3) tetramer positive CD8+T cells in a FACS analysis of spleen cells. Notably, in a direct comparison the CTL responses induced by the 35-mer peptide were by far stronger than CTL responses induced by the minimal CTL epitope and this difference was even more pronounced after specific activation of professional antigen presenting cells that can take up, process and present epitopes in the long peptide optimally. Furthermore, the present invention shows that stimulation of CTL by said long peptides, in the presence of antigen presenting cell activating agents, results in the complete eradication of small tumor nodules. In contrast, said minimal CTL epitope is not capable of inducing complete eradication of tumors in all mice.

Thus, vaccination with a long peptide of the invention circumvents the induction of tolerance which can occur when minimal CTL epitope peptides are used. A long peptide of the invention leads to a higher amount of CTL, generally associated with better protection. Without being bound by theory, at least one of two independent mechanisms account for this. One mechanism is the physical linkage of T-helper epitopes and CTL epitopes in one peptide. Another mechanism is the preferential presentation of at least one CTL-and/or T-helper-epitope present in a long peptide of the invention by professional antigen presenting cells. Because of its size, which excludes direct binding of a peptide of the invention to MHC class I, said peptide needs to be taken up by professional APC (eg. Dendritic Cells) that are able to process exogenously derived antigens and present peptides in MHC class I. Other cells are far less capable of processing and subsequent presenting epitopes. Thus background presentation by nonprofessional APC's is at least in part prevented. The effect of preferential targeting of a peptide of the invention to APC is enhanced when a long peptide of the invention is used together with a dendritic cell-activating agent, which is a preferred embodiment.

In another preferred embodiment said antigen comprises an auto-antigen, preferably a tumor cell specific auto-antigen or a functional part, derivative and/or analogue thereof. The term "auto-antigen" refers to an antigen that is encoded by the animal species the T-cell belongs to. It also refers to an antigen that arises or becomes expressed as a result of aberrant expression, modification, folding of proteins of said animal and/or mutation of sequences in the DNA or RNA of a cell encoding a protein of said animal. In a preferred embodiment said auto-antigen comprises a MAGE, CTA or PSA antigen. In a particularly preferred embodiment said peptide comprises an antigen specific T-cell epitope that induces tolerance and/or functional deletion of antigen specific CTL and/or T-helper cells in said system. It is well known in the art that antigen specific immune responses may be strengthened by providing systems capable of exhibiting said responses with an adjuvant. Adjuvants are also useful in the present invention. In a preferred embodiment said adjuvant comprises an exosome, a dendritic cell, MPL (monophosphoryl lipid A), poly I: C, Ampligen (poly I : poly $C^{12}$ U) and/or CpG nucleic acid.

According to the present invention, the advantage of epitope-linkage lies in the increased chance for simultaneous presentation of both the MHC class I and class II restricted epitopes on the surface of a single APC, thereby facilitating the delivery of cognate T cell help to CTL priming. Presentation by professional antigen presenting cells is preferred, because said cells can take up antigen more efficiently as compared to non-professional antigen presenting cells. Moreover, only professional antigen presenting cells are capable, in response to antigen uptake, of activating T-helper cells. Said activation is important for an optimal immune response.

The level of the CTL response is dependent on activation of dendritic cells as shown in this invention. One of the mechanisms that result in the high efficacy of our long peptide HPV16 E7-vaccine, is the fact that the natural HPV16 E7 sequence contains a T helper- and CTL epitope that are physically linked to each other. To obtain long peptides containing Th-epitopes and CTL epitopes that are preferably presented by professional antigen presenting cells, one can link two or more T-helper and CTL epitopes that are not naturally occurring sequences but that result in a considerable sized peptide. These T-helper and CTL epitopes can be derived from two different antigens, are preferably from the same tumor cell or pathogen but may be unrelated. According to the invention, a T cell response directed towards a specific antigen can as well be induced or enhanced with a long peptide of the invention comprising a Thepitope which is unrelated to said antigen. APC can generally be activated by said unrelated Th-epitope. However, preferably said Th-epitope is related to said antigen.

There are many systems available in which antigen specific immune responses can be induced and/or enhanced by providing said system with a peptide comprising an epitope specific for said antigen. For instance, in vitro cultures of peripheral blood mononuclear cells. Many other systems are available. However, in preferred embodiment of the invention said system comprises an animal. More preferably, said animal comprises a human.

A method of the invention is very suited for providing an animal with immunity against said antigen and/or for enhancing said immunity. Methods of the invention are suitable for any purpose that other immunization strategies are used for. Of old immunizations are used for vaccination purposes, i.e. for the prevention of disease. However, methods of the invention are not only suitable for preventing disease. Methods can also be used to treat existing disease, of course with the limitations that the disease is treatable by inducing and/or enhancing antigen specific T cell immunity. This feature can be used to treat, for instance, diseases associated with viral infections, such as some cancers. In principle, any disease curable in an immune related fashion can profit from methods of the invention In a preferred embodiment said animal is suffering from or at risk of suffering from a disease that is at least in part treatable or preventable. by inducing and/or enhancing said immune response. Preferably said disease comprises a viral disease and/or cancer. In another preferred embodiment said disease comprises a (myco)bacterial infection.

In another aspect the invention provides a peptide comprising 22-45 amino acid residues, comprising a T cell epitope specific for an antigen. Preferably, said peptide comprises at least two T cell epitopes specific for said antigen. Preferably said peptide comprises a CTL epitope for said antigen or a T helper cell epitope for said antigen. In a particularly preferred embodiment said peptide comprises a CTL epitope for said antigen and a T helper cell epitope for said antigen. Preferably said CTL and/or Thelper epitope for said antigen leads to tolerance or functional deletion of CTL and/or Thelper cells, respectively, specific for said epitope, when present on a peptide comprising 21 amino acid residues or less. In a preferred embodiment said peptide comprises between 22-35 amino acid residues. More preferably, said peptide comprises between 32-35 amino acids.

The invention further provides a use of a peptide of the invention for inducing and/or enhancing an immune response specific for said antigen. Provided is also the use of a peptide for the preparation of a vaccine. Preferably, for the preparation of a vaccine for the treatment and/or the prevention of an HPV-related disease and/or cancer. Further provided is a use for the preparation of a medicament. Preferably for the preparation of a medicament for the treatment of an individual suffering from or at risk of suffering from a viral disease and/or cancer. In another preferred embodiment said individual is suffering from or at risk of suffering from a (myco)bacterial disease.

In yet another aspect the invention provides a method of the invention further comprising obtaining an antigen specific T cell from said system. Thus also provided is an isolated T cell obtainable by a method of the invention. Said T-cell can of course also be used for preparing a medicament. Provided is also a vaccine comprising a peptide of the invention. Provided is also a medicament comprising a peptide or a T-cell of the invention.

Peptides of the invention can also be used to determine whether a collection of cells comprises an antigen specific T cell, said peptide comprising an epitope for said antigen. For instance for determining whether an individual comprises immunity for said antigen. The presence of said T cell is, preferably determined by ELISA, ELISPOT, delayed type hypersensitivity response, intracellular cytokine staining, and/or extracellular cytokine staining.

In another aspect the invention provides a peptide comprising an immunogenic epitope selected from an immunogenic region of human papilloma virus type 16 E2, E6 and E7 proteins. Preferably, said immunogenic regions comprises three separate regions in the E2 protein ($E2_{31-120}$; $E2_{151-195}$; $E2_{271-365}$) spanning amino acid 31-120, 151-195 and 271-365 of human papillomavirus 16 E2 protein, the C-terminal region of HPV16 E6 ($E6_{81\ 158}$) spanning amino acid region 81-158 in the HPV 16 E6 protein and the central part of HPV16 E7 ($E7_{31-77}$) spanning amino acid 31-77 of a human papilloma virus 16 E7 protein.

More preferably said immunogenic regions comprises in said E2 protein a region spanning amino acid 46-75, a region spanning amino acid 51-70, a region spanning amino acid 61-76, a region spanning amino acid 316-330, a regions spanning amino acid 311-325, a region spanning amino acid 346-355 and a region spanning amino acid 351-365. In addition said immunogenic regions comprises in said E6 protein a region spanning amino acid 81-158.

More preferably said immunogenic regions comprises in said E6 protein a region spanning amino acid 121-142, and a region spanning 127-140. In addition said immunogenic regions comprises in said E7 protein a region spanning amino acid 35-50, a region spanning amino acid 50-62 and/or a region spanning amino acid 43-77. A T-helper cell response can be very well elicited and/or enhanced, using anyone of the above-mentioned immunogenic regions. Notably, these immunogenic regions are able to elicit/enhance T-helper responses restricted by different HLA class II molecules.

In another aspect the invention provides a method to induce and/or enhance a T cell response directed towards an antigen, comprising contacting a T cell with a peptide, having a size of about 22-45 amino acid residues, which comprises a minimal T cell epitope of said antigen. Preferably, a peptide of the invention has a size of about 22-40 amino acid residues. Said minimal T cell epitope is preferably presented in the form of a peptide having a size of about 22-40 amino acid residues, because we found that the issue of tolerance or functional deletion of CTL by immunization with minimal epitopes can be circumvented by the use of long peptides (22-45; preferably 22-40 amino acid residues) which are able to prime CTL and/or T-helper cells. Said long peptides, comprising at least one minimal T cell epitope, are capable of inducing and/or enhancing a T cell response. Immunization with said long peptide, comprising a minimal T cell epitope, results in protection even when said minimal epitope leads to tolerance or functional deletion of virus-and tumor specific CTL when administered in a bare form to said CTL. Said minimal T cell epitope may be derived from an immunogenic region of the invention. Thus, in one aspect, the invention provides a method according to the invention, wherein said minimal epitope leads to tolerance or functional deletion of virus-and tumor-specific CTL when administered in a bare form to said CTL.

In another aspect the invention provides a method to induce and/or enhance a T cell response directed towards an antigen, comprising contacting said T cell with a peptide, having a size of about 22-45 amino acid residues, which comprises a minimal T cell epitope of said antigen. Said minimal T cell epitope is presented in the form of a peptide having a size of about 22-45, preferably of about 22-40, amino acid residues because we found that the induction of (virus-and tumor-specific) CTL is more efficient with said long peptides and results in higher numbers of antigen-specific CTL. The use of said long peptides results in a more efficient presentation of the comprised CTL and/or Th epitopes. Without being bound by theory it is thought that long peptides need to be processed and presented by professional antigen presenting cells. Supporting evidence for this theory comes from a more efficient induction of CTL immunity after vaccination with said long peptides and professional antigen presenting cells-activating agents.

Contacting a T cell with a peptide, in terms of the invention, is preferably performed by means of a MHC class I or MHC class II molecule. Said MHC molecule may present said peptide after processing of the peptide to said T cell. An antigen of the invention can be an antigen derived from a virus, a bacterium or associated with tumor cells. Preferably an antigen comprises a protein of human papillomavirus (HPV). More preferably, said HPV comprises HPV 16. In a most preferred aspect, said protein comprises HPV 16 E2, E6 and/or E7. Said long peptides are capable of priming CTL and/or T-helper cells. Therefore, in one aspect the invention provides a method according to the invention, wherein said T cell comprises a CD8+ CTL. Alternatively, said T cell comprises a CD4+ T helper cell.

By inducing a T cell response is meant herein that a T cell response directed towards a certain antigen is elicited. Before said induction, said T cell response was not present, or below detection levels or not functional. By enhancing a T cell response is meant herein that the overall action of T cells directed towards a certain antigen is made higher and/or more efficient compared to the overall action of said T cells before enhancement. For instance, after said enhancement more T cells directed towards said antigen may be generated. As a result, the action of the additionally generated T cells increases the overall action against said antigen. Alternatively, said enhancement may comprise the increment of the action of T cells directed towards said antigen. Said T cells may for instance react stronger and/or quicker with said antigen. Of course, the result of said enhancement may be generation of additional T cells together with increment of the action of said T cells. Alternatively, said enhancement may comprise generation of additional T cells, or increment of the action of T cells, only.

A minimal T cell epitope is defined herein as a peptide derived from an antigen, capable of inducing a T cell response against said antigen. Said minimal T cell epitope is suitable to be bound by a class I or II Major Histocompatability molecule. Typically, a minimal CTL epitope consists of 8-11 amino acids. A minimal T cell epitope which is to be bound by an MHC class II molecule preferably at least consists of 11 amino acids. In terms of the invention, administering a minimal epitope in a bare form means that said epitope is administered as a peptide having the size of said epitope, or as a peptide comprising said epitope flanked on one or both sides with additional sequences, the size of said peptide being less than 22 amino acid residues. For instance, said epitope may be flanked by processing sites.

With the teachings of the present invention it is possible to induce and/or enhance a T cell response directed towards an antigen using a peptide of the invention. Of course, examples of said peptide are also herewith provided. Thus, one embodiment of the invention provides a peptide, having a size of about 22-45, preferably of about 22-40 amino acid residues, comprising at least one minimal T cell epitope. Said peptide comprises a minimal CTL epitope, and/or a minimal T helper cell epitope. Preferably said peptide comprises an immunogenic epitope of the invention. A peptide of the invention is more suitable to be used for vaccination purposes than a minimal epitope in a bare form, if immunization with said minimal epitope leads to tolerance or functional deletion of CTL. Thus in one aspect the invention provides a peptide according to the invention, wherein said minimal CTL epitope leads to tolerance or functional deletion of virus- and tumor-specific CTL when administered in a bare form to said CTL. A peptide of the invention preferably has a size of about 22-45 amino acid residues. Preferably, a peptide of the invention has a size of 22-35 amino acid residues. More preferably, a peptide of the invention comprises 32 amino acid residues. In another aspect a peptide of the invention comprises a size of 35 amino acid residues.

A peptide of the invention is more suitable to be used for vaccination purposes than a minimal epitope in a bare form, if immunization with a peptide of the invention leads to higher numbers of CTL. This can be achieved by assuring that presentation predominantly takes place by professional antigen presenting cells. Thus in one aspect the invention provides a peptide according to the invention wherein said peptide leads to higher numbers of virus-and/or tumor-specific CTL than when minimal CTL epitopes are administered. In another aspect a peptide of the invention leads to a vigorous CTL response capable of eradicating (small) tumor nodules.

The art currently knows many ways of generating a peptide. The invention is not limited to any form of generated peptide as long as the generated peptide comprises a minimal T cell epitope. By way of example, a peptide of the invention can be obtained from protein E2, E6 or E7, synthesized in vitro or by a cell, for instance through an encoding nucleic acid. A peptide of the invention can be present as a single peptide or incorporated into a fusion protein. In one embodiment said peptide is flanked by processing sites allowing processing of said peptide inside a cell such as to allow transport and/or incorporation into an MHC molecule on the surface of said cell. In a preferred embodiment a peptide of the invention is after processing capable of complexing with an MHC class II molecule. MHC class II restricted T-cell immunity is currently considered to be important in eradication of for instance tumor cells although said tumor cells often do not express MHC class II molecules. Peptides of the invention are particularly well suited for eliciting, inducing and/or stimulating both MHC class I and MHC class II dependent T cells. Thus, in one aspect the invention provides a use of a peptide of the invention to induce and/or enhance a T cell response directed towards an antigen. A method to elicit and/or enhance an immune response in an individual, comprising administering to said individual a peptide of the invention is also herewith provided. In another aspect, the invention provides a use of a peptide of the invention for the preparation of a vaccine. Preferably, said vaccine comprises a vaccine for, at least in part, prophylaxis of an HPV-related disease.

For instance, reactive T cells to HPV E2 and E6 protein have been found in healthy individuals indicating that the identified immunogenic regions in the HPV16 E2 and E6 protein comprises epitopes relevant for prophylactic anticancer treatments based on vaccination and/or adoptive immunotherapy approaches. Additionally, reactive T cells to HPV E7 and HPV E6 protein have been found in subjects comprising CIN III lesions and in subjects having cervical cancer. This indicates that the identified immunogenic regions of the HPV16 E7 and E6 protein comprise epitopes relevant for anticancer treatments based on vaccination and/or adoptive immunotherapy approaches.

Peptides of the invention are suited for the generation and/or induction of HPV specific T-cells. In one aspect the invention therefore provides a method for generating a human papilloma virus 16 specific T-cell comprising contacting a collection of naive T-cells with a peptide of the invention and culturing at least part of said collection of T-cells. In another aspect the invention provides a method for inducing antigen-specific cytokine (like, for instance, IL-2 or IFNγ) production by a human papilloma virus 16 specific memory T-cell comprising contacting a collection of T-cells of a subject infected with human papilloma virus 16 with a peptide of the invention and culturing at least part of said collection of T-cells. In a preferred embodiment of these aspects said human papilloma virus 16 specific T-cell is isolated.

In yet another aspect a method of the invention further comprises obtaining a T cell directed towards an antigen, comprising inducing and/or enhancing a T cell with a method of the invention and collecting formed T cells directed towards said antigen. Of course, an isolated T cell obtainable by a method of the invention is also provided herein. Said T cell can be used in many ways, for instance for the detection of an epitope of the invention for instance in a diagnostic assay. However, preferably said T cell is used in immunotherapy approaches. Such approaches incorporate but are not limited to approaches wherein such T cells are infused into a subject suffering from an HPV-16 induced cervical cancer or lesion. Thus in one aspect the invention provides a use of a T cell of the invention for at least in part treatment of an HPV-related disease. In such approaches it is preferred that said T cell and said subject are histocompatible.

Although this may not always be true, in some cases mismatches for histocompatible even enhance the functionality of said T cell in said subject. The risk of developing graft versus host disease can often be limited by assuring that T cells not restricted to an epitope of the invention are not present in a graft given to said subject. Of course, host versus graft responses resulting in elimination of infused T cells of the invention can occur. To limit such responses histocompatibility is preferred. However, in case wherein eradication of tumor cells is very rapid, host mediated removal of grafted cells can be an advantage as an additional safety feature of immunotherapy. In one embodiment the invention therefore provides a method for eliciting and/or enhancing an HPV16 E2, E6 and/or E7 protein specific immune response in an individual comprising administering to said individual a peptide of the invention or a T-cell of the invention. A peptide of the invention is particularly suited to elicit HPV 16 specific immune responses in an individual. These immune responses can be sufficiently high to provide a subject with protection against infection by HPV-16.

However, a peptide or a T cell of the invention can also be used to aid in combating an already present infection in a subject. Thus another embodiment of the invention provides a use of a peptide or a T cell of the invention for the preparation of a medicament. Preferably, said medicament comprises a medicament for an HPV-related disease. Of course, a vaccine and/or a medicament comprising a peptide of the invention is also provided herewith. Said vaccine is particularly suitable for prophylaxis of an HPV related disease. Therefore the invention also provides a method for, at least in part, prophylaxis of an HPV-related disease, comprising administering to an individual a vaccine of the invention. A medicament of the invention is of course particularly suitable for treatment of an HPV related disease.

Thus, a method for, at least in part, treatment of an HPV-related disease, comprising administering to an individual a medicament of the invention is also provided herewith. In another aspect the invention provides a method for determining whether a collection of T cells comprises a memory T cell specific for an epitope comprising providing said collection of T cells with a peptide of the invention comprising said epitope, culturing said collection of T cells in the presence of an antibody specifically directed towards an antigen-specific cytokine (like, for instance, IL-2 or IFNγ) and detecting any bound antigen-specific cytokine. In one embodiment said antibody is bound to a solid phase, preferably a solid surface. Said method is very useful to determine whether an individual has a T cell response directed towards a certain antigen, for instance towards an HPV protein. Said method can be used for diagnosis of an HPV infection.

Alternatively, said method is suitable to determine whether a T cell response is elicited after vaccination of an individual. Preferably, said individual is provided with a vaccine of the invention. Thus one embodiment of the invention provides a use of a peptide of the invention to determine the presence of a T cell directed towards an antigen. In one embodiment, said presence of said T cell is determined in a sample. For instance, a blood sample from an individual can be obtained. After that, the presence of a T cell directed towards a specific antigen can be determined using a peptide of the invention, in an immunologic assay. For instance, the above mentioned method can be used. In this method, the detection of bound antigen-specific cytokine (like, for instance, IL-2 or IFNγ) indicates the presence of said T cell. Of course, a person skilled in the art can think of many more techniques for detection of a T cell directed towards a certain antigen, using a peptide of the invention. For instance ELISA, ELISPOT, delayed type hypersensitivity (DTH) response, intracellular cytokine staining and extracellular cytokine staining or the use of tetrameric WIC class II molecules comprising said peptides are important techniques, known by the artisan.

The invention is further explained by the use of the following illustrative examples.

EXAMPLES

Example 1

Material and Methods
Subjects and Controls.

Samples of umbilical cord blood mononuclear cells (CBC) were used as immunologically naive controls for influenza matrix-specific responses. PBMC of HLA-typed, anonymous healthy blood bank donors (D) obtained after informed consent, served as control PBMC for HPV16 E7 and influenza matrix-specific responses. Since these donors are anonymous, no additional data is available. However, donors with a known recent history of infection, including abnormal pap-smear, were, as part of normal regulations, discouraged to donate blood. The study of subjects (S; Table I) with CIN or cervical carcinoma in this paper was nested in the "CIRCLE study' that investigates cellular immunity against HPV16 infected cervical lesions. Women presenting with histologically proven CIN III or cervical carcinoma at the department of gynecology of the Leiden University Medical Center (LUMC) were, after informed consent, enrolled in this study. The study design was approved by the ethics committee of the LUMC. Blood was drawn at day of treatment. Subjects with CIN III were treated by LEEP or cold knife conisation. In case of stage IB-IIA a radical hysterectomy was performed. All individuals for whom enough PBMC were available were typed for HLA MHC class II (Naipal et al., 1984). Subjects were typed for HPV16 using HPV16-specific primers on DNA isolated from paraffin-embedded sections of biopsies or surgical resection specimens (Claas et al., 1989). Since HPV-specific T-helper response were expected to be found in subjects with progressive disease (de Gruijl et al., 1998), we chose to analyse three subjects presenting with CIN III, 4 subjects with stage IB cervical cancer and 4 subjects with recurrent cervical cancer.

Antigens

The peptides used spanning the E7 protein consisted of nine overlapping 22-mer peptides and are indicated by their first and last amino acid in the protein (1-22,11-32, 21-42, 31-52,41-62,51-72,61-82,71-92 and 77-98) or 4 long peptides defined by amino acids 1-35, 22-56,43-77 and 64-98. The peptides spanning the influenza matrix 1 protein of A/PR/8/43 that were used as control peptides in the ELISPOT assay consisted of sixteen 30-mer peptides overlapping by 15 amino acids. Peptides were synthesized and dissolved as described previously (van der Burg et al., 1999).

Recombinant HPV16-E7 protein, HPV16-E6 protein and HIV-1 RT protein (the latter two proteins served as control proteins in proliferation assays) were produced in recombinant E. coli transformed with Pet-19b-HPV16-E7, Pet-19b-HPV16-E6 (De Bruijn et al., 1998) or Pet-19b-HIV-1 reverse transcriptase (RT) and purified as described previously (van der Burg et al., 1999).

Memory Response Mix (MRM): A mixture of tetanus toxoid (1 LF/ml; National Institute of Public Health and the Environment, Bilthoven, The Netherlands) and *Mycobacterium tuberculosis* sonicate (2.5 µg/m1; generously donated by Dr. P. Klatser, Royal Tropical Institute, The Netherlands) was used to control the capacity of PBMC to proliferate in response to typical recall antigens.

HLA-DR-peptide Binding Assay.

Binding of peptides was measured as reported previously (van der Burg et al., 1999). Briefly, as a source of HLA-DR molecules B-lymphoblastic cell lines homozygous for HLA-DR were used: LG2.1 (DRB*0101, DR1), IWB (DRB1*0201, DR2), HAR (DRB*0301, DR3), BSM (DRB*0401, DR4) and Pitout (DRB1*0701, DR7). DR molecules were purified by affinity chromatography and the purity confirmed by SDS-PAGE. The analysis of peptide binding to purified HLA-DR molecules was performed using N-terminally fluorescence-labeled standard peptides. As standard fluorescent peptides in the binding assays, either HA 308-319 (PKYVKQNTLKLAT, DR1 and DR2), (SEQ. ID. NO. 4) hsp65 3-13 (KTIAYDEEARR, DR3) (SEQ. ID. NO. 5), $HA_{308-319}$ Y→F (PKFVKQNTLKLAT, DR4) (SEQ. ID. NO. 6) or Ii 80-103 (LPKPPKPVSKMRMATPLLMQALPM, DR7) (SEQ. ID. NO. 7) were used.

Immunogenicity Assay.

HPV16-E7 derived peptide induced proliferation of PBMC isolated from blood obtained from healthy donors was measured as described previously (van der Burg et al., 1999).

Briefly, PBMC were seeded at a density of $1.5 \times 10^5$ cells/well of a 96 well U-bottom plate (Costar, Cambridge, Mass.) in 200, µl of ISCOVE's medium (Gibco) enriched with 10% autologous serum, in the presence or absence of 10 µg/ml of indicated 22 mer E7 peptide. As positive control, PBMC were cultured in the presence of a Memory Response Mix. Peptide specific proliferation was measured at day 6 by tritiumthymidine incorporation. Peptides were scored as immunogenic, i. e., able to stimulate T-cells, when the proliferation of >25% of the 8 test wells exceeded the mean proliferation +2 times the standard deviation of medium control wells.

Proliferation Assays

Cultures were pulsed with 0.5 µ Ci [3H] thymidine (5Ci/mM, Amersham, UK) per well for 18 hours. Plates were harvested with a Micro cell Harvester (Skatron, Norway).

Filters were packed in plastic bags containing 10 ml of scintillation fluid and subsequently counted in a 1205 Betaplate counter (Wallac, Turku, Finland).

MHC class II blocking experiments were carried out as described before using murine monoclonal antibodies against HLA-DQ SPV. L3, against HLA-DR B8.11.2 and against HLA-DP B7/21 (van der Burg et al., 1999). Antibodies were added to APC 1 h prior to protein-APC incubation.

Isolation and Expansion of HPV16-E7-specific T-helper Cells.

Peptide-specific T-cell bulk cultures were generated as described previously (van der Burg et al., 1999) using either the E7 22-mer or E7 35-mer peptides. Specific proliferation was measured by incubation of 50,000 responders with an equal amount of irradiated (30Gy) APC (autologous PBMC unless indicated otherwise) and peptide or protein as indicated. E7-peptide and-protein-specific bulk T-cells were cloned by limiting dilution as described previously (van der Burg et al., 1999).

Cytokine Assays

To determine specific excretion of cytokines, T-cell clones were stimulated by incubation of 50.000 T-cells with an equal amount of APC (30Gy) together with 10 µg/ml peptide, control peptide, E7 protein or control protein as indicated. After 24 hours of incubation, supernatant was harvested and replicate wells were pooled. Cytokine production was measured by Enzyme-Linked Immunosorbent Assay (ELISA) as described previously (van der Burg et al., 1999).

Analysis of Antigen-specific T-cells by ELISPOT

PBMC or cord blood cells (CBC) were seeded at a density of $2 \times 10^6$ cells/well of a 24 well plate (Costar, Cambridge, Mass.) in 1 ml of ISCOVE's medium (Gibco) enriched with 10% FCS, in the presence or absence of 5 µg/ml of indicated E7-derived 22-mer peptide. As positive control PBMC were cultured in the presence of indicated pools of influenza A/PR/8/34 M1 protein derived peptides consisting of 4 overlapping 30 amino acid long peptides in each pool. Based on our observations, we used a 4-day stimulation before PBMC were transferred to the ELISPOT plates. This resulted in a pronounced IFNγ-production towards influenza M1-derived peptides in the CD45RO+ (memory) subset of T-cells but not in naive T-cells obtained from adult PBMC (unpublished observations).

Following 4 days of incubation at 37° C., PBMC were harvested, washed and seeded in six replicate wells at a density of $10^5$ cells/well of a Multiscreen 96-well plate (Millipore, Etten-Leur, The Netherlands) coated with a IFNγ catching antibody (Mabtech AB, Nacha, Sweden). The ELISPOT was further performed according to the instructions of the manufacturer (Mabtech). The number of spots were analyzed with a fully automated computer assisted video imaging analysis system (Carl Zeiss Vision).

Specific spots were calculated by subtracting the mean number of spots+2×SD of the medium only control from the mean number of spots of experimental wells. Antigenspecific T-cell frequencies were considered to be increased compared to non-responders when T-cell frequencies were >1/10, 000 PBMC.

Results
Identification of the Inmunogenic Sequences within HPV16 E7.

We set out to identify the sequences within the HPV16 E7 protein that function as major immunogenic determinants in the context of MHC class II. A set of HPV16 E7 derived overlapping peptides was tested for binding to HLA-DR 1,2,3,4 and 7 in a quantitative peptide/MHC binding assay (Geluk et al., 1995). Together, these HLA-DR molecules cover at least 50-60% of the caucasian, oriental and negroid populations (Baur et al., 1984). Four peptides, $E7_{1-22}$, $E7_{41-62}$, $E7_{51-72}$ and $E7_{77-98}$, bound to three or more different HLA-DR molecules (Table II) : peptide $E7_{1-22}$ bound to HLA DR2,3,4 and 7, peptide $E7_{41-62}$ bound to DR1,2,3 and 4 whereas peptide $E7_{51-72}$ bound to DR1, 3 and 7 and peptide $E7_{77-98}$ bound to DR1, 2 and DR7. This is in accordance with the fact that the peptide binding restrictions for MHC class II molecules were found to be less strict than those for MHC class I (Rammensee et al., 1995). Of note, these peptides failed to bind to one or two other DR molecules tested indicating that their binding, although rather ubiquitous in character, was specific.

Our subsequent experiments focused on the four peptides binding to multiple HLA-DR molecules, as these are the most likely to comprise naturally presented T-helper (Th) epitopes (Geluk et al., 1998). We analyzed whether the peptides could stimulate T-cells to proliferate by adding these to PBMC from 13 HLA-typed healthy blood donors. This assay does not discriminate between the reactivity of memory T-cells and naive, in vitro, primed T-cells but can be readily employed for identification of immunogenic peptides (van der Burg et al., 1999). All four peptides were able to stimulate proliferative responses in PBMC from multiple donors (Table II). Most PBMC cultures reacted to the peptides $E7_{41-62}$ and $E7_{51-72}$ indicating that the central region of the E7 protein harbors the most immunogenic sequences and is likely to be targeted by the immune system in HPV16 infected individuals.

TABLE I

Subject characteristics

| Patient number | Age | HPV type | MHC class II type | Stage of Disease |
|---|---|---|---|---|
| 1 | 38 | 16 | HLA DR4, 11(5); DQ3 | CIN III |
| 2 | 41 | 16 | HLA DR15(2), 3; DQ6(1), 2 | CIN III |
| 3 | 32 | 16 | HLA DR15(2), 4; DQ3, 6 | CIN III |
| 4 | 67 | 16 | HLA DR15(2), 4; DQ6(1), 8(3) | FIGO IB |
| 5 | 59 | 16 | HLA DR11(5); DQ3 | FIGO IB |
| 6 | 36 | 16 | Non-Available | FIGO IB |
| 7 | 28 | 16 | HLA DR1, 7; DQ5(1), 2 | FIGO IB |
| 8 | 48 | 16 | HLA DR15(2), 7; DQ6(1) | Recurrent cervical carcinoma |
| 9 | 46 | 16 | HLA DR15(2), 7; DQ6(1), 2 | Recurrent cervical carcinoma |
| 10 | 47 | 16 | HLA DR6, 7; DQ1, 2 | Recurrent cervical carcinoma |
| 11 | 46 | 16 | HLA DR3, DQ2 | Recurrent cervical carcinoma |

TABLE II

Binding capacity and immunogenicity of HPV16-E7 derived peptides

| E7 | Binding | | | | | Immunogenicity | | | |
|---|---|---|---|---|---|---|---|---|---|
| | | | | | | D #1 DR1,3 | D #2 DR1,4 | D #3 DR2,4 | D #4 DR3,6 |
| aa | DR1 | DR2 | DR3 | DR4 | DR7 | DQ1,2 | DQ5,6 | DQ6,8 | DQ6,2 |
| 1-22[a] | >70[b] | 10 | 0.8 | 30 | 7 | –[c] | – | – | – |
| 11-32 | >70 | >70 | 50 | >70 | >70 | | | | |
| 21-42 | >70 | 12 | >70 | >70 | >70 | | | | |
| 31-52 | >70 | >70 | >70 | >70 | NT | | | | |
| 41-62 | 7.4 | 50 | 55 | 38 | >70 | – | – | + | – |
| 51-72 | 70 | >70 | 50 | >70 | 11 | – | – | – | – |
| 61-82 | >70 | 15 | 65 | >70 | >70 | | | | |
| 71-92 | 12 | 2 | >70 | >70 | >70 | | | | |
| 77-98 | 46 | 22 | >70 | >70 | 0.9 | + | – | – | – |
| Memory Response Mix | | | | | | + | + | + | + |

TABLE II-continued

Binding capacity and immunogenicity of HPV16-E7 derived peptides

| E7 aa | Immunogenicity | | | | | | | | |
|---|---|---|---|---|---|---|---|---|---|
| | D #5 DR2,3 DQ1,2 | D #6 DR2,3 DQ6,2 | D #7 DR1,3 DQ5,2 | D #8 DR2,13 DQ6 | D #9 DR4,7 DQ3 | D #10 DR1,3 DQ5,2 | D #11 DR7 DQ2 | D #12 DR3,13 DQ6,2 | D #13 DR7,13 DQ6,3 |
| 1-22[a] | + | + | − | − | − | − | − | − | + |
| 11-32 | | | | | | | | | |
| 21-42 | | | | | | | | | |
| 31-52 | | | | | | | | | |
| 41-62 | + | + | + | + | + | + | − | − | + |
| 51-72 | + | + | + | + | + | + | − | − | + |
| 61-82 | | | | | | | | | |
| 71-92 | | | | | | | | | |
| 77-98 | − | − | − | + | + | + | − | − | + |
| Memory Response Mix | + | + | + | + | + | + | + | + | + |

[a] First and last amino acid number of 22-mer overlapping peptides derived from the HPV16-E7 protein.
[b] Binding capacity of each peptide is expressed as the IC50 value: this is the test peptide concentration (μM) at which 50% of the maximal binding of the standard fluorescence labeled peptide is inhibited. >70, indicates undetectable binding.
[c] Fresh PBMC derived from HLA-DR and -DQ typed healthy blood donors (D) were stimulated with peptides that bound to ≥3 different HLA-purified DR molecules. Donors were considered to react specifically to a peptide when >25% of all wells tested displayed a proliferation that exceeded the mean + 2x standard deviation of the medium only control. More then 85% of all wells stimulated with the Memory Response Mix were found positive.

TABLE III

Evaluation of HPV16 E7-specific T cell responses by IFNγ ELISPOT

| | CBC #1 | CBC #2 | CBC #3 | D#20 | D#21 | D#22 | D#23 | D#24 | D#25 | D#26 | S#1 |
|---|---|---|---|---|---|---|---|---|---|---|---|
| HLA-DR | NA | NA | NA | 3[b] 13 (6) | 15 (2) 13 (6) | 1 4 | 2 | 4 8 | 1 | 11 (5) 7 | 4 11 (5) |
| HLA-DQ | NA | NA | NA | 1,2 | 6 (1) | 3,5 | 1 | 4,8 | 5 | NA | 3 |
| E7 | | | | | | | | | | | |
| 1-22[a] | | | | <1 | 1 | <1 | <1 | <1 | <1 | <1 | <1 |
| 11-32 | | | | <1 | 1 | <1 | 15 | <1 | <1 | <1 | <1 |
| 21-42 | | | | <1 | <1 | 2 | <1 | <1 | <1 | <1 | <1 |
| 31-52 | | | | <1 | <1 | <1 | <1 | <1 | <1 | 1 | <1 |
| 41-62 | | | | <1 | 2 | 2 | <1 | <1 | <1 | 1 | <1 |
| 51-72 | | | | <1 | <1 | 4 | <1 | <1 | <1 | 1 | 32 |
| 61-82 | | | | <1 | <1 | <1 | <1 | <1 | <1 | 1 | <1 |
| 71-92 | | | | <1 | <1 | <1 | <1 | <1 | <1 | 2 | <1 |
| 77-98 | | | | <1 | <1 | <1 | <1 | <1 | <1 | 1 | <1 |
| M1 | | | | | | | | | | | |
| pool 1 | <1[c] | <1 | <1 | 8 | 9 | 46 | <1 | 7 | 5 | 13 | <1 |
| pool 2 | <1 | <1 | <1 | 12 | 36 | 41 | <1 | 28 | <1 | 65 | 8 |
| pool 3 | <1 | <1 | <1 | <1 | 47 | 42 | <1 | <1 | 9 | 17 | 92 |
| pool 4 | <1 | <1 | <1 | <1 | 47 | 38 | 27 | <1 | 15 | 2 | <1 |

| | S#2 | S#3 | S#4 | S#5 | S#6 | S#7 | S48 | S#9 | S#10 | S#11 |
|---|---|---|---|---|---|---|---|---|---|---|
| HLA-DR | 15 (2) 3 | 15 (2) 4 | 15 (2) 4 | 11 (5) | NA | 1 7 | 15 (2) 13 (6) | 15 (2) 7 | 6 7 | 3 |
| HLA-DQ | 6 (1), 2 | 6 (1), 3 | 6 (1), 8 (3) | 3 | NA | 5 (1), 2 | 6 (1) | 6 (1), 2 | 1,2 | 2 |
| E7 | | | | | | | | | | |
| 1-22[a] | <1 | <1 | <1 | 16 | <1 | <1 | <1 | <1 | <1 | <1 |
| 11-32 | <1 | <1 | <1 | <1 | <1 | <1 | <1 | <1 | <1 | 8 |
| 21-42 | <1 | <1 | <1 | 4 | <1 | <1 | 1 | <1 | <1 | 2 |
| 31-52 | 8 | <1 | <1 | <1 | <1 | <1 | 23 | <1 | <1 | 14 |
| 41-62 | 14 | <1 | <1 | <1 | <1 | <1 | 19 | <1 | <1 | 5 |
| 51-72 | 76 | <1 | <1 | 98 | <1 | <1 | <1 | <1 | <1 | <1 |
| 61-82 | <1 | <1 | <1 | <1 | <1 | <1 | <1 | <1 | <1 | 13 |
| 71-92 | <1 | <1 | <1 | <1 | <1 | <1 | <1 | <1 | <1 | <1 |
| 77-98 | <1 | <1 | <1 | 12 | <1 | <1 | 6 | <1 | <1 | 6 |
| M1 | | | | | | | | | | |
| pool 1 | <1 | 27 | <1 | <1 | 1 | 113 | <1 | <1 | <1 | 15 |
| pool 2 | <1 | 29 | 47 | 2 | 8 | 66 | 11 | <1 | <1 | 19 |

TABLE III-continued

Evaluation of HPV16 E7-specific T cell responses by IFNγ ELISPOT

| pool 3 | 6  | <1 | 59 | 100 | <1 | 41 | 39 | <1 | <1 | 20 |
| pool 4 | 22 | 15 | <1 | 10  | <1 | 34 | 17 | <1 | 21 | 28 |

<sup>a</sup>First and last amino acid number of 22-amino acid long peptides derived from the HPV16-E7 protein that were used to stimulate T-cells of umbilical cord blood cells (CBC), PBMC from donors (D) or PBMC from HPV16+ subjects (S). For the influenza M1 protein only the number of the pool is indicated. Each pool consists of four 30 amino acid long peptides that overlap by 15.
<sup>b</sup>HLA class II typing of each individual. NA, non available
<sup>c</sup>The number of antigen-specific cells per 100,000 cord blood cells or PBMC. Frequencies ≥1/10,000 are depicted in bold. Underscored are the responses that match in specificity to that of Th-clones described in FIGS. 1,2,3.

Mapping of Naturally Processed T-helper Epitopes in HPV16 E7.

As a next step in the identification of Th-epitopes in HPV16 E7, peptide specific bulk T-cell cultures were generated from PBMC of HLA-typed healthy blood donors by repeated stimulation with several long peptides covering the central region of E7. The responding T-cells were subsequently tested for recognition of antigen presenting cells (APC) pulsed with either peptide or whole E7 protein. In the latter setting, presentation of the relevant peptide-epitopes requires antigen-uptake and-processing.

Approximately 30% of the Th-cell cultures generated specifically responded to the peptides against which they were raised. Of these, three cultures also showed modest but specific activity against E7 protein pulsed APC, indicating the presence of Th-cells with the capacity to respond against naturally processed antigen (FIGS. 1a, 2a and 3a).

FIG. 1b shows the reactivity of a Th-clone that was isolated from HLA-DR15, 4 and DQ6,7 positive PBMC raised against peptide $E7_{41-62}$. These Th-cells specifically respond to APC pulsed with peptide $E7_{41-62}$, peptide $E7_{43-77}$ or E7 protein. The specificity of the response by this Th-clone exceeded that of the polyclonal culture from which this Th-clone was isolated (compare to FIG. 1a), illustrating that by limiting dilution we have succeeded in isolating the T-cells of interest. Further studies using MHC class II blocking antibodies against HLA-DR,-DQ or-DP (FIG. 1b) and partially MHC class II matched APC revealed that the Th-clone was restricted by HLA-DR15 (FIG. 1c). Fine mapping of the epitope showed that the core sequence recognized was $E7_{50-62}$.

Furthermore, this Th-clone produced the Th type 1 cytokine IFNγ (FIG. 1d). In a similar fashion a HPV16 E7-specific Th-clone was obtained from HLA-DR3, DQ2 positive PBMC stimulated with peptide $E7_{22-56}$ (FIG. 2a). Also this Th-clone secreted IFNγ upon triggering by peptide $E7_{22-56}$ and E7 protein pulsed APC (FIG. 2b). Further analysis showed that this Th-clone recognized the core sequence $E7_{35-50}$, as indicated the fact that both peptides $E7_{30-50}$ and $E7_{35-55}$ recognized, in an HLA-DQ2 restricted fashion (FIG. 2c). A third type 1 cytokine producing Th-clone with distinct specificity was derived from a HLA-DR1,3 and DQ2 positive PBMC culture stimulated with peptide $E7_{43-77}$ (FIGS. 3a-3b). This clone was HLA-DR3 restricted (FIGS. 3c-3d) and produced IFNγ upon recognition of both peptide and protein pulsed APC (FIG. 3e). Whereas peptide E743-77 was recognized, the smaller peptide E741 62 was not, indicating that the C-terminal part of the E743-77 peptide harbors the core epitope. In conclusion, using established Th-clones we mapped three naturally processed epitopes in HPV16 E7. It is conceivable that HPV16+ individuals expressing the relevant MHC class II molecules display in vivo induced Th-immunity against these peptides.

Memory T-helper Responses in Subjects with HPV16+ CIN III Lesions or Cervical Carcinoma.

In an approach parallel to the mapping of Th-epitopes using PBMC cultures of healthy individuals, the response against HPV16 E7 in subjects with HPV16+ lesions was analysed (see Table I for subject characteristics). Primary, in vitro, stimulation of naive T-cells from newborns or adults can result in the production of IL-2 and proliferation of T-cells. However, at this stage such T-cells fail to secrete IFNγ. The production of IFNγ follows when the antigen is encountered again (Early and Reen, 1999; Pittet et al., 1999; Sallusto et al., 1999). This feature allowed us to discriminate between in vitro primed and memory T-cell responses by ELISPOT. Th-responses against the influenza A matrix (M1) protein, which are readily detectable in PBMC of most donors of diverse HLA-types (Table III and our unpublished observations), were measured in parallel as a positive control for the detection of memory T-cell immunity in the assay. Stimulation with MI-peptides of MACS-separated CD45RA+ (naive) T-cells and CD45RO+ (memory) T-cells resulted in the production of IFNγ in the CD45RO+ subset only, confirming that our ELISPOT setup specifically detects memory responses (FIG. 4). Furthermore, cord blood cells (CBC), in accordance with their naive phenotype, did not react by secreting IFNγ when stimulated in vitro with influenza MI derived peptides. In addition to the PBMC from all healthy donors, those from 9/11 of the HPV16+ subjects reacted to one or more pools of MI-peptides (Table III).

Analysis of HPV16 E7-immunity revealed responses against one or more peptides in ⅔ subjects diagnosed with CIN III and in ⅜ subjects with cervical carcinoma. In addition, one of the seven donors tested displayed immunity against a peptide. The central region of HPV16 E7 that is covered by the peptides $E7_{31-52}$, $E7_{41-62}$ and $E7_{51-72}$ was targeted by the immune system of all five HPV16+ individuals (Table III), not only confirming that this region is highly immunogenic (Table II) but also demonstrating that this region harbors epitopes that are targeted by natural immune responses against HPV16. Interestingly, the specificity of IFNγ responses detected in three HPV16+ subjects, in combination with their HLA-type, matched that of the established Th-clones for which we examined specificity and HLA-restriction in detail (FIGS. 1a-3e).

In particular (Table III, underscored frequencies), subject 2 exhibited significantly increased immunity matching the specificity of the two HLA-DR restricted clones as well as weak immunity matching the HLA-DQ2/$E7_{35-50}$ clone. Subject 8 displayed a response matching the DR15/$E7_{50-62}$ clone, whereas subject 11 showed reactivity matching the HLA-DQ2/$E7_{35-50}$ clone. It should be noted that in other subjects expressing the relevant MHC class II molecules such responses could not be detected (subjects 3,4,7 and 10).

Example 2

Materials and Methods

Lymphocytes

Peripheral blood mononuclear cells (PBMC) and serum of HLA-typed anonymous healthy blood donors were obtained after informed consent. Because these donors are anonymous, no data on medical history are available. Importantly, donors with a known recent history of infection, including abnormal pap-smear were, as part of normal regulations, discouraged to donate blood.

Antigens

A set of peptides spanning the whole HPV16 E2 protein consisting of 23 overlapping peptides, 22 of which have a length of 30 amino acids and one of which ($E2_{331-365}$) has a length of 35 amino acids, was used. These peptides share an overlap of 15 amino acids.

For epitope fine-mapping and the determination of cross-reactivity of HPV16-E2 specific Th-clones, peptides with a length of 15 and 20 amino acids were used. The peptides spanning the Influenza Matrix 1 protein of A/PR/8/34, which were used as control peptides in ELISPOT assays, consisted of 16 30-mer peptides overlapping by 15 amino acids. Peptides were synthesized by solid phase technique on an automated multiple peptide synthesizer (Abimed AMS 422, Langenfeld, Germany), and analysed by reverse phase HPLC. The lyophilized peptides were dissolved in 50 μl of DMSO, diluted in PBS to a final concentration of 2.5 mg/ml. The HPV16 E2 C terminal ($E2_{280-365}$) protein and HPV16 E7 protein were produced according to previously described procedures (Franken et al., 2000) Memory Response Mix (MRM), consisting of a mixture of tetanus toxoid (0.75 LF/ml final concentration; National Institute of Public Health and Environment, Bilthoven, The Netherlands), *Mycobacterium tuberculosis* sonicate (2.5 μg/ml; generously donated by Dr. P. Klatser, Royal Tropical institute, Amsterdam, The Netherlands) and *Candida albicans* (0.005%, HAL Allergenen Lab, Haarlem, The Netherlands), was used to confirm the capacity of PBMC to proliferate and produce cytokine in response to common recall antigens.

HLA-DR-peptide Binding Assay

Binding of peptides to HLA-DR was measured as reported previously (van der Burg et al., 1999). Briefly, as a source of DR molecules B-LCL homozygous for DR were used: LG2.1 (DRB*0101, DR1), IWB (DRB1*0201, DR2), HAR (DRB*0301, DR3), and BSM (DRB*0401, DR4). DR molecules were purified by affinity chromatography and the purity confirmed by SDS-PAGE. The analysis of peptide binding to purified DR molecules was performed using N-terminally fluorescence-labelled standard peptides. As standard peptide in the binding assays $HA_{308-319}$ (PKYVKQNTLKLAT, DR1 and DR2), (SEQ. ID. NO. 4), hsp65 3-13 (KTIAYDEEARR, DR3) (SEQ. ID. NO. 5) or $HA_{308-319}$ Y→F (PKFVKQNTLKLAT) (SEQ. ID. NO. 6) was used.

Short-term T Cell Proliferation Assay

Immunogenicity of individual HPV16 E2 peptides was determined by short term proliferation assays of healthy donor PBMC with HPV16-E2 peptides, according to previously described procedures (van der Burg et al. 1999). Briefly, freshly isolated PBMC were seeded at a density of $1.5 \times 10^5$ cells/well in a 96-well U-bottom plate (Costar, Cambridge, Mass.) in 200 μl of IMDM (Iscove's Modified Dulbecco's Medium, Bio Whittaker, Verviers, Belgium) supplemented with 10% autologous serum (10% FCS was used for CBC cultures). HPV16-E2 peptides were added at a concentration of 10 μg/ml.

Medium alone was taken along as negative control; phytohemagglutinine (PHA, 0.5 μg/ml) served as a positive control. For each peptide 8 parallel micro-cultures were initiated; each donor was tested twice. Peptide-specific proliferation was measured at day 6 by $^3$H-thymidine incorporation. Peptides were scored positive, when—in both assays—the proliferation of >50% of the test wells exceeded the mean proliferation+3×SD of the control wells, and the stimulation index (SI) of all test wells over medium control wells was higher than 3.

Generation and Analysis of Long-term HPV16-E2 Specific Th-cultures

Long-term HPV16 E2-specific T-cell cultures and Th-clones were established according to previously described procedures (van der Burg et al. 1999). Briefly, PBMC from healthy HLA-typed donors were stimulated in vitro with the following HPV16 E2 peptides ($E2_{271-300}$+$E2_{286-315}$; $E2_{301-330}$+$E2_{316-345}$; $E2_{331-365}$). $15 \times 10^6$ PBMC were seeded in 25cm$^2$ culture flasks (Nalge Nunc, USA) in 6 ml IMDM supplemented with 10% autologous serum. Peptides were added at a concentration of 5 μg/ml. At day 7, $15 \times 10^6$ PBMC were added, together with fresh medium and peptides. At day 14 and 21 viable T cells were harvested from the cultures, counted and restimulated with an equal amount of autologous irradiated PBMC and peptide (5 μg/ml). T-cell growth factor (Biotest, Dreieich, Germany) was added 2 days after restimulation at a final concentration of 10%. The T-cell cultures were tested for peptide recognition by proliferation assay at day 28. Peptide-specific T-cell cultures were cloned by limiting dilution and T-cell clones were subsequently tested for the recognition of E2-peptide and -protein-pulsed APC.

Specificity of the Th clones was analysed as described previously (Van der Burg et al. 1999). Notably, in proliferation assays in which Th-clones were tested for protein recognition, autologous monocytes were used as APC. For measurement of proliferation, cultures were pulsed with 0.5 Ci [$^3$H] thymidine (5 μCi/mM, Amersham, UK) per well for 18 hours. Plates were harvested with a Micro cell Harvester (Skatron, Norway). Filters were packed in plastic covers containing 10 ml of scintillation fluid and subsequently counted on a 1205 Betaplate counter (Wallac, Turku, Finland). HLA-class II blocking experiments were performed using murine monoclonal antibodies: anti-DQ SPV. L3, anti-DR B8. 11.2, and anti-DP B7/21. Supernatants of the proliferation assays were harvested 24 hrs after incubation and analysed for the presence of IFN-γ by ELISA (van der Burg et al., 1999).

Detection of Memory Th-cells by ELISPOT

Memory cells (CD45RO$^+$) were isolated freshly from buffycoats by MACS after incubation with CD45RO microbeads (cat. no. 460-01, Miltenyi Biotec, Germany). The purity of the obtained CD45RO+ fraction was >95% as determined by floweytometry after surface staining for CD45RO and CD45RA (CD45RA-FITC, cat. no. 347723, CD45RO-PE, cat. no. 347967, Becton Dickinson Biosciences, USA). CD45RO+ cells were seeded at a density of $10^6$ cells/well in a 24-wells plate (Costar) in 1 ml of IMDM supplemented with 10% FCS. $10^6$ irradiated autologous cells were added to each well as APC. The responder cells were incubated with either medium alone, pools of HPV16-E2 peptides at 5 μg/ml/peptide, MRM 1:50 dilution or pools of Influenza Matrix peptides (positive controls) and cultured for 11 days in order to improve the detection of antigenspecific cells (Mc Cutcheon et al. 1997). The cells were then harvested, washed and seeded in 4 replicate wells at a density of $5 \times 10^4$ cells/well of a Multiscreen 96-well plate (Millipore, Etten-Leur, The Netherlands) coated with a IFN-γ catching antibody.

Per well, $10^5$ irradiated autologous PBMC were added as APC together with 5 μg/ml peptide. ELISPOT analysis was further performed according to the instructions of the manufacturer (Mabtech AB, Natcha, Sweden). Analysis of the number of spots was done with a fully automated computer-assisted-video-imaging analysis system (Carl Zeiss Vision).

Intracellular Cytokine Staining (ICS) of Memory T-cells

Autologous monocytes were isolated from PBMC by adherence to a flat-bottom 48-wells plate during 2 hours in X-vivo 15 medium (Bio Whittaker, Verviers, Belgium) at 37° C., and then used as APC. CD45RO+ cells were stimulated for 11 days with peptide, then harvested, washed and suspended in IMDM+0.1% BSA at a concentration of $1.5 \times 10^6$ cells/ml. 200l of cell suspension was added to the monocytes+200 μl of 10 μg/ml HPV16-E2 peptide (stimulated) or 200 μl of medium (non-stimulated control). After 1 hour of incubation at 37° C., 800 μl of IMDM+10% FCS+ 12.5 μg/ml Brefeldin A (Sigma) was added and cells were incubated for another 5 hours. The cells were then harvested, transferred into a V-bottom 96-wells plate, washed twice with ice-cold PBS and fixed with 50 gel paraformaldehyde 4% for 4 minutes on ice. Following fixation, the cells were washed once with cold PBS and once with PBS/NaAz 0.2%/BSA 0.5%/Saponin 0.1%.

This was followed by an incubation in 50 μl PBS/NaAz 0.2%/B SA 0.5%/Saponin 0.1%/FCS 10% for 10 minutes on ice. Cells were washed twice with PBS/NaAz 0.2%/BSA 0.5%/Saponin 0.1% and supernatant was removed before 25 μl of PBS/NaAz 0.2%/BSA 0.5%/Saponin 0.1% containing 1 μl FITC-labelled mouse-anti-human IFN-γ (0.5 g/ml, BD Pharmingen, cat. no. 554551) 2 μl PE-labelled anti-CD4 (BD Bioscience, cat. no. 345769), and 2 μl PerCP-labelled anti-CD8 (BD Bioscience cat. no. 347314) was added. Following 30 minutes of incubation at 4° C., the cells were washed, suspended in 100 μl paraformaldehyde and analysed by flowcytometry.

Homology Search in Protein Database

The search for sequence homology of the overlapping HPV16 E2 peptides in a protein database (SwissProt) was performed using standard Basic Local Alignment Tool (BLAST: www.ncbi.nlm.gov/blast/blastcgi). Statistical significance threshold (EXPECT) was 10 (Altschul et al., 1997). Reported matches with >60% aminoacid homology with HPV16 E2 peptides were included.

Results

High Reactivity of Healthy Donor PBMC Against HPV16 E2-derived Peptides.

We examined the proliferative responses of healthy donor PBMC against HPV16 E2 protein by using an array of overlapping 30-mer peptides covering the entire E2 sequence. Incubation of freshly isolated PBMC of 8 HLA-typed donors with each of the 23 E2-derived 30-mer peptides showed that 4 out of 8 donors reacted to 2 or more of the peptides. The observed E2 peptide-specific proliferative responses were remarkably strong (Table IV). In all cases more than 75% of the parallel micro cultures reacted against the stimulating peptide. For instance, in two independent experiments we found the peptide-specific proliferation of donor # 8 against peptides $E2_{31-60}$, $E2_{46-75}$, $E2_{91-120}$, $E2_{151-180}$, $E2_{271-300}$ and $E2_{286-315}$ to exceeded background proliferation in 75-94% of all eight parallel micro cultures tested. This points at the presence of a very high frequency of E2-specific T-cells in the PBMC isolates. In particular, PBMC of donors # 3, 5 and 8 displayed strong responses with a broad specificity. Please note that the 30-mer peptides have a 15 amino acid overlap with their neighboring peptides. Consequently, responses against adjacent peptides (e.g. donor # 3, $E2_{31-60}$ and $E2_{46-75}$) most likely involve the same epitope, whereas responses against non-adjacent peptides are directed against distinct epitopes.

Not only the frequency of responding cultures but also the magnitude of the proliferative responses were remarkably high. The peptide-specific proliferation of several cultures from donors # 3, 5 and 8 exceeded background with mean stimulation indices ranging from 9.2-16.5 and, as such, are comparable to responses found against the tetanus toxoid antigen in several of the donors (# 3, 4,5 and 7; SI ranging from 13.3-25 ; see Table IV). These stimulation indices clearly exceed the threshold (SI≥3) that is commonly used for the detection of memory T cell responses (Bermas et al., 1997).

Please note that responses against tetanus toxoid are considerably higher in some of the other donors (SI≥100 in donors # 3 and 6), but that these strong values most likely represent very broad responses against multiple epitopes comprised by an entire antigen, rather than against a single 30-mer E2-peptide. Taken together, our data indicate that the T cell repertoire of healthy donors can contain particularly high frequencies of T-cells specific for the HPV16 E2 antigen resulting in vigorous proliferative responses, and suggest that these responses may reflect T-cell memory.

| | D1 [1] | D2 | D3 | D4 | D5 | D6 | D7 | D8 |
|---|---|---|---|---|---|---|---|---|
| Immunogenicity of HPV16 E2 derived peptides. EMI32.1 Immunogenicity of HPV16 E2 derived peptides. | | | | | | | | |
| $E2_{1-30}$ [2] | | | | | | | | |
| $E2_{16-45}$ | | | | | | | | |
| $E2_{31-60}$ | | | 81% (8.8)[3] | | | | | 88% (8.6) |
| $E2_{46-75}$ | | | 88% (5.5) | | 81% (6.8) | | | 94% (6.5) |
| $E2_{61-90}$ | | | | | | | | |
| $E2_{76-105}$ | | | | | | | | |
| $E2_{91-120}$ | | | | | 94% (4.8) | | | 75% (4.0) |
| $E2_{106-135}$ | | | | | | | | |
| $E2_{121-150}$ | | | | | | | | |
| $E2_{136-165}$ | | | | | | | | |
| $E2_{151-180}$ | | | 81% (6.4) | | | | | 81% (4.1) |
| $E2_{166-195}$ | | | 94% (16.5) | | 81% (10.6) | | | |
| $E2_{181-210}$ | | | | | | | | |
| $E2_{196-225}$ | | | | | | | | |
| $E2_{211-240}$ | | | | | | | | |
| $E2_{226-255}$ | | | | | | | | |

Immunogenicity of HPV16 E2 derived peptides. EMI32.1
Immunogenicity of HPV16 E2 derived peptides.

| | D1 [1] | D2 | D3 | D4 | D5 | D6 | D7 | D8 |
|---|---|---|---|---|---|---|---|---|
| $E2_{241-270}$ | | | | | | | | |
| $E2_{256-285}$ | | | | | | | | |
| $E2_{271-300}$ | | | | | | | | | 88% (4.8) |
| $E2_{286-315}$ | | | 88% (16.2) | | | | | 94% (9.2) |
| $E2_{301-330}$ | | | | | | | | |
| $E2_{316-345}$ | | | | | | | 94% (4.7) | |
| $E2_{331-365}$ | | | 100% (11.4) | | | | 75% (4.1) | |
| TT | 100% (29.1) | 100% (56.5) | 100% (25) | 100% (16.4) | 100% (23.5) | 100% (139) | 100% (13.3) | 100% (59) |

[1] D: Donor, Eight different healthy blood donors were tested.
[2] HPV16 E2 peptides are indicated by the first and last amino acid. TT is the common recall antigen tetanus toxoid.
[3] Peptides were scored positive, when-in both assays-the proliferation of >50% of the test wells exceeded the mean proliferation +3 * SD of the control wells, and the stimulation index (SI) of the positive test wells over medium control wells was higher than 3. Only positive scores are depicted as the mean percentage of wells exceeding medium control + 3 * SD from the percentages found in both assays. Between brackets the mean stimulation index of all test wells of both assays.

HPV16 E2-specific Th Cultures Recognize Naturally Processed Epitopes

The proliferation data pointed at the existence of multiple immunogenic Th-epitopes within HPV16 E2. We performed a more detailed analysis of the nature and specificity of such responses, thereby focussing on the N-terminal and C-terminal region which our data (Table IV) revealed to comprise several highly immunogenic peptides. The overlapping peptides comprised in this C-terminal region ($E2_{271-300}$, $E2_{286-315}$; $E2_{301-330}$; $E2_{316-345}$; $E2_{331-365}$) were tested for their capacity to bind to HLA-DR molecules. Each of the five peptides showed intermediate to strong binding to two or more of the common HLA-DR molecules tested (Table V), which supports the notion that these peptides can indeed represent class II MHC-restricted Th-epitopes.

TABLE V

Binding affinity of HPV16-E2 derived peptides to different HLA-DR types

| Amino acid sequence | HPV16-E2 | DR1 | DR2 | DR3 | DR4 |
|---|---|---|---|---|---|
| FNSSHKGRINCNSNTTPIVHLKGDANTLKC (SEQ. ID. NO. 8) | 271-300 | 22 | 65 | 37 | >70 |
| TPIVHLKGDANTLKCLRYRFKKHCTLYTAV (SEQ. ID. NO. 9) | 286-315 | 8 | 68 | 20 | >70 |
| LRYRFKKHCTLYTAVSSTWHWTGHNVKHKS (SEQ. ID. NO. 10) | 301-330 | 6 | 8 | >70 | 10 |
| SSTWHWTGHNVKHKSAIVTLTYDSEWQRDQ (SEQ. ID. NO. 11) | 316-345 | 6 | 55 | 30 | >70 |
| AIVTLTYDSEWQRDQFLSQVKIPKTITVSTGFMSI (SEQ. ID. NO. 12) | 331-365 | 8 | 20 | 10 | 15 |

Binding affinity of each peptide is expressed as the $IC_{50}$ value: this is the peptide concentration (µM) at which binding of the standard fluorescence labeled peptide is reduced to 50% of its maximal value >70 represents undetectable binding.

Subsequently, long-term E2-specific Th cultures were generated through stimulation of PBMC from HLA-typed healthy blood donors at weekly intervals with either peptides $E2_{271-300}$ and $E2_{286-315}$, peptides $E2_{301-330}$ and $E23_{316-345}$, or with peptide $E2_{331-365}$ or with peptide $E2_{46-75}$. PBMC from 2 donors showed strong peptide-specific proliferative responses against one or more of the stimulating peptides (data not shown). Through cloning via limiting dilution of these cultures, we succeeded in the isolation of stable T cell clones, uniformly displaying a $CD4^+CD8^-$ phenotype, against six distinct peptideepitopes. Two of these Th clones were established from HLA-DR15 (2)-,-DQ6 (1)-PBMC stimulated with $E2_{301-330}$ and $E2_{316-345}$. Although both Th-clones recognized $E2_{301-830}$, in depth analysis of the specificity of these Th clones revealed that they recognized distinct, yet overlapping, sequences, restricted by different class II HLA molecules. One of the clones recognized peptide $E2_{316-330}$ in the context of HLA-DR15 (2), whereas the other clone was specific for peptide $E2_{311-325}$ in the context of HLA-DQ6 (1) (FIGS. 5a-5d and, 6a-6d). The two other Th-clones were similarly related, in that one recognized peptide $E2_{346-355}$ in the context of DR15 (2), whereas the other reacted against $E2_{351-36}$ in a DR1-restricted manner (FIGS. 7a-7d and, 8a-8c). Notably, these data are in correspondence with the peptide binding data in Table V, in that longer variants of these DR15(2) and DR1restricted epitopes were indeed found to bind to the restricting HLA molecules (binding assay not available for HLA-DQ6). In addition, two clones were found to react to peptide $E2_{46\ 75}$, one reacted against peptide $E2_{51-70}$ in a HLA-DR4 restricted manner and the other clone reacted against peptide $E2_{61-75}$. (FIGS. 15a-15c) Further evidence that the four E2 peptides identified represent physiologically relevant Th epitopes is provided by the fact that the E2-specific Th clones did not only respond against peptide-loaded APC, but also specifically responded against APC that were pulsed with the E2 protein (FIGS. 5a-5d and, 8a-8c). Because in the latter case presentation of the peptide epitopes depends on uptake and processing of the E2 antigen, and not merely on exogenous loading of class II molecules at the APC cell surface, these data provide definite proof that the four E2 peptides recognized by our Th clones correspond to naturally processed epitopes. Finally, all four Th-clones produced IFN-γ upon antigenic stimulation, which is indicative of a Th-type 1 cytokine profile. Taken together our data show that the T cell repertoire of healthy individuals harbors IFN-γ -secreting E2specific $CD4^+$ Th cells (FIGS. 5a-5d and, 8a-8c).

Detection of HPV16 E2 Specific Memory Th-cells in Healthy Individuals

The strikingly frequent detection of HPV16 E2-specific Th immunity in healthy individuals, as described in the first paragraph, prompted us to analyse whether the underlying T cell repertoire would represent immunological memory as a the result of previous encounter with antigen, or whether it would primarily consist of particularly abundant naive T cell precursors specific for this antigen. In view of the high incidence of, generally transient, genital HPV infections in young sexually active individuals (Karlsson et al., 1995; Koutsky et al., 1997; Ho et al., 1998), as well as the prominent expression of E2 during HPV infection, it seems conceivable that T cell memory against E2 is to be found in healthy subjects. We examined the nature of the HPV16 E2-specific immunity detected by us through analysis of the E2-specific reactivity of the CD45RO+ fraction of healthy donor PBMC, which contains antigen-experienced T-cells but is devoid of their naive counterparts (Young et al., 1997). Because we found the T cell repertoire of healthy donors to contain IFNγ-producing Th cells (FIGS. 5a-5d and, 8a-8c), we measured the antigen-specific T cell responses through IFNγ ELISPOT. We first analysed the reactivity of CD45RO+ T cells of two healthy donors while focusing our attention on a selection of E2 peptides which on basis of our previous experiments (Table IV) appear to be localized in the most immunogenic regions of HPV16 E2.

Interestingly, these CD45RO+ PBMC were found to respond against multiple E2 peptides (FIGS. 9a, 9b), supporting the notion that healthy subjects can display HPV16E2-specific T cell memory. We confirmed that the responding IFNγ -producing cells belonged to the CD4+ Th cell subset by employing IFNγ intracellular cytokine staining instead of ELISPOT as a readout (not shown). A broader survey of E2-specific reactivity against the full array of peptides, using CD45RO+ PBMC from 8 additional healthy donors, revealed that 4 of these PBMC isolates responded against one or more of the HPV16 E2 peptides (FIGS. 9c-9f and not shown). Taken together, our data reveal the presence of CD45RO+ memory-type, IFNγ secreting Th cells reactive against HPV16 E2 peptides in approximately half of the healthy donors tested. Notably, the incidence by which these responses are detected is very similar to that of the strongest subset of proliferative responses found in total PBMC (Table IV), implicating that also these responses are likely to represent reactivity by memory T cells rather than by in vitro primed naive T cells.

Cross-reactivity of HPV16 E2 Specific Th-clones with Peptide Sequences of Other HPV Types Due to the common nature of HPV infections, a majority of the human population is likely to encounter multiple HPV types (Thomas et al. 2000; Koutsky et al. 1997). Furthermore, the protein sequences of the viral gene products are conserved to considerable extend between HPV types. It is therefore possible that at least a fraction of the T cell repertoire induced by a previous encounter with a given type of HPV could cross-react, and therefore cross-protect, during subsequent infection with other HPV types. Alignment of the sequence of the HPV16 E2 protein with that of various other HPV types revealed that it is most prominently conserved with that of other high risk types. Although this conservation is somewhat less conspicuous when the HPV16 E2 sequence is compared to that of low risk or common types it is evident that in all cases maximal conservation is confined to certain regions within the E2 sequence. In particular, three areas of HPV16E2 share homology with E2 of other HPV types: the N-terminal portions $E2_{31-120}$ and $E2_{151-195}$ as well as the C-terminal portion $E2_{271-365}$. These regions co-localise with the major functional domains of E2, in that the N-terminal domain harbours the transcriptional activation functions of this protein whereas the C-terminal portion mediates its sequence-specific DNA-binding properties. The intervening sequences ranging from residues 210 to 270 constitute the so-called hingeregion connecting the two key functional domains, which is poorly conserved between HPV types. Interestingly, our analyses of E2-specific responses in short-term proliferation assays have revealed that the most immunogenic peptides are clustered in the two conserved domains of the HPV16 E2 sequence (see Table IV). In view of these considerations, we tested whether our established Th clones, raised against epitopes derived from the C-terminal part of the HPV16 E2 sequence (FIGS. 5a-5d and, 8a-8c), would be capable of cross reacting with E2 peptides of a number of other HPV types that shared maximal homology with HPV16 with respect to this particular E2 sequence. Indeed, the DQ6 restricted $E2_{311-325}$-specific Th-clone showed strong recognition of the corresponding peptides of HPV types 26,31,35 and 45 (not shown). The amino acid homology within this epitope varies from 73 to 87% (identical or amino acids with similar physico-chemical properties). Our other Th clones did not reveal considerable cross-reactivity for highly homologous E2 peptides of other HPV types (not shown).

These data indicate that part of the HPV16 E2-reactive Th memory detected in our assays may relate to encounter of HPV types other than HPV16, but also suggest that the majority of this immune repertoire was most likely established through encounter with HPV16 itself.

Example 3

Material and Methods
Subjects and Controls

PBMC of anonymous healthy blood bank donors (D) were obtained. Since these donors are anonymous, no additional data is available. However, donors with a known recent history of infection, including abnormal pap-smear, were, as part of normal regulations, discouraged to donate blood.

The study of subjects (S; Table II) with CIN or cervical carcinoma in this paper was nested in the "CIRCLE study" that investigates cellular immunity against HPV16 infected cervical lesions. Women presenting with histologically proven CIN III or cervical carcinoma at the department of gynecology of the Leiden University Medical Center (LUMC) were, after informed consent, enrolled in this study. The study design was approved by the ethics committee of the LUMC. Blood was drawn at day of treatment. Subjects with CIN III were treated by LEEP or cold knife conization. In case of stage IB-IIA a radical hysterectomy was performed. Subjects were typed for HPV16 using HPV16-specific primers on DNA isolated from paraffin-embedded sections of biopsies or surgical resection specimens (Claas et al., 1989). Since HPV-specific Thelper response were expected to be found in subjects with progressive disease (de Gruijl et al., 1998), we chose to analyse subjects with stage IB cervical cancer.

Antigens.

The peptides used spanning the E6 protein consisted of 15 overlapping 22-mer peptides and are indicated by their first and last amino acid in the protein (e.g. 1 22,11-32,2142,31-52,41-62,51-72,61-82,71-92 and so forth, the last peptide consists of amino acid 137-158). Peptides were synthesized and dissolved as described previously (van der Burg et al., 1999).

Memory Response Mix (MRM): A mixture of tetanus toxoid (1 LF/ml; National Institute of Public Health and the Environment, Bilthoven, The Netherlands) and *Mycobacterium tuberculosis* sonicate (2.5 µg/ml; generously donated by Dr. P. Klatser, Royal Tropical Institute, The Netherlands) was used to control the capacity of PBMC to proliferate in response to typical recall antigens.

Analysis of Antigen-specific T-cells by ELISPOT.

PBMC were seeded at a density of $2\times10^6$ cells/well of a 24 well plate (Costar, Cambridge, Mass.) in 1ml of ISCOVE's medium (Gibco) enriched with 10% FCS, in the presence or absence of 5) μg/ml of indicated E6-derived 22-mer peptide. As positive control PBMC were cultured in the presence of indicated pools of influenza A/PR/8/34 MI protein derived peptides consisting of 4 overlapping 30 amino acid long peptides in each pool.

In case CD45RO+ cells were used the CD45RO+ cells were seeded at a density of $10^6$ cells/well in a 24-wells plate (Costar) in 1 ml of IMDM supplemented with 10% FCS together with indicated single or pools of peptides at a concentration of 10 μg/ml/peptide.

Following 4 days of incubation at 37° C., PBMC were harvested, washed and seeded in four to six replicate wells at a density of $10^5$ cells/well of a Multiscreen 96-well plate (Millipore, Etten-Leur, The Netherlands) coated with a IFNγ catching antibody (Mabtech AB, Nacha, Sweden). The ELISPOT was further performed according to the instructions of the manufacturer (Mabtech). The number of spots were analysed with a fully automated computer assisted video imaging analysis system (Carl Zeiss Vision).

Specific spots were calculated by subtracting the mean number of spots+2×SD of the medium only control from the mean number of spots of experimental wells. Antigenspecific T-cell frequencies were considered to be increased compared to non-responders when T-cell frequencies were=1/10,000 PBMC.

Isolation of the CD45RO+ Memory Fraction of PBMC

Memory cells (CD45RO+) were isolated freshly from buffycoats by MACS after incubation with CD45RO microbeads (cat. no. 460-01, Miltenyi Biotec, Germany) according to the instructions of the manufacturer. The purity of the obtained CD45RO+ fraction was >95% as determined by floweytometry after surface staining for CD45RO and CD45RA (CD45RA-FITC, cat. no. 347723, CD45RO-PE, cat. no. 347967, Becton Dickinson Biosciences, USA).

Results

In view of the high incidence of, generally transient, genital HPV infections in young sexually active individuals (Karlsson et al., 1995; Koutsky et al., 1997; Ho et al., 1998), as well as the prominent expression of HPV16 E2-specific immunity (see example 2) in about half of the healthy subjects tested, we studied the natural, in vivo induced, HPV16 E6-specific response in the human population by means of the 4-day IFNγ -ELISPOT assay. This assay detects only memory T helper-cells, which upon stimulation will secrete IFNγ whereas their naive counterparts will not (see example 1 and 2 and references therein). A survey of E6-specific reactivity against the full array of peptides present in PBMC from 18 healthy blood donors, revealed that 11 of these 18 (>60%) PBMC isolates responded against one or more of the HPV16 E6 peptides (Table VIa).

The majority of the responses were found at the C-terminal end of E6 ($E6_{81-158}$).

Furthermore, all healthy donors reacted against the common recall antigen influenza matrix 1 protein. The frequency of both influenza MI and HPV16 E6-specific T-helper cells were of comparable magnitude. Interestingly, a similar survey in HPV16+ patients revealed that only 3/12 (25%) reacted against HPV16 E6 peptides indicating that the E6 response found in healthy subjects is protective against disease.

TABLE VI

Detection of HPV16 E6-specific T-helper reactivity in healthy donor PBMC.

| Donor[1] | 1-22[2] | 11-32 | 21-42 | 31-52 | 41-62 | 51-72 | 61-82 | 71-92 | 81-102 | 91-112 |
|---|---|---|---|---|---|---|---|---|---|---|
| 1 | <1 | <1 | <1 | <1 | <1 | <1 | <1 | <1 | <1 | <1 |
| 2 | <1 | <1 | <1 | <1 | <1 | <1 | <1 | <1 | <1 | <1 |
| 3 | <1 | 4 | <1 | 3 | <1 | <1 | <1 | <1 | <1 | <1 |
| 4 | <1 | <1 | <1 | 10 | <1 | <1 | <1 | <1 | <1 | <1 |
| 5 | <1 | 5 | 1 | 1 | 2 | 9 | 5 | 7 | 6 | 10 |
| 6 | 3 | 34 | <1 | 9 | <1 | <1 | 2 | <1 | 11 | 14 |
| 7 | <1 | 2 | 1 | <1 | <1 | <1 | <1 | <1 | 2 | 14 |
| 8 | 4 | 4 | <1 | <1 | 9 | <1 | <1 | <1 | 12 | 14 |
| 9 | 2 | <1 | 7 | 3 | <1 | <1 | 4 | <1 | <1 | 3 |
| 10 | <1 | <1 | <1 | <1 | <1 | <1 | <1 | <1 | <1 | <1 |
| 11 | 2 | <1 | <1 | 2 | <1 | <1 | 41 | 7 | 3 | 4 |
| 12 | <1 | <1 | <1 | <1 | <1 | <1 | <1 | <1 | 1 | <1 |
| 13 | <1 | <1 | <1 | <1 | <1 | <1 | <1 | <1 | <1 | <1 |
| 14 | 5 | 5 | <1 | 10 | 5 | <1 | 2 | 20 | 12 | 5 |
| 15 | 18 | 16 | 4 | 15 | 2 | 1 | <1 | 3 | 12 | 21 |
| 16 | <1 | <1 | <1 | <1 | <1 | <1 | <1 | <1 | <1 | <1 |
| 17 | <1 | <1 | <1 | <1 | <1 | <1 | <1 | <1 | <1 | <1 |
| 18 | <1 | <1 | <1 | <1 | 4 | <1 | <1 | <1 | 2 | <1 |

| Donor[1] | 101-122 | 111-132 | 121-142 | 131-152 | 137-158 | M1P1 | M1P2 | M1P3 | M1P4 |
|---|---|---|---|---|---|---|---|---|---|
| 1 | <1 | <1 | <1 | <1 | <1 | <1 | 16 | <1 | <1 |
| 2 | <1 | <1 | <1 | <1 | 4 | 2 | 26 | 12 | 7 |
| 3 | <1 | 3 | 8 | 18 | 4 | 30 | 7 | 19 | <1 |
| 4 | <1 | <1 | <1 | <1 | <1 | 22 | 15 | 14 | 10 |
| 5 | 2 | 8 | 5 | 8 | 1 | 7 | 10 | 12 | 37 |
| 6 | 6 | 12 | 10 | <1 | 6 | <1 | 33 | 41 | 5 |
| 7 | <1 | <1 | 1 | 3 | 14 | 6 | 21 | 57 | 28 |
| 8 | 3 | 6 | 7 | 3 | <1 | 27 | 38 | 34 | 16 |
| 9 | <1 | <1 | 3 | <1 | <1 | 22 | 10 | 14 | 4 |
| 10 | <1 | <1 | 7 | <1 | <1 | 13 | 23 | 19 | 11 |
| 11 | 2 | 15 | 10 | 27 | 17 | 33 | 28 | 24 | 52 |
| 12 | <1 | <1 | 14 | 15 | <1 | 5 | 10 | 12 | <1 |
| 13 | <1 | 1 | <1 | <1 | <1 | <1 | <1 | 1 | 21 |

TABLE VI-continued

Detection of HPV16 E6-specific T-helper reactivity in healthy donor PBMC.

| 14 | 28 | 18 | 37 | 40 | 2 | 12 | 42 | 28 | 45 |
| 15 | 8 | 11 | 8 | <1 | <1 | 52 | 68 | 64 | 5 |
| 16 | <1 | <1 | <1 | <1 | <1 | 39 | 66 | 49 | 48 |
| 17 | <1 | <1 | <1 | <1 | <1 | 4 | 3 | <1 | 66 |
| 18 | <1 | 11 | 1 | 1 | <1 | <1 | 1 | 10 | <1 |

[1] 18 different healthy blood donors were tested.
[2] First and last amino acid number of HPV16 E6-derived peptides are indicated. M1P1-M1P4 are the four different pools of 4, by 15 residues overlapping, 30-amino acid long peptides derived from influenza A matrix 1 protein (inf A/PR/8/34).
[3] Indicated are the number of specific spots per 100,000 PBMC. Specific spots are calculated by subtracting the mean number of spots + 2xSD of the medium control from the mean number of spots after stimulation with peptide. Numbers in bold indicate T-cell frequencies ≥1/10,000

TABLE VIb

Detection of HPV16 E6-specific T-helper reactivity in HPV16+ patients.

| patient | 1-22 | 11-32 | 21-42 | 31-52 | 41-62 | 51-72 | 61-82 | 71-92 | 81-102 | 91-112 |
|---|---|---|---|---|---|---|---|---|---|---|
| C40 | <1 | <1 | <1 | <1 | <1 | <1 | <1 | <1 | <1 | <1 |
| C41 | <1 | <1 | <1 | <1 | <1 | <1 | <1 | <1 | <1 | <1 |
| C43 | <1 | <1 | <1 | <1 | <1 | <1 | <1 | <1 | <1 | <1 |
| C47 | <1 | <1 | <1 | 28 | <1 | <1 | <1 | <1 | <1 | <1 |
| C67 | <1 | <1 | <1 | <1 | <1 | <1 | <1 | <1 | <1 | <1 |
| C58 | <1 | <1 | <1 | <1 | <1 | <1 | <1 | <1 | <1 | <1 |
| C63 | <1 | <1 | <1 | <1 | <1 | <1 | <1 | <1 | <1 | <1 |
| C66 | <1 | <1 | <1 | <1 | <1 | 11 | <1 | <1 | <1 | <1 |
| C73 | <1 | <1 | <1 | <1 | 2 | 1 | <1 | 3 | 4 | 5 |
| C75 | <1 | <1 | <1 | <1 | <1 | <1 | <1 | <1 | <1 | <1 |
| C80 | <1 | <1 | <1 | <1 | <1 | <1 | 1 | 1 | 2 | <1 |
| C91 | <1 | <1 | <1 | <1 | <1 | <1 | <1 | <1 | <1 | <1 |

| patient | 101-122 | 111-132 | 121-142 | 131-152 | 137-158 | M1P1 | M1 P2 | M1P3 | M1P4 |
|---|---|---|---|---|---|---|---|---|---|
| C40 | <1 | 1 | <1 | <1 | <1 | <1 | <1 | <1 | 3 |
| C41 | 2 | <1 | <1 | <1 | <1 | <1 | <1 | 10 | <1 |
| C43 | <1 | <1 | <1 | <1 | <1 | <1 | <1 | 4 | <1 |
| C47 | <1 | <1 | <1 | 13 | <1 | <1 | <1 | <1 | <1 |
| C67 | 2 | <1 | <1 | 22 | <1 | <1 | 2 | 62 | 30 |
| C58 | <1 | <1 | <1 | <1 | <1 | <1 | <1 | <1 | <1 |
| C63 | <1 | <1 | <1 | <1 | <1 | <1 | 1 | <1 | <1 |
| C66 | <1 | <1 | <1 | <1 | <1 | 31 | <1 | 13 | <1 |
| C73 | <1 | 8 | 7 | 7 | 9 | 5 | 2 | 4 | 2 |
| C75 | <1 | <1 | <1 | <1 | <1 | <1 | <1 | 15 | <1 |
| C80 | 1 | 1 | <1 | 2 | <1 | 7 | 2 | 7 | 1 |
| C91 | <1 | <1 | <1 | <1 | <1 | 3 | 2 | <1 | <1 |

To confirm our observation that HPV16-specific memory T-cells were present in a large fraction of the human population we isolated the specific CD45RO+, memory fraction of PBMC before they were subjected to stimulation with HPV16 E6 peptides. After a 4 days of stimulation a clear response to HPV16 E6 could be detected. Taken together, our data reveal the presence of CD45RO+ memory-type, IFNγ secreting T helper cells reactive against both HPV16 E6 peptides in approximately half of the healthy donors tested.

Furthermore, PBMC of two different HLA-DR1 positive blood donors were stimulated with a pool of two long 35-mer peptides that together covered E6 109-158. PBMC of these donors proliferated specifically against peptide E6 121-142 and peptide E6 127158 as well as E6protein. A CD4+ T-helper clone derived from one of these bulks was analysed further and specifically proliferated and produced IFNγ when stimulated with HPV16 E6 peptide and HPV16 E6 protein in a HLA-DR1 restricted manner (FIGS. 16a-16d).

Conclusions

Through analysis of the IFNγ -responses in PBMC cultures from healthy subjects against the HPV16 E6 antigen we have demonstrated that this protein contains highly immunogenic peptide sequences to which strong T-cell reactivity is detected in approximately half of these donors. Subsequent testing of the CD45RO+ memory fraction of healthy donor PBMC revealed that these HPV16 E6-specific IFNγ -secreting CD4+ T cells were present in the T-cell memory fraction of PBMC and thus have been primed in vivo upon encounter with HPV. A similar survey demonstrated that HPV16 E6-specific IFNγ secreting T-cells were almost absent in HPV16+ patients. Taken together, our data demonstrate that the T-cell repertoire of a majority of the healthy subjects contains particularly high frequencies of memory type 1 cytokine producing T helper cells reactive against the HPV16 E6 antigen and indicates that these are protective against disease.

Importantly, we have not found any previous report concerning the presence of memory T-cell responses against E2 and E6 or any of the other non-structural HPV16 proteins in healthy individuals. In fact, healthy individuals served in many cases as negative control for the culture conditions used. We have now shown, in two independent studies (example 2 and example 3), that healthy donor derived PBMC contain HPV16-specific T-helper cells. The majority of the T-helper responses are directed against specific regions in E2 and E6. The presence of these memory type T-helper cells show that these individuals have encountered HPV16 infection, responded to it via the cellular T-cell arm of the immune system and cleared the infection. This implies that the T-cell response to these antigens is a part of the protective response to HPV infection.

Induction or boosting of these type of responses can therefore be a powerful tool in the protection against HPV induced diseases.

Example 4

Material & Methods

Male C57/B16 mice (n=8 per group) were vaccinated with either 10 μg of the exact E1A-derived CTL epitope (SGPSNTPPEI) (SEQ. ID. NO. 1) or with 30 μg of the HPLC-purified 32-amino acid long peptide RECNSSTD-SCDSGPSNTPPEIHPVVRLCPIKP (SEQ. NO. ID. 2) containing this CTL epitope. Peptides were dissolved in PBS and mixed in a 1:1 ratio with IFA. Mice were vaccinated subcutaneously with peptide in a volume of 200 μl at day 1. Fourteen days later mice were challenged with 0.5×10$^6$ AR5 tumor cells (E1A +Ras transformed mouse embryo cells). Survival of mice was monitored during a 100 day follow-up.

Results

Vaccination with synthetic peptides representing cytotoxic T lymphocyte (CTL) epitopes can lead to a protective CTL-mediated immunity against tumors or viruses. B6 tumor cells transformed by the human adenovirus early region 1 (Ad5E1) present an Ad5E1A- and an Ad5E1B-encoded CTL epitope to the immune system. CTL clones directed against either of these epitopes are able to eradicate established Ad5E1-induced tumors, showing that these CTL epitopes are targets of CTL that can mediate tumor regression. Protective immunity against Ad5E1-expressing tumor cells can be established by immunization with Ad5E1-transformed cells and with an adenovirus vector containing the Ad5E1 region. Protective immunity, in either case, is associated with specific CTL memory. When, however, mice were vaccinated with either the minimal peptide-epitope sequence of the E1A-derived CTL epitope or the minimal peptide-epitope sequence of the E1B-derived CTL epitope protection against Ad5A1—expressing tumors was lost.

Vaccination with a CTL epitope derived from the human adenovirus type 5 E1A-region (Ad5E1A234-243), enhances rather than inhibits the growth of Ad5E1A-expressing tumors. In contrast to peptide vaccination, immunization with adenovirus, expressing Ad5E1A, induced Ad5E1A-specific immunity and prevented the outgrowth of Ad5E1 Aexpressing tumors. These results show that immunization with synthetic peptides can lead to the elimination of antitumor CTL responses (Toes et al., 1996a). Furthermore, vaccinated mice s.c. with a low dose of the Ad5E1B peptide also showed this adverse reaction. The Ad5E1B peptide was chosen because the CTL response against the Ad5E1B-encoded CTL epitope contributes most to the antitumor response in B6 mice after vaccination with Ad5E1-transformed cells. Ad5E1B peptide-vaccinated mice were not protected against the outgrowth of Ad5E1-expressing tumor cells, but instead were no longer able to reject a tumor inoculum that was rejected by nonvaccinated mice.

Moreover, the protection induced by tumor cell vaccination against Ad5E1B-expressing tumors was gone when the Ad5E1B-encoded CTL epitope was injected a few days before tumor challenge. This is associated with peptide-induced tolerance of Ad5E1B-specific CTL activity (Toes et al. 1996b).

In conclusion, immunization with synthetic peptides of the exact CTL epitope length, can also lead to CTL tolerance associated with the inability to reject tumors. The issue of tolerance or functional deletion of CTL by immunization with minimal epitopes is circumvented by the use of long peptide (22-35 amino acid residues). To proof this statement we vaccinated C57/B16 mice with a 32 amino long E1A derived peptide that contains the 10 amino acid long CTL E1A-derived epitope, which when given as the exact peptide-epitope is involved in loss of tumor-protection. As shown in FIG. 10, control mice (n=8) that have been vaccinated with the exact peptide-epitope SGPSNTPPEI (SEQ. ID. NO. 1), all die within 50 days after tumor-challenge. In contrast, the group of mice vaccinated with the 32 amino acid long peptide all live at 50 days and only one mouse is lost during the 100 day follow-up.

Conclusion

For a clinically relevant approach of immunizing subjects against virally infected cells or tumor cells both specific T-helper cells and CTL should be induced. We have already shown that immunization with minimal CTL epitopes results in protection against tumors in some models (Kast et al. 1991, Feltkamp et al. 1993) whereas it can also lead to tolerance or functional deletion of virus-and tumor-specific CTL that when otherwise induced are protective (Toes et al. 1996ab). Processing of exogenous antigens for presentation by MHC class I molecules by cross-priming as well as by other mechanisms is now widely recognized second pathway of processing for presentation by MHC class I, next to the well known endogenous route (Jondal et al., 1996, Reimann et al. 1997). We have now shown that in contrast to vaccination of mice with the exact peptide-epitope, vaccination with long peptide sequences containing CTL epitopes does not result in the loss of CTL that are involved in the protection of mice against tumors but instead result in a CTL mediated immune response that protects mice against a subsequent tumor-challenge.

Example 5

Mice and cell lines. C57BL/6 (B6, H-2$^b$) mice were obtained from IFFA Credo (Paris, France). MHC class II$^{31}$/31 B6 mice were purchased from Taconic (USA) and CD40$^{-/-}$ B6 mice were obtained from The Jackson Laboratory (Maine, USA). Tumor cell line TC-1 was generated by transfection of Mouse Embryo Cells (MEC) of C57BL/6 origin by HPV 16 E6/E7 and c-H-ras oncogenes. Tumor cell line 13.2 was derived from MEC (B6) transformed with adenovirus type 5 derived E1 protein in which the H-2Db E1A epitope was replaced with the HPV 16 E7$^{49-57}$ CTL epitope. D1 cells are long-term growth factor dependent immature splenic dendritic cells (DC) derived from C57BL/6 mice.

Peptides. The HPV16-E7-derived peptides E7$_{49-57}$: RAHYNIVTF (SEQ. ID. NO. 3) and E7$_{43-77}$:GQAEP-DRAHYNIVTFCCKCDSTLRLCVQSTHVDIR (SEQ. ID. NO. 13) were synthesized by solid phase strategies on an automated multiple peptide synthesizer (Abimed AMS 422, Langenfeld, Germany). The peptides were analysed by reverse phase HPLC for contaminants and stored at -20° C.

Tetramers and antibodies. PE-labelled H-2D$^b$ epitope E7$^{49-57}$ (RAHYNIVTF) (SEQ. ID. NO. 3)—containing tetramers were constructed and used for the analysis of peptide-specific CTL-immunity. FITC labelled anti-CD8b.2

Ab (Ly-3.2) (clone 53-5.8), APC labeled anti-CD4 Ab (L3T4) (clone RM4-5) and PE labeled anti-IFN-γ Ab (clone XMG1.2) (BD PharMingen, San Diego, USA) were used in the various FACS procedures.

Adjuvantia. IFA (incomplete Freund's adjuvant) was obtained from Difco Laboratories (Michigan, USA). Montanide ISA 51 was purchased from SEPPIC (Paris, France). CpGoligodeoxynucleotides (ODN) 1826 were kindly provided by Dr. G. B. Lipford, Technical University of Munich (Munich, Germany). GM-CSF was obtained from Pepro-Tech (Rocky Hill, USA). The FGK-45 hybridoma cells producing stimulatory anti-CD40 Ab were provided by A. Rolink. MPL was kindly provided by Dr. M. Johnson, Ribi Immunochem. Research (Hamilton, USA).

Immunization strategies. C57BL/6 mice were injected subcutaneously with either 50 µg $E7^{49-57}$ peptide or 150 µg $E7^{43-77}$ 35-mer dissolved in PBS in order to achieve similar molar levels of the $E7^{49-57}$ CTL epitope in both cases. Combinations with various adjuvantia were tested. In the case of IFA and Montanide, the dissolved peptides were emulsified in 50% of these respective substances. ODN-CpG (50 µg/mouse), MPL (10 µg /mouse) and GM-CSF (4 µg/mouse) were all dissolved in PBS and mixed with the peptides before subcutaneous vaccination. The total injected volume was 200 µl/mouse.

Anti-CD40 Ab was dissolved in PBS and injected separately from the peptides intravenously on day 0, 1 and 2 at an amount of 100 µg per injection (total volume 200, µl/mouse). Either spleens were harvested after 10 days or, when indicated, mice were boosted with identical vaccines 50 days after priming and spleens were harvested 10 days after booster immunization. In the case of the 35-mer $E7^{43-77}$, the latter strategy might allow the formation of memory CTL-and T helper cells after the first vaccination and activation of DC by HPV16 $E7^{43-77}$ specific T helper cells when the booster immunization was given. In the therapeutic anti-tumor experiments, tumor-bearing mice were vaccinated twice: at the time that tumors were palpable in all mice and 14 days later.

T cell cultures. T cells were obtained from immunized mice by culturing spleen cells ($5×10^6$ cells/well of a 24-wells plate) in complete medium in the presence of $0.5×10^6$ $E7^{49-57}$-expressing cells (tumor cell line 13.2) or, when indicated, in the presence of D1 cells.

Before use, the D1 cells were incubated for 16 hours with the $E7^{43-77}$ 35-mer and subsequently activated by adding LPS (10 µg/ml) for 6 hours and then thoroughly washed. Complete medium consists of Iscove's Modified Dulbecco's Medium (IMDM; BioWhittaker, Walkersville, Md., USA) supplemented with 8% FCS, 100 IU/ml penicillin, 2 mM glutamine (ICN, Aurora, Ohio, USA) and 30 µM 2-ME (Merck, Darmstadt, Germany). Cultures were maintained at 37° C. in humidified air containing 5% $CO_2$. No exogenous IL-2 was added. On day six, dead cells were removed from the culture by centrifugation over a Ficoll density gradient and remaining cells were seeded in 24-wells plates at $1×10^6$ cells/well. On day seven tetramer staining or intracellular cytokine staining was performed.

Tetramer staining. Spleen cultures, stimulated with tumor cell line 13.2 for seven days, were transferred at an amount of $40×10^4$ per well to 96-well V-bottom microtiter plates and washed twice with PBS/BSA 0.5%. Subsequently, PE-labelled E749-57—containing tetramer was added. After 30 minutes of incubation at room temperature, cells were washed twice with PBS/BSA 0.5% and incubated with FITC-labelled anti CD8b Ab for 30 minutes. Subsequently cells were washed twice in PBS/BSA 0.5%, suspended in PBS/BSA 0.5% containing Propidium Iodide (PI) (0.5) µg/ml) and transferred to tubes. Cell samples were analysed in a FACSCalibur flow cytometer (Becton Dickinson, San Jose, Calif., USA) using CellQuest software. A total of $20×10^4$ events was analysed for fluorescence intensity. Debris was gated out using the PI staining and subsequently the $CD8^+$ fraction was gated. Mean background tetramer-staining of similarly cultured and stained cells from non-immunized control mice was found to be below 1 percent of CD8+ cells (0,94%, standard deviation 0.36%). As a positive control the HPV16 E7 specific CTL clone 9.5 was used.

Intracellular cytokine staining. Spleen cultures were stimulated with D1 cells pulsed with $E7^{43-77}$ 35-mer for seven days. Subsequently, the percentage of $CD8^+$ and $CD4^-$ IFN-γ producing T cells was measured as described before (van der Burg et al., 2001). Notably, LPS-activated non-pulsed D1 cells or D1 cells pulsed with $E7^{49-57}$ or $E7^{43-77}$ 35-mer (5 µg/ml) were used as stimulator cells.

Results

Prime-boost Vaccinations with the $E7^{43-77}$ 35 Amino Acid Long HPV16 E7 T Helper-and CTL Epitope Containing Peptide Result in a Vigorous CTL Response.

Mice (B6) were vaccinated once with either the minimal CTL epitope HPV16 $E7^{49-57}$ or the HPV16 $E7^{43-77}$ 35 amino acid residue long peptide, admixed with IFA. Ten days following vaccination spleens were harvested and stimulated in vitro for 1 week. Subsequently, the percentage of $E7^{49-57}$ peptide-specific CTL was determined by $H2-D^b$ $E7^{49-57}$ (RAHYNIVTF) (SEQ. ID. NO. 3)—tetramer staining (van der Burg et al., 2001). In both groups 3 out of 9 mice responded to the vaccine while generally 5 percent of the CD8– T cells stained with tetramers (FIGS. 11a, 11b), suggesting that the vaccines do equally well when injected once.

To obtain a vigorous $E7^{49-57}$-specific CTL response, both vaccines were used in a primeboost regimen, which allowed primed T cells to form memory T cells before the response was boosted by a second vaccination 50 days later. Mice that received twice the minimal CTL epitope, showed $CD8^+$ T cell responses that were comparable to that after one vaccination (FIG. 11c). In contrast, mice primed and boosted with the long peptide displayed a vigorous $E7^{49-57}$-specific CTL response in 9/11 mice, with high numbers of $E7^{49-57}$-specific $CD8^+$ T cells (mean 19%, range 5-40%) (FIG. 11d). These experiments demonstrate that vaccination with the long peptide in a homologous prime-boost regimen is superior to vaccination with the minimal CTL epitope and this indicates that the formation of T helper cells, by the intrinsic T helper epitope present in the long peptide, contributes considerably to the level of the CTL responses.

The vigorous $E7^{49-57}$-specific CTL Response is Dependent on MHC Class II-restricted T Helper Cells and CD40-CD40L interactions.

In order to demonstrate that the impressive CTL responses, detected following primeboost vaccinations with the long $E7^{43-77}$ peptide, were in fact enhanced by MEW class II-restricted E7-specific T helper cells, MHC class $II^{-/-}$ mice were prime-boosted with the long peptide vaccine. The number of $E7^{49-57}$-specific CTL detected in the MEW class $II^{-/-}$ mice was far lower than found in B6 mice after two vaccinations, and comparable to that found after one vaccination (FIG. 11e). To confirm that $CD4^+$ T helper cells are already induced after priming, mice were vaccinated once with the long peptide in IFA.

Subsequently the percentage of $E7^{43-77}$-specific IFN?-producing $CD4^+$ T cells was measured by intracellular cytokine staining. Whereas no responses over background were observed in naive mice (data not shown), 5 percent or more of the CD4+ T cells from vaccinated mice specifically responded upon stimulation with the long E7$^{43-77}$ peptide (FIG. 12a). These data not only indicate that MHC class II restricted CD4+ T helper type 1 responses are induced after one vaccination but also that these E7$^{43-77}$ peptide-specific T helper cells are required for inducing vigorous CTL responses.

Professional APC, that process and present the long peptide upon the booster immunization, are activated through CD40-CD40L interactions by E7$^{43-77}$ peptide-specific T helper cells. This will subsequently lead to enhanced CTL activation.

Single Vaccinations with the E7 $^{43-77}$ Peptide and DC-activating Agents Result in Vigorous T Helper-and CTL Responses Towards HPV16 E7.

If the T helper-mediated activation of professional APC is important for the observed vigorous CTL response, direct activation of DC should bypass a lack of T cell help and a single vaccination should be sufficient to raise adequate CTL responses. To address this subject, B6 mice were vaccinated once with the long peptide or the minimal E7$^{49-57}$ peptide in combination with various DC-activating agents. IFA and Montanide-a human grade IFA-were used as controls. As with IFA (FIGS. 11a, 11b) no responses were observed when Montanide adjuvant was administered (data not shown).

Furthermore, mice vaccinated with either the minimal CTL epitope or the long peptide combined with anti-CD40 antibody or GM-CSF displayed no or minimal CTL responses (FIGS. 13a, 13b). However, the combination of GM-CSF and IFA resulted in moderate E7$^{49-57}$-specific CTL responses when the long peptide was administered (FIG. 13c).

Mice receiving the minimal peptide mixed with MPL or ODN-CpG showed clear-cut CTL responses in several mice (FIGS. 13d, 13e) although the number of responders was not increased (4/9 and 4/12 mice respectively) compared to mice vaccinated with IFA (FIG. 11A). In contrast, vaccination with the long peptide resulted in E7$^{49-57}$-specific CTL responses in all mice. Moreover, the level of the CTL response detected was high (up to 40% of CD8+ T cells) in the majority of animals. In addition, a single vaccination with the long peptide and ODN-CpG resulted in even higher numbers of E7$^{43-77}$-specific IFNγ -producing CD4+ T cells (15 to 20% of CD4+ T-cells) when compared to the use of IFA as adjuvant (FIG. 12b). To demonstrate that the induced responses were indeed T helper cell independent, MHC class II$^{-/-}$ mice were vaccinated with the long peptide and ODN-CpG. As shown in FIG. 13f, robust CTL responses were detected after one vaccination. The observation that in a T helper independent setting, vaccination with the long peptide and a DC-activating agents is superior to vaccination with the minimal CTL epitope shows that, compared to the minimal CTL epitope that can bind to MHC class I molecules present on all nucleated cells, the long peptide is preferentially processed and presented by professional antigen presenting cells (APC).

Vaccination with the 35-mer and the DC-Activating Adjuvant ODN-CpG can Effectively Eradicate HPV16 Expressing Tumors.

In order to test the efficacy of the long peptide vaccine, tumor bearing mice were immunized with the E7$^{49-57}$ peptide or the E7$^{43-77}$ long peptide admixed with ODN-CpG. Notably, the vaccination was given at the time when tumors were palpable (day 10-14) in all mice. A second vaccination was administered 14 days later in order to sustain E7specific T helper-and CTL immunity. Mice treated with ODN-CpG alone did not display anti-tumor activity (FIG. 14a). The majority of animals had to be killed due to extensive tumor growth within 14 days after treatment. In both groups treated with peptide and ODN-CpG inhibition of tumor growth was seen 8-12 days after treatment.

Although complete eradication was observed in 3 out of 9 mice treated with the E7$^{49-57}$ peptide and ODN-CpG (30% of the animals), others were only capable of stabilizing tumor growth temporarily and then died of their tumor. In contrast, 8 out of 10 mice treated with the long peptide and ODN-CpG eradicated their tumors, some of them sizing up from 200-500 mm$^3$.

Conclusion

We show that the HPV16 E7-specific CTL response is far more vigorous after vaccination with a HPV16 E7 derived 35-residue long peptide than following vaccination with the minimal CTL epitope. Our data demonstrate that at least one of two independent mechanisms account for this. Firstly, the long 35-residue peptide used in this example contains both a CTL epitope and a T helper epitope. Vaccination of MHC class II−/−mice demonstrated that the interaction between APC and E7-specific T-helper cells contributed considerably to the level of the CTL response. Furthermore, administration of said long peptide mixed with strong DC-activating agents was able to bypass the requirement for T cell help. Secondly, a direct comparison of the CTL response induced by the minimal CTL epitope (9 residues) of this example or said long peptide vaccine combined with DC activating agents in both wild type and MHC class II−/−mice showed that vaccination with the long peptide resulted in a far better CTL response, showing that in contrast to the minimal CTL epitope, the long peptide is preferably presented by professional APC. Moreover, we show that vaccination with the long peptide and strong DC activating agents result in the complete eradication of established tumors. These data provide a scientific basis for the use of long overlapping peptides, alone or in combination with strong DC activating agents in future human trials.

The high efficacy of our long peptide-vaccine is among other things due to the fact that the T helper-and CTL epitope are physically linked to each other. The potential advantage of epitope-linkage lies in the increased chance for simultaneous presentation of both the MHC class I and class II restricted epitopes on the surface of a single APC, thereby facilitating the delivery of cognate T cell help to CTL priming. A direct comparison of vaccines that used a mix of CTL and Th-epitopes with vaccines that used physically linked, but identical, CTL and Th-epitopes demonstrated that the latter resulted in more vigorous CTL responses (Shirai, 1994; Hiranuma, 1999 ; Bristol, 2000).

Our vaccinations of normal B6 and MHC class II−/−mice confirm that the use of a physically linked T-helper epitope is advantageous for the development of a strong CTL response. In addition, these experiments demonstrated that the interaction between E7specific Th-cells and APC is responsible for this boost of the CTL response.

Comparison of the CTL response induced by the minimal CTL epitope and the long peptide in normal and MHC class II−/−mice revealed another interesting property of our long peptide vaccine. In these experiments the contribution of E7-specific Th-cells was eliminated and only differences in physical properties or kinetics of the peptides are likely to play a role. Because of its size, which excluded direct binding of peptide to MHC class I, said long peptide needed to be taken up by professional APC that are able to process exogenously derived antigens and present peptides in MHC class I. We demonstrated that DC activation only marginally affected the outcome of the E7specific CTL response when the minimal peptide was used whereas DC activation was a prerequisite for the induction of a superior E7-specific CTL response by the long peptide vaccine. Together these data show that the CTL and Th-epitope present in said long peptide are preferably presented at the surface of professional APC.

Vaccination with the minimal HPV16-derived CTL epitope results in a detectable CTL response that is not improved when DC activating agents are co-injected. This indicates that said peptide is not only presented at the surface of activated professional APC but also in MHC class I molecules of other nucleated cells. This is not surprising because said peptide can directly bind to MHC class I at the cell surface (Feltkamp et al., 1993).

Presentation of said CTL peptide by cells that cannot deliver co-stimulation (e. g. nonimmune cells) results in a dampening of CTL responses and the presentation of said E7 CTL epitope by these non-professional APC are, therefore, deleterious to the induction of E7-specific CTL. Notably, we have shown previously that vaccination with the minimal E1A-derived CTL epitope resulted in tolerance of E1A-specific CTL that, otherwise, were protective against E1A induced tumors (Toes 1996). Although, the possible presentation of the HPV16 E7-derived CTL epitope at the surface of nonprofessional APC does not hinder the induction of E7-specific CTL as seen in the adenovirus tumor model, the anti-tumor efficacy of these responses is hampered.

Treatment of established tumors by therapeutic vaccination with the minimal CTL epitope and the DC activating agent CpG is far less effective when compared to the long peptide vaccine mixed with DC activating agents.

These results provide a scientific basis for the evaluation of this vaccine in human trials for both prophylactic and therapeutic intervention against HPV16 induced disease.

BRIEF DESCRIPTION OF THE FIGURES

FIGS. 6a-6d depict a peptides $E2_{301-330}$ and $E2_{316-345}$. induced T-cell response that recognizes naturally processed Ag. PBMC from a healthy HLA-DR2, DQ6 (1) positive blood donor were stimulated four times with peptides $E2_{301-330}$ and $E2_{316-345}$. Specific proliferation of the T-helper cell clone against peptide $E2_{301-330}$ and E2 protein (FIG. 6a), specific production of IFNγ by the T-helper cell clone when stimulated with $E2_{301-330}$ (FIG. 6b), fine-mapping of the minimal epitope $E23_{311-325}$ (FIG. 6c), and anti HLA-DQ antibody blocks the E2-specific IFNγ production of the T-helper cell clone revealing HLA-DQ6 (1) as restriction element (d). (See, also, FIGS. 1a-1d and associated descriptions).

FIGS. 9a-9f depict E2-peptide specific IFNγ-production of T-cells present in the CD45RO+ (memory)-fraction of PBMC. The CD45RO+ memory fraction of PBMC were isolated using MACS technology. Following separation these memory T-cells were stimulated with indicated peptides. After 10 days of incubation the cells were harvested, washed and then stimulated with the indicated peptides in a 96-well ELISPOT plate at 50,000 PBMC per well. The number of IFNγ -producing T-cells per 50,000 PBMC is indicated on the Y-axis of each of FIGS. 9a-9f. Healthy blood donor derived CD45RO+ PBMC contain HPV16 E2specific memory T-cells as shown by the reaction to several pools of : two 30 amino acid long E2 peptides (first amino acid of first peptide and last amino acid of second peptide are indicated at X-axis) that were selected based on immunogenicity of these peptides, which was established in previous assays (FIGS. 9a-9b), or four 30 amino acid long E2 peptides (indicated are the position of the first and last amino acid of the sequence that is covered by these 4 peptides in the E2-protein) (FIGS. 9d-9f). MRM: memory response mix which consists of a mix of *Mycobacterium tuberculosis,* Tetanus toxoid and *Candida albicans* antigens. (See, also, FIG. 4, and associated description). *, statistically significant response (p<0. 05).

FIGS. 15a and 15b are entitled E2 51-70 specific clone 47 peptide and protein recognition, and HLA-DR restriction. Specific proliferation of the T-helper cell clone 47 against peptide E2$_{46-75}$ and the N-terminal E2 protein but not the C-terminal half of the E2 protein (left, 15a) and the restriction via HLA DR4 (right, 15b) is shown. FIG. 15c is entitled E2 61-75 specific clone 36 peptide recognition. The peptide-specificity of T-helper clone 36 that recognizes a different, yet overlapping, peptide E2$_{61-75}$ is shown at the bottom (FIG. 15c). (See, also, FIGS. 1a-1d and associated descriptions).

FIGS. 16a and 16b are entitled E6 127-158 stimulated HLA-DR1+ PBMC. Proliferation of the bulk T-cell culture (top, left, 16a) and IFNγ production (top, right, 16b) is depicted. FIGS. 16c and 16d are entitled E6 127-158 stimulated PBMC derived clone 9 HLA-DR restriction in proliferation and IFNγ production. The specific proliferation (bottom, left, 16c) and IFNγ production (bottom, right, 16d) of the T-helper clone, derived from the bulk T-cell culture, and HLA-restriction when stimulated with $E6_{127-158}$, or E6protein is depicted. (See, also, FIGS. 1a-1d and associated descriptions).

REFERENCES

Figure 1A:
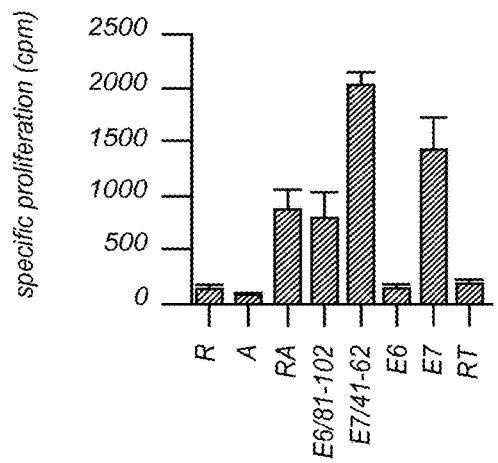
FIGS. 1a-1d depict the peptide E741-62 induced T-cell response that recognizes naturally processed antigen (Ag). PBMC from a healthy HLA-DR15, 4 and DQ6,7 positive blood donor were stimulated four times with peptide $E7_{41-62}$. The responding T-cells were tested in a 3-day proliferation assay (FIGS. 1a, 1b, and 1c) or stimulated for 1 day in order to measure the production of IFNγ by ELISA (d). Responder cells (R) and autologous or MHC class II matched antigen presenting cells (A) were incubated with the indicated Ags: recombinant HPV16 E6 protein (E6), recombinant HPV16 E7 protein (E7), recombinant HIV RT protein (RT) or peptides derived from E6 (eg $E6_{81-102}$, peptide $E6_{81-102}$) or derived from E7. Proliferation of the bulk T-cell culture (FIG. 1a), proliferation of the T-helper clone, derived from the bulk T-cell culture, and blocking of the E7 proteinspecific response by adding an antibody against HLA-DR (FIG. 1b), proliferation of the T-helper clone when stimulated with partially MHC class II matched antigen presenting cells (FIG. 1c), and fine mapping of the minimal epitope by measurement of the IFNγ production per 24 h by the T-helper clone (FIG. 1d).
Figure 1B:
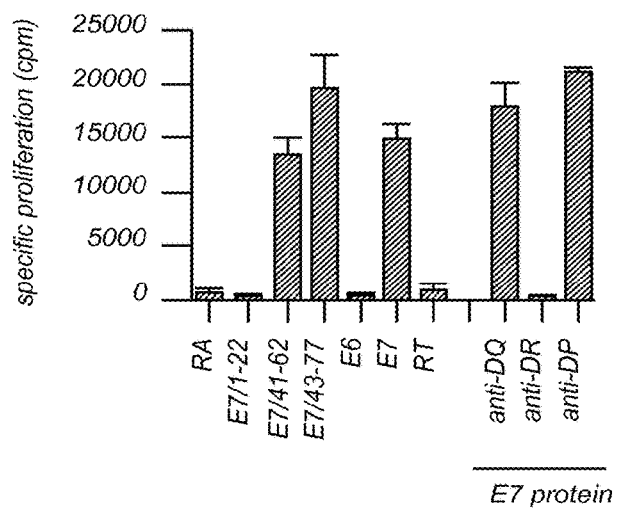
Figure 1C:
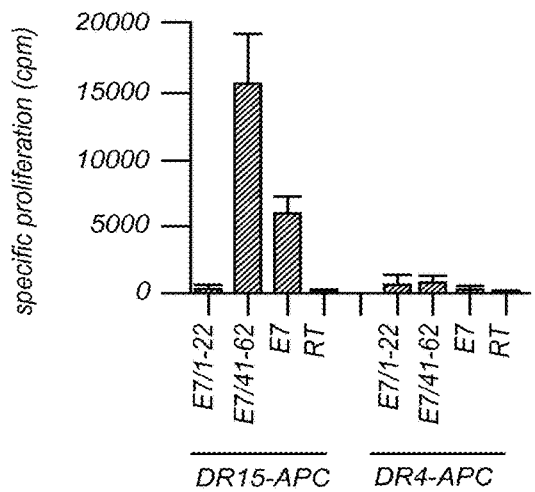
Figure 1D:
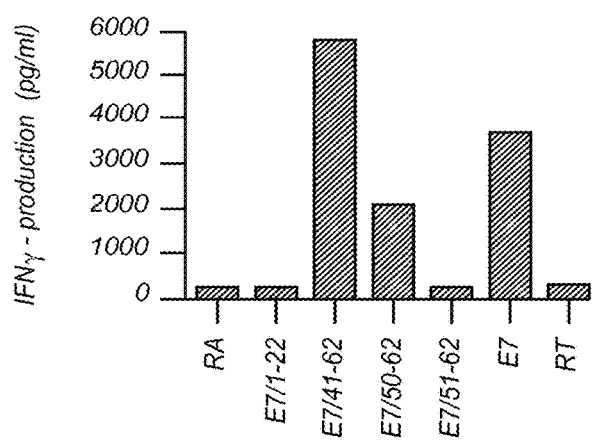
Figure 2A:
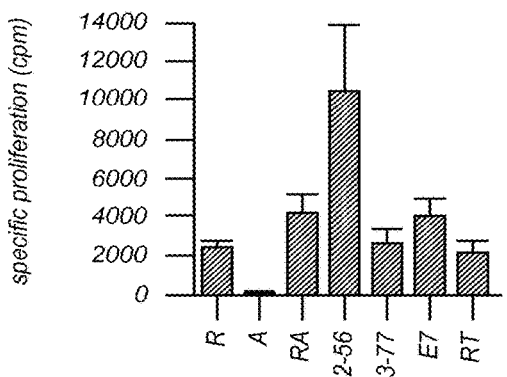
FIGS. 2a-2c depict a peptide $E7_{22-56}$ induced T-cell response that recognizes naturally processed Ag. PBMC from a healthy HLA-DR3 and DQ2 positive blood donor were stimulated four times with peptide $E7_{22-56}$ Proliferation of the bulk T-cell culture (FIG. 2a), specific proliferation of the T-helper clone, derived from the bulk T-cell culture, when stimulated with $E7_{22-56}$, $E7_{31-52}$ and E7 protein (FIG. 2b), and fine mapping of the minimal epitope and MHC class II restriction by measurement of the IFNγ production per 24 h of the T-helper cell clone (FIG. 2c). (See, also, FIGS. 1a-1d and associated descriptions).
Figure 2B:
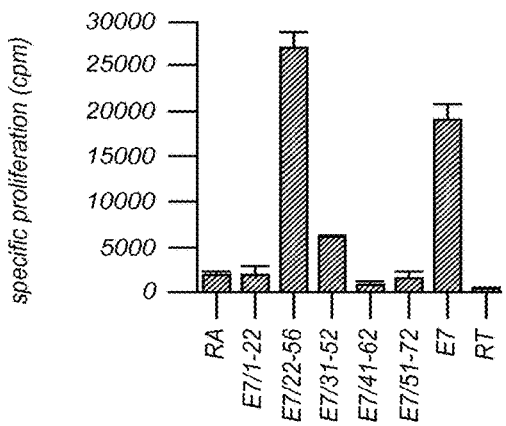
Figure 2C:
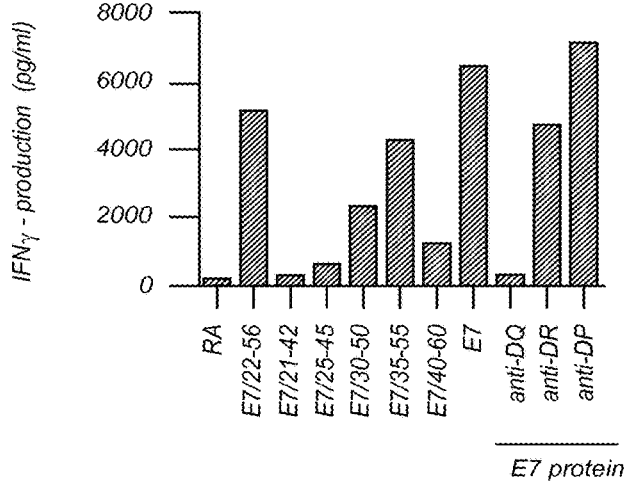
Figure 3A:
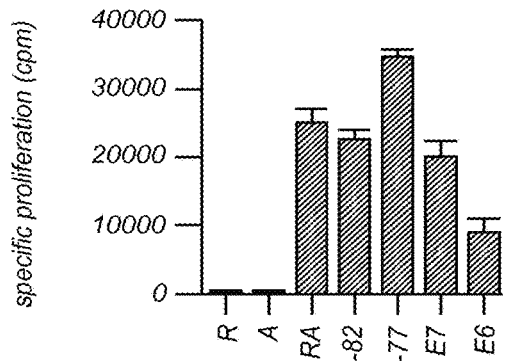
FIGS. 3a-3e depict a peptide $E7_{43-77}$ induced T-cell response that recognizes naturally processed Ag. PBMC from a healthy HLA-DR1,3 and DQ2 positive blood donor were stimulated four times with peptide $E7_{43-77}$. Proliferation of the bulk T-cell culture (FIG. 3a), specific proliferation of the T-helper cell clone against peptide $E7_{43-77}$ and E7 protein (FIG. 3b), recognition of partially matched (DR3, DQ2) peptide pulsed antigen presenting cell ("APC") (FIG. 3c) anti HLA-DR antibody blocks the E7-specific proliferation of the T-helper cell clone revealing HLA-DR3 as restriction element (FIG. 3d), and specific production of IFNγ by the T-helper cell clone when stimulated with $E7_{43-77}$ peptide or E7 protein (FIG. 3e). (See, also, FIGS. 1a-1d and associated descriptions).
Figure 3B:
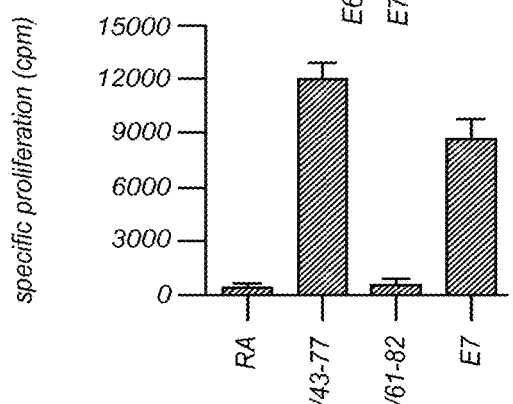
Figure 3C:
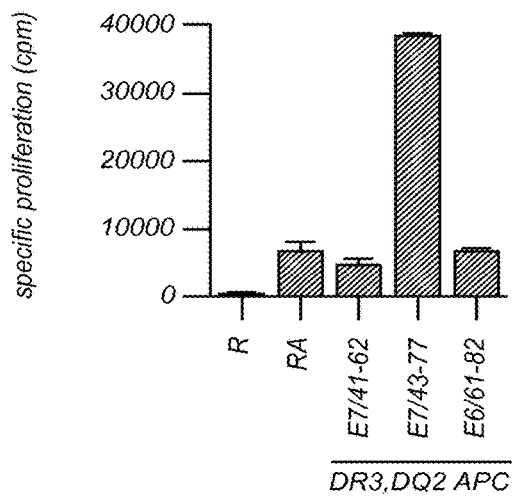
Figure 3D:
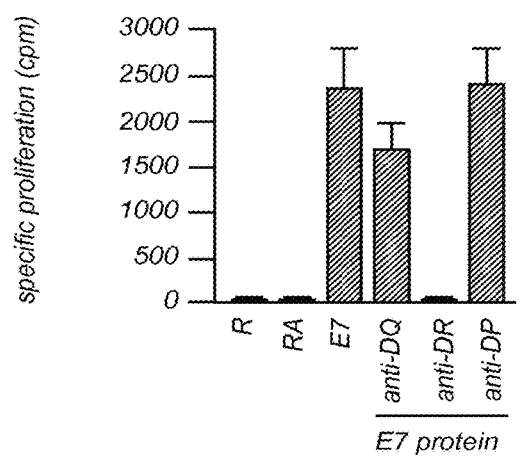
Figure 3E:
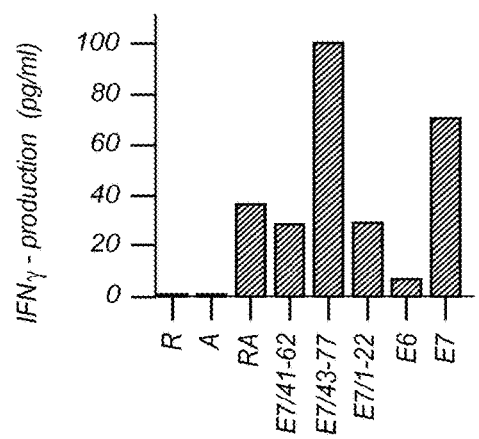
Figure 4:
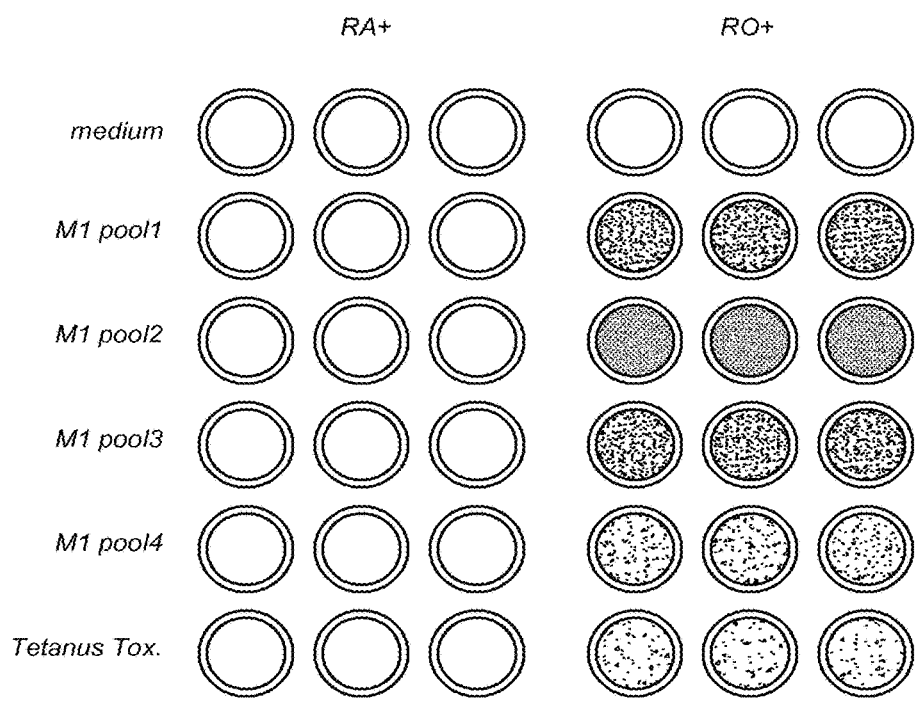
FIG. 4 depicts the stimulation with influenza matrix 1 (M1)-peptides of MACSseparated CD45RA+ (naive) T-cells (left) and CD45RO+ (memory) T-cells (right) results in the production of IFNγ in the CD45RO+ subset only. The MI protein was divided in 16 overlapping peptides. Each pool consists of four 30 amino acid long peptides that overlap by 15 amino acids. Tet. tox.: tetanus toxoid.
Figure 5A:
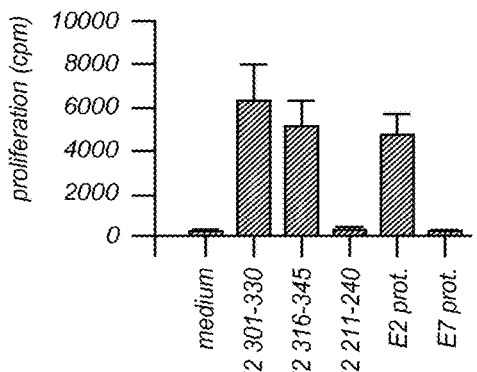
FIGS. 5a-5d depict a peptides $E2_{301-330}$ and $E2_{316-345}$ induced T-cell response that recognizes naturally processed Ag. PBMC from a healthy HLA-DR2 positive blood donor were stimulated four times with peptides $E2_{301-330}$ and $E2_{316-345}$. Specific proliferation of the T-helper cell clone against peptide $E2_{301-330}$ and $E2_{316-345}$ and E2 protein (FIG. 5a), specific production of IFNγ by the T-helper cell clone when stimulated with $E2_{301-330}$ and $E2_{316-345}$ peptides (FIG. 5b), fine-mapping of the minimal epitope $E2_{316-330}$ (FIG. 5c) and anti HLA-DR antibody blocks the E2-specific IFNγ production of the T-helper cell clone revealing HLA-DR2 as restriction element (FIG. 5d),. (See, also, FIGS. 1a-1d and associated descriptions).
Figure 5B:
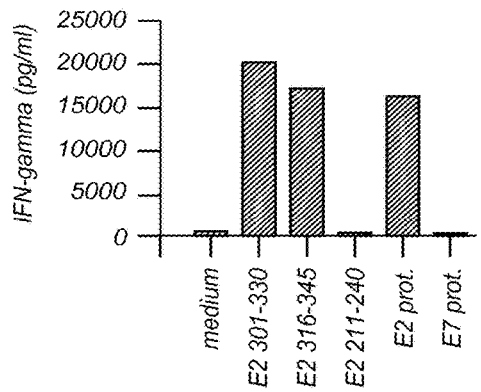
Figure 5C:
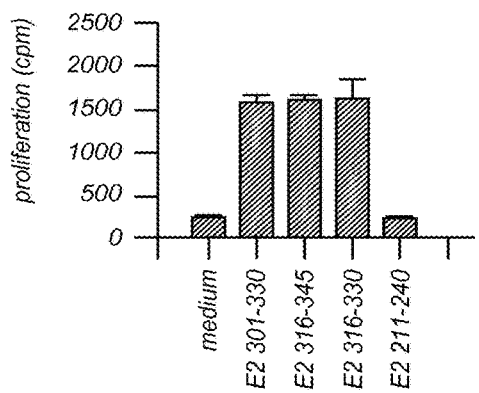
Figure 5D:
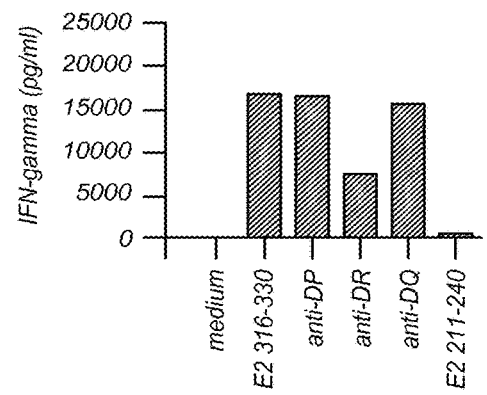
Figure 7A:
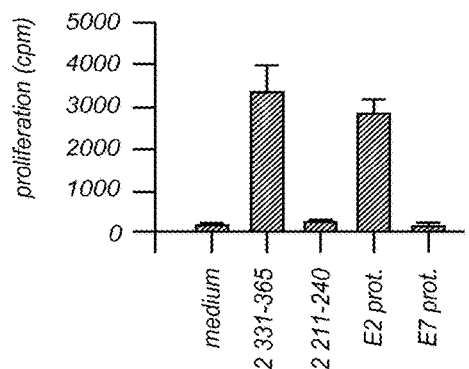
FIGS. 7a-7d depict a peptide $E2_{331-365}$ induced T-cell response that recognizes naturally processed Ag. PBMC from a healthy HLA-DR2 positive blood donor were stimulated four times with peptide $E2_{331-365}$. Specific proliferation of the T-helper cell clone against peptide $E2_{331-365}$ and E2 protein (FIG. 7a), specific production of IFNγ by the T-helper cell clone when stimulated with E2331-365 peptide (FIG. 7b), fine-mapping of the minimal epitope $E2_{346-355}$ (FIG. 7c) and anti HLA-DR antibody blocks the E2-specific IFNγ production of the T helper cell clone revealing HLA-DR2 as restriction element (FIG. 7d). (See, also, FIGS. 1a-1d and associated descriptions).
Figure 7B:
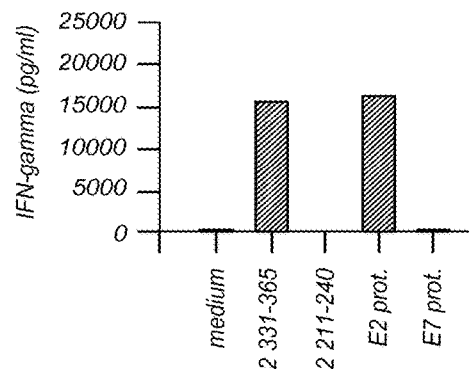
Figure 7C:
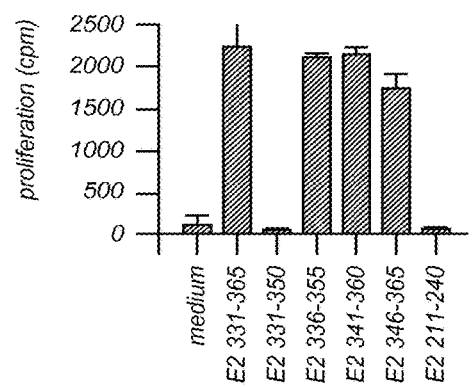
Figure 7D:
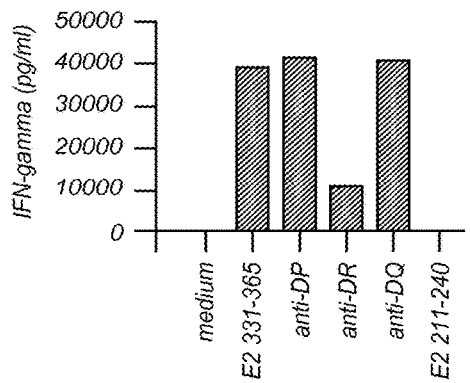
Figure 8A:
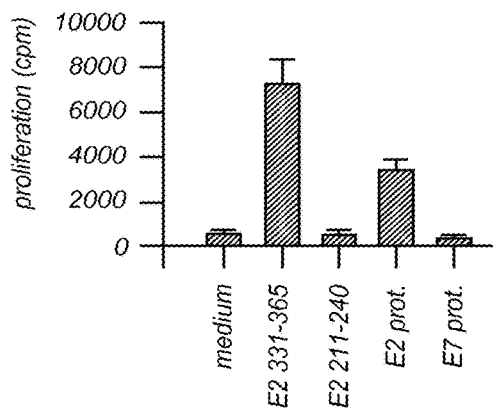
FIGS. 8a-8c depict a peptide $E2_{331-365}$ induced T-cell response that recognizes naturally processed Ag. PBMC from a healthy HLA-DR1 positive blood donor were stimulated four times with peptide E2331.36s. Specific proliferation of the T-helper cell clone against peptide $E2_{331-365}$ and E2 protein (FIG. 8a), fine-mapping of the minimal epitope E2$_{351-365}$ (FIG. 8b), and anti HLA-DR antibody blocks the E2-specific IFNγ production of the T-helper cell clone revealing HLA-DR1 as restriction element (FIG. 8c). (See, also, FIGS. 1a-1d and associated descriptions).
Figure 8B:
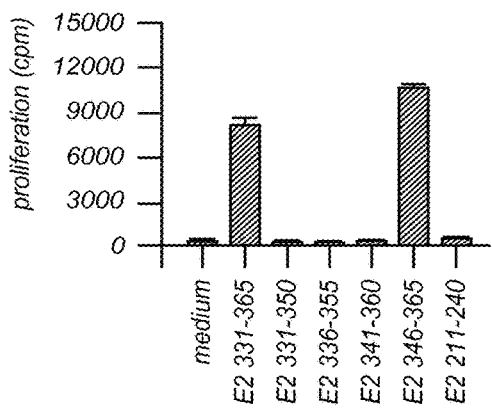
Figure 8C:
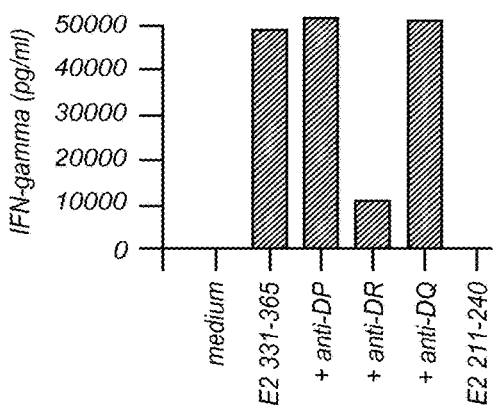
Figure 9A:
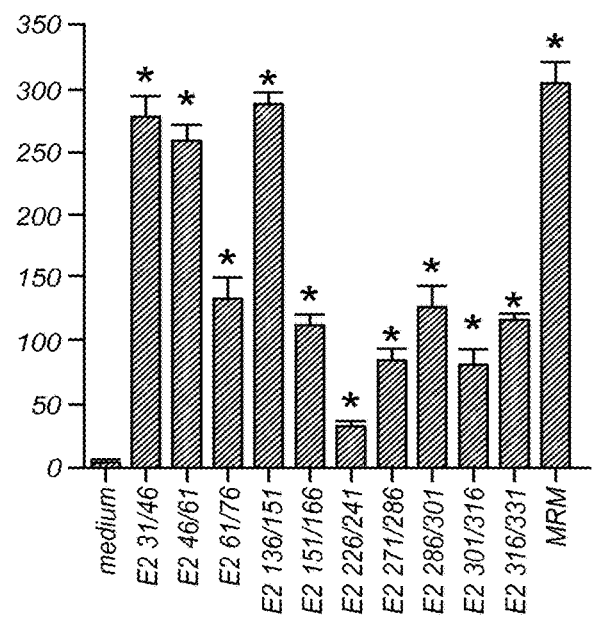
Figure 9B:
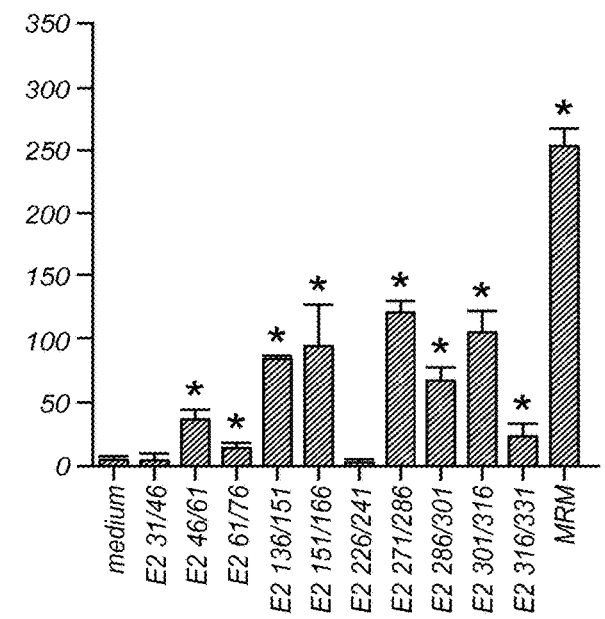
Figure 9E:
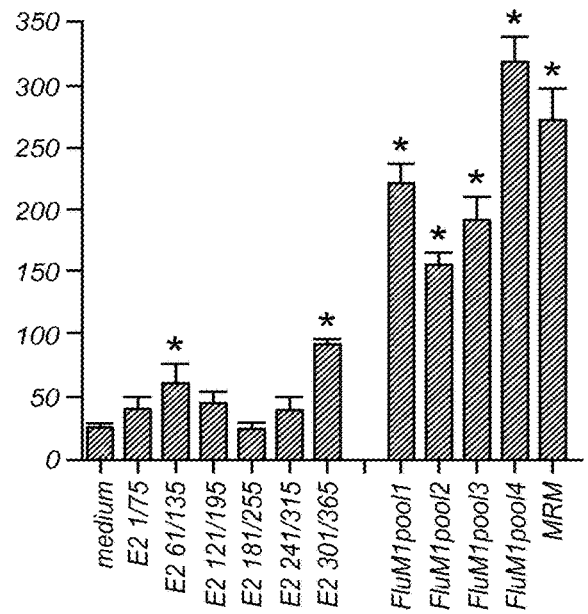
Figure 9F:
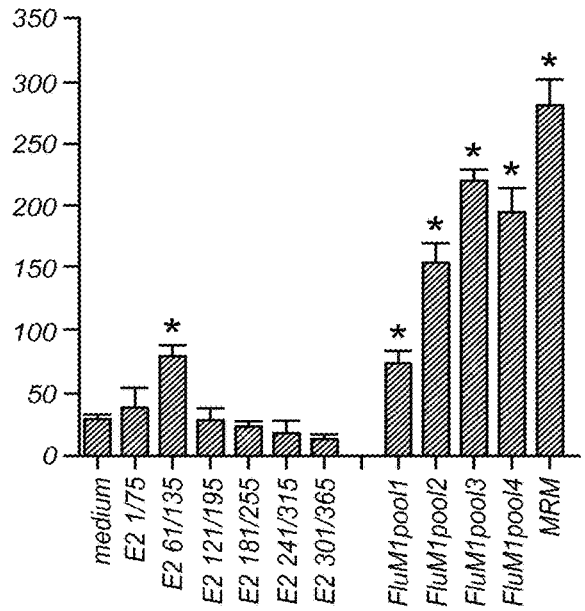
Figure 10:
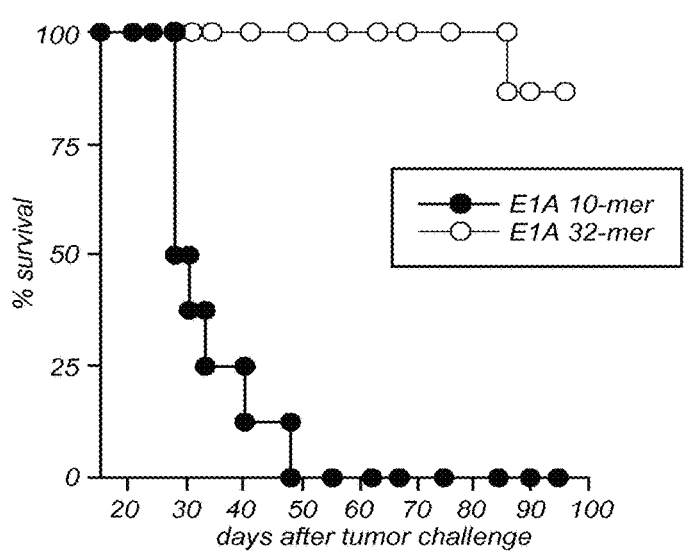
FIG. 10 depicts the survival of C57/B16 mice when immunized once with 30 μg of the 32 amino acid long peptide (RECNSSTDSCDSGPSNTPPEIHPVVRLCPIIKP) (SEQ. ID. NO. 2) containing the minimal CTL epitope. Mice were challenged 14 days later with 0.5 million AR5 tumor cells at the opposite flank. In contrast, mice immunized with the minimal 10 amino acid long CTL epitope (SGPSNT-PPEI) (SEQ. ID. NO. 1) were not protected.
Figure 11A:
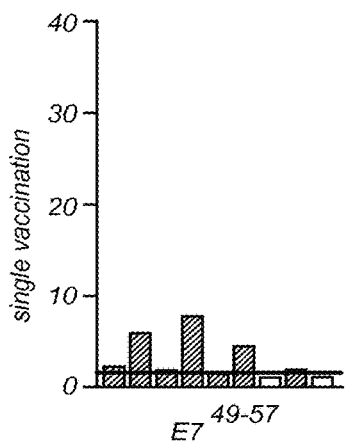
FIGS. 11a-11e depict how MHC class II T helper cells enhance E7$^{49-57}$-specific CTL responses following prime-boost vaccinations with the HPV16 E7$^{43-77}$ 35-mer. Mice (B6) were either primed once with E7$^{49-57}$ peptide (FIG. 11a) or E7$^{43-77}$ $^{35}$-mer (FIG. 11b), or boosted 50 days later with the same peptides: E7$^{49-57}$ peptide (FIG. 11c) or E7$^{43-77}$ 35-mer (FIG. 11d). MHC class II$^{-/-}$ mice were similarly primed and boosted with $^{E743-77}$ 35-mer (FIG. 11e). Peptides were emulsified in IFA. Ten days following the final vaccination spleens were harvested and cultures were stimulated with the E7$^{49-57}$-expressing tumor cell line 13.2. Based on the forward and side scatter pattern of isolated spleen cells in the FACS, CD8 (FL4-H) staining and H-2D$^b$-RAHYNIVTF (SEQ. ID. NO. 3)—tetramers staining spleen cells are subjected to the analysis of CD8+ H-2D$^b$-RAHYNIVTF SEQ. ID. NO. 3)—tetramer positive T-cells. Indicated on the y-axis are the percentage of CD8+ T-cells that were H-2D$^b$-RAHYNIVTF (SEQ. ID. NO. 3)—tetramers positive. Each column on the x-axis represents an individual mouse. The horizontal line indicates background responses plus standard deviation of naïve mice (1.31%).
Figure 11B:
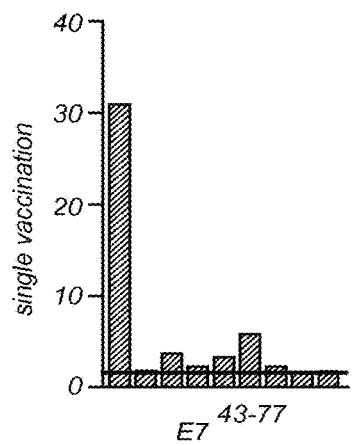
Figure 11C:
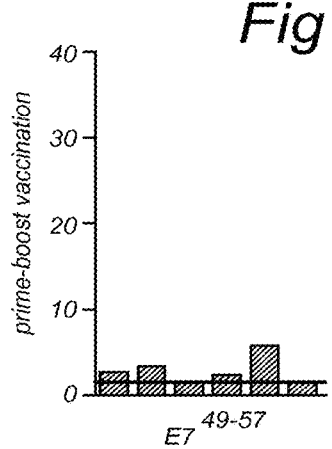
Figure 11D:
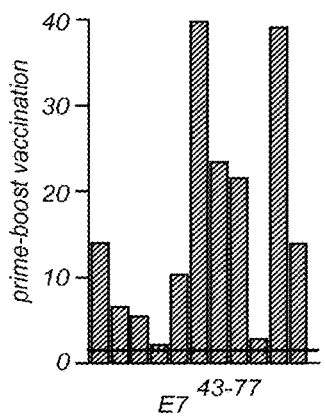
Figure 11E:
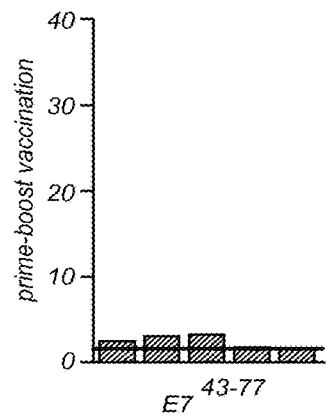
Figure 12A:
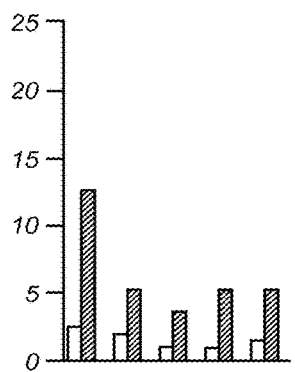
FIGS. 12a-12b depict how E7-specific T helper type 1 cells are induced following vaccination with the E7$^{43-77}$ 35-mer. Sets of 5 Mice (B6) were injected subcutaneously with E7$^{43-77}$ 35-mer admixed with IFA (A) or CpG (B). Spleens were harvested after 10-days and spleen cells cultures were stimulated with D1 cells pulsed with the E7$^{43-77}$ 35-mer. After 1 week of in vitro stimulation the specificity of the CD4$^+$ fraction of the cultures was tested by measuring the IFN-γ production of individual T cells. White columns illustrate background IFN-γ production by CD4+ T-helper cells stimulated with non-pulsed D1 cells, whereas black columns represent IFN-γ production by CD4+ T-helper cells when stimulated with E7$^{43-77}$ 35-mer pulsed D1 cells. Each set of two columns represents an individual mouse.
Figure 12B:
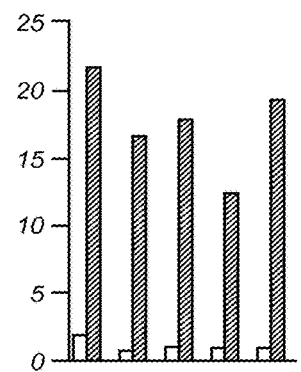
Figure 13A:
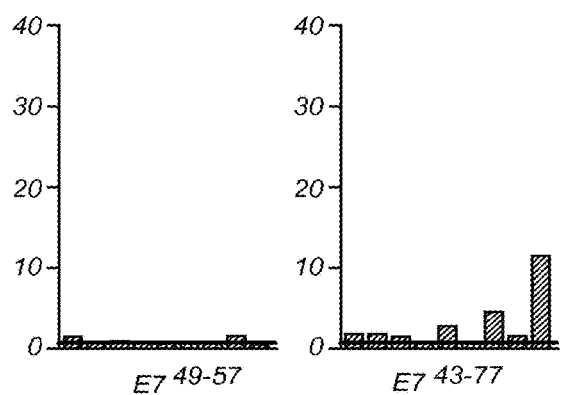
FIGS. 13a-13f depict a single vaccination of the E7$^{43-77}$ 35-mer combined with DC-activating adjuvantia results in high CTL responses. Mice (B6) were only primed and not boosted with the E7$^{49-57}$ peptide (depicted on the left) or the 35-mer (depicted on the right). Anti CD40 Ab (FIG. 13a), GM-CSF (FIG. 13b), GM-CSF plus IFA (FIG. 13c), MPL (FIG. 13d) and ODN-CpG (FIG. 13e) were used as adjuvants. Similarly, MHC class II$^{-/-}$ mice were only primed and not boosted with the E7$^{43-77}$ 35-mer and ODN-CpG (FIG. 13f). Spleens were harvested after 10-days and cultures were in vitro stimulated with the E7$^{49-57}$-expressing tumor cell line 13.2 for 7 days. Subsequently, the percentage of E7 $^{49-57}$-tetramer-positive CD8$^+$ cells was determined by FACS-analysis (y-axis). Each column on the x-axis represents an individual mouse. The horizontal line indicates background responses plus standard deviation of naive mice (1,31%).
Figure 13B:
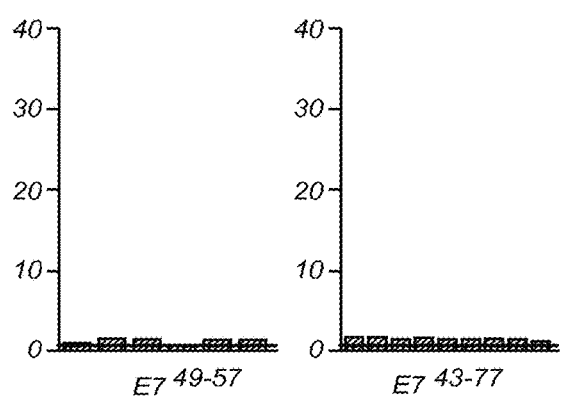
Figure 13C:
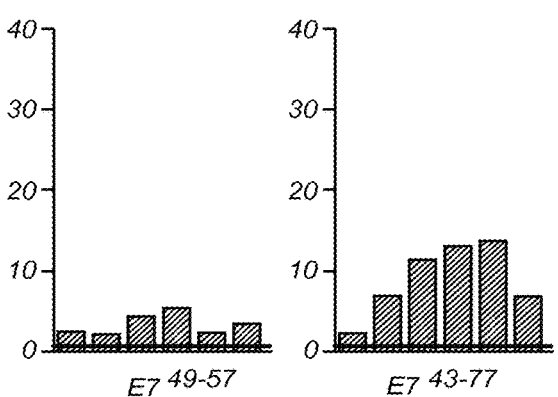
Figure 13D:
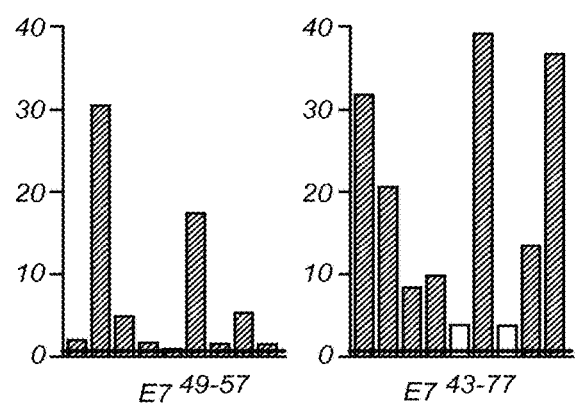
Figure 13E:
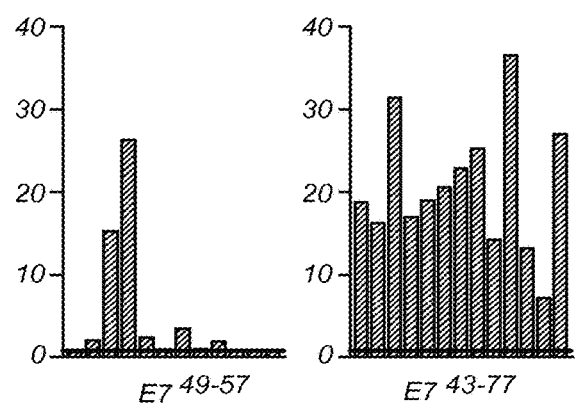
Figure 13F:
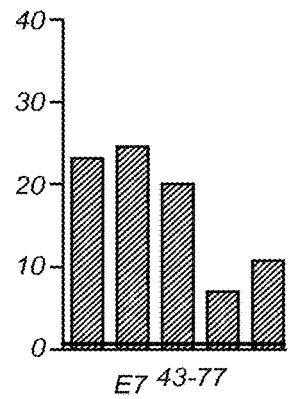
Figure 14C:
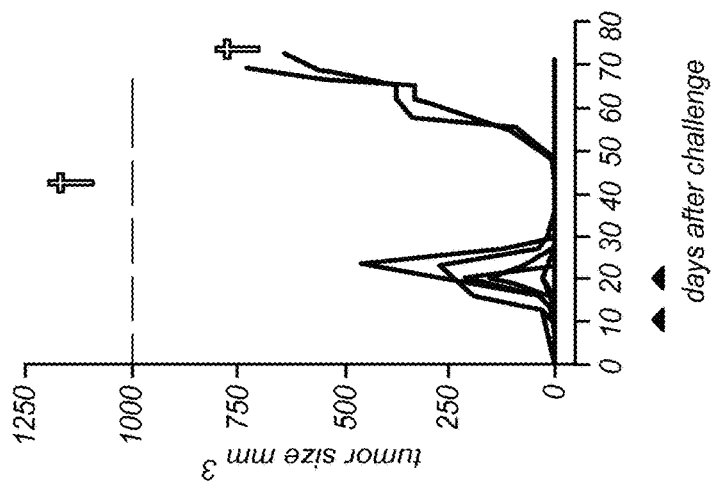
FIGS. 14a-14c depict the outgrowth of HPV16 E7 positive tumors in either TC-1 tumor challenged mice that were vaccinated with either the minimal CTL epitope E$^7$$_{49-57}$ mixed with a dendritic cell activating agent (CpG) (FIG. 14b; n=9 mice) or vaccinated with HPV16 E7$^{43-77}$ mixed with a dendritic cell activating adjuvant (CpG) (FIG. 14c; n=10 mice) or not vaccinated (FIG. 14a; n=10 mice) at the day that all mice had small palpable tumors (day 10). Mice were boosted 14 days later and tumor outgrowth was followed for 65 days after the first immunization. Note that tumor volumes started to decrease 7-10 days after immunization and they had reached volumes of 200-500 mm3. Furthermore, non-immunized mice died 2-3 days after such a tumor volume was reached. 6/9 mice vaccinated with the minimal epitope died of their tumor, whereas 8/10 mice vaccinated with the long peptide completely eradicated their tumor.
Figure 14B:
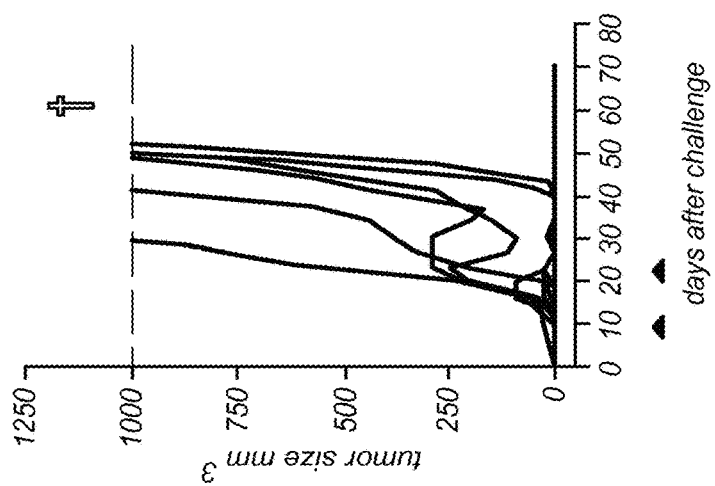
Figure 14A:
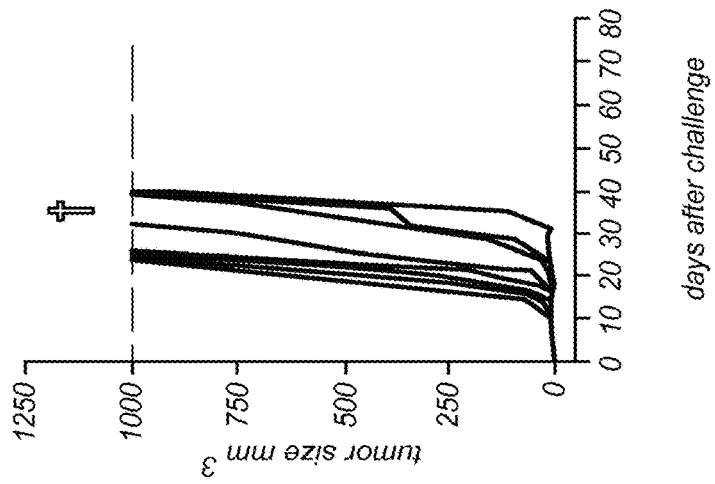
Figure 15A:
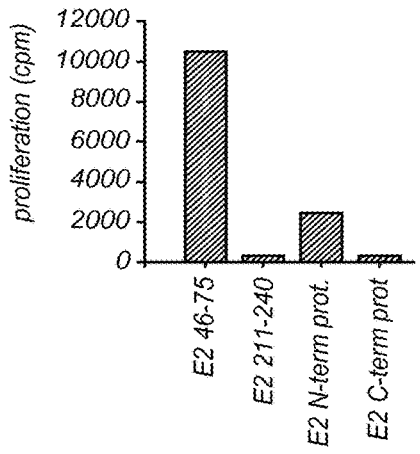
FIGS. 15a-15c. depict the proliferation of human CD4+ T-helper clones stimulated with peptide E2$_{46-75}$ that recognizes naturally processed Ag. PBMC from a healthy HLA DR4 positive blood donor were stimulated four times with peptides E2$_{46-75}$.
Figure 15B:
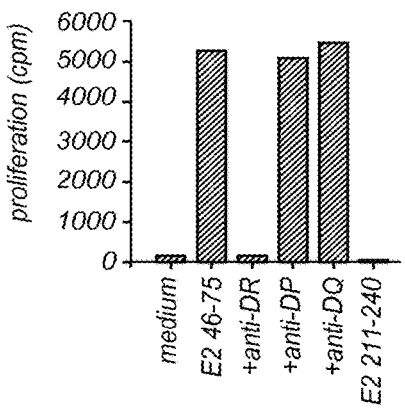
Figure 15C:
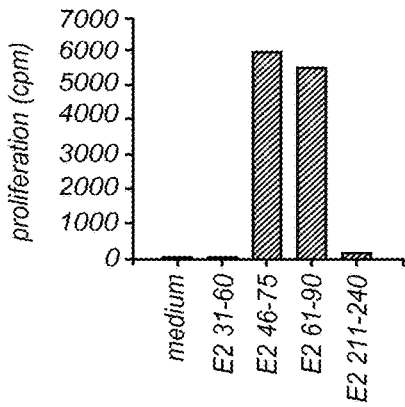
Figure 16A:
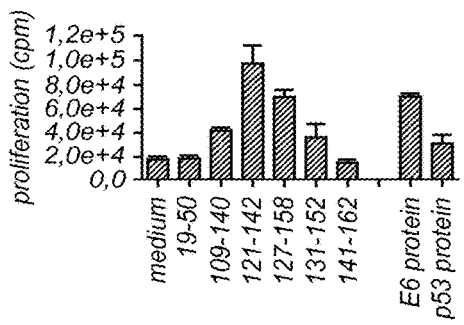
FIGS. 16a-16d depict a peptide E6$_{127-158}$ induced T-cell response that recognizes naturally processed Ag. PBMC from a healthy HLA-DR1 positive blood donor were stimulated four times with peptide E6$_{127-158}$.
Figure 16B:
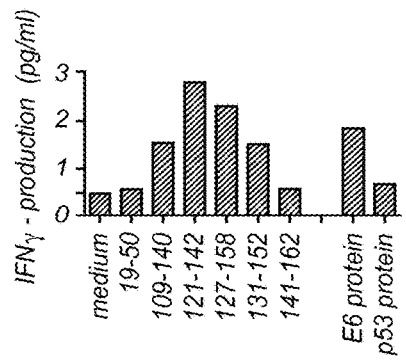
Figure 16C:
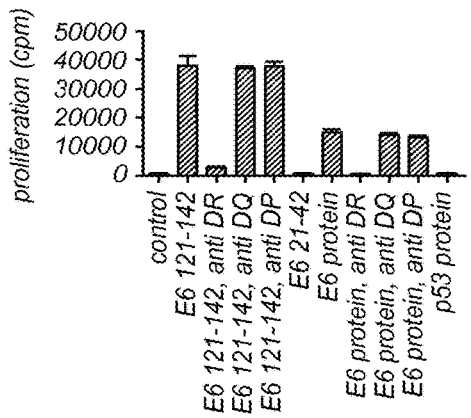
Figure 16D:
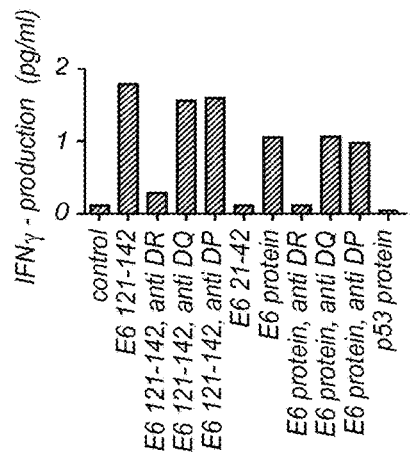

Altschul, S. F., Madden, T. L., Schaffer, A. A., Zhang, J., Zhang, Z., Miller, W., and Lipman, D. J., Gapped BLAST and PSI-BLAST: a new generation of protein database search programs. Nucleic Acids Res, 25,3389-402 (1997).

BARRASSO, R., DE BRUX, J., CROISSANT, O. AND ORTH, G., High prevalence of papillomavirus-associated penile intraepithelial neoplasia in sexual partners of women with cervical intraepithelial neoplasia. N. Engl. J. Med., 317,916-23 (1987).

BAUR, M. P., NEUGEBAUER, M. AND DEPPE, H., Population analysis on the basis of deduced haplotypes from random families. In : E. D. Albert, M. P. Baur and W. R. Mayr (eds.), Histocompatibility Testing, pp. 333-341, Springer-Verlag, Berlin (1984).

Bermas, B. L. and Hill, J. A., Proliferative responses to recall antigens are associated with pregnancy outcome in woman with a history of recurrent spontaneous abortion. J Clin Invest, 100,1330-4. (1997).

Borysiewicz, L. K., Fiander, A., Nimako, M., Man, S., Wilkinson, G. W. G., Westmoreland, D., Evans, A. S., Adams, M., Stacey, S. N., Boursnell, M. E. G., Rutherford, E., Hickling, E. and Inglis, S. C., A recombinant vaccina virus encoding human papillomavirus types 16 and 18, E6 and E7 proteins as immunotherapy for cervical cancer. Lancet, 347,1523 1527 (1996).

BOSCH, F. X., MANOS, M. M., MUNOZ, N., SHERMAN, M., JANSEN, A. M., PETO, J., SCHIFFMAN, M. H., MORENO, V., KURMAN, R. AND SHAH, K. V., Prevalence of human papillomavirus in cervical cancer: a worldwide perspective. International biological study on cervical cancer (IBSCC) Study Group. J Natl Cancer Inst, 87,796-802 (1995).

BRISTOL, J. A., C. ORSINI, P. LINDINGER, J. THALHAMER, AND S. 1. ABRAMS. 2000. Identification of a ras oncogene peptide that contains both CD4 (+) and CD8 (+) T cell epitopes in a nested configuration and elicits both T cell subset responses by peptide or DNA immunization. *Cell Immunol* 205:73.

CLAAS, E. C., MELCHERS, W. J., VAN DER LINDEN, H. C., LINDEMAN, J. AND QUINT, W. G., Human papillomavirus detection in paraffin-embedded cervical carcinomas and metastases of the carcinomas by the polymerase chain reaction. Am J Pathol, 135,703-9 (1989).

Clerici, M., Merola, M., Ferrario, E., Trabattoni, D., Villa, M. L., Stefanon, B., Venzon, D. J., Shearer, G. M., De Palo, G. and Clerici, E., Cytokine production patterns in cervical intraepithelial neoplasia: association with human papillomavirus infection. J. Natl. Cancer Inst., 89,245-250 (1997).

Coleman, N., Birley, H. D., Renton, A. M., Hanna, N. F., Ryait, B. K., Byrne, M., Taylor Robinson, D. and Stanley, M. A., Immunological events in regressing genital warts. Am. J. Clin. Pathol., 102,768-74 (1994).

DAS, S. N., KHANNA, N. N. AND KHANNA, S., A multiparametric observation of immune competence in breast cancer and its correlation with tumour load and prognosis. Ann Acad Med Singapore, 14,374-81 (1985).

DE BRUIJN, M. L., SCHUURHUIS, D. H., VIERBOOM, M. P., VERMEULEN, H., DE COCK, K. A., ODMS, M. E., RESSING, M. E., TOEBES, M., FRANKEN, K. L., DRIJFHOUT, J. W., OTTENHOFF, T. H., OFFRINGA, R. AND MELIEF, C. J., Immunization with human papillomavirus type 16 (HPV16) oncoprotein-loaded dendritic cells as well as protein in adjuvant induces MHC class I-restricted protection to HPV16-induced tumor cells. Cancer Res., 58, 724-731 (1998).

DE GRUIJL, T., BONTKES, H. J., WALBOOMERS, J. M. M., STUKART, M. J., DOEKHIE, F. S., REMMINK, A. J., HELMERHORST, T. J. M., VERHEIJEN, R. H. M., DUGGAN-KEEN, M. F., STERN, P. L., MEIJER, C. J. L. M. AND SCHEPER, R. J., Differential T-helper cell responses to human papillomavirus type 16 E7 related to viral clearance or persistence in patients with cervical neoplasia: A longitudinal study. Cancer Res., 58, 1700-1706 (1998).

DYSON N, HOWLEY P M, MUNGER K, HARLOW E: The human papilloma virus-16 E7 oncoprotein is able to bind to the retinoblastoma gene product. Science 243 (4893): 934, 1989.

Ho G Y, BURK R D, FLEMING I, KLEIN R S: Risk of genital human papillomavirus infection in women with human immunodeficiency virus-induced immunosuppression. Int J Cancer 56 (6): 788, 1994

EARLY, E. AND REEN, D. J., Rapid conversion of naive to effector T cell function counteracts diminished primary human newborn T cell responses. Clin. Exp. Immunol., 116,527-33 (1999).

EVANS, E. M., MAN, S., EVANS, A. S. AND BORYSIEWICZ, L. K., Infiltration of cervical cancer tissue with human papillomavirus-specific cytotoxic T-lymphocytes. Cancer Res., 57,2943-2950 (1997).

FELTKAMP M C, SMITS H L, VIERBOOM M P, MINNAAR R P, DE JONGH B M, DRIJFHOUT J W, TER SCHEGGET J, MELIEF C J, KAST W M: Vaccination with cytotoxic T lymphocyte epitope-containing peptide protects against a tumor induced by human papillomavirus type 16-transformed cells. Eur J Immunol 23 (9): 2242,1993

Franken, K. L., Hiemstra, H. S., van Meijgaarden, K. E., Subronto, Y., den Hartigh, J., Ottenhoff, T. H. and Drijfhout, J. W., Purification of his-tagged proteins by immobilized chelate affinity chromatography: the benefits from the use of organic solvent. Protein *Expr Purif,* 18,95-9 (2000).

Fu T M, Guan L, Friedman A, Schofield T L, Ulmer J B, Liu M A, et al., Dose dependence of CTL precursor frequency induced by a DNA vaccine and correlation with protective immunity against influenza virus challenge. J Immunol 1999; 162 (7): 4163-4170.

Geluk, A., Taneja, V., Van Meijgaarden, K. E., Zanelli, E., Abou-Zeid, C., Thole, J. E., de Vries, R. R., David, C. S. and Ottenhoff, T. H., Identification of HLA class 11-restricted determinants of *Mycobacterium tuberculosis*-derived proteins by using HLA-transgenic, class II-deficient mice. Proc. Natl. Acad. Sci. U.S.A., 95,10797-10802 (1998).

GELUK, A., VAN MEIJGAARDEN, K. E., DRIJFHOUT, J. W. AND OTTENHOFF, T. H., Clip binds to HLA class II using methionine-based, allele-dependent motifs as well as alleleindependent supermotifs. Mol. Immunol., 32, 975 981 (1995).

GHOSH, P., KOMSCHLIES, K. L., CIPPITELLI, M., LONGO, D. L., SUBLESKI, J., YE, J., SICA, A., YOUNG, H. A., WILTROUT, R. H. AND OCHOA, A. C., Gradual loss of T-helper 1 populations in spleen of mice during progressive tumor growth. J Natl Cancer Inst, 87, 1478-83 (1995).

HALPERT R, FRUCHTER R G, SEDLIS A, BUTT K, BOYCE J G, SILLMAN F H : Human papillomavirus and lower genital neoplasia in renal transplant patients. Obstet Gynecol 68 (2): 251,1986

HAN R, CLADEL N M, REED C A, PENG X, CHRISTENSEN N D : Protection of rabbits from viral challenge by gene gun-based intracutaneous vaccination with a combination of cottontail rabbit papillomavirus E1, E2, E6, and E7 genes. J Virol 73 (8): 7039,1999.

HIRANUMA, K., S. TAMAKI, Y. NISHIMURA, S. KUSUKI, M. ISOGAWA, G. Mm, M. KAITO, K. KURIBAYASHI, Y. ADACHI, AND Y. YASUTOMI. 1999. Helper T cell determinant peptide contributes to induction of cellular immune responses by peptide vaccines against hepatitis C virus. J Gen Virol 80:187.

Ho GY, Bierman R, BEARDSLEY L, CHANG C J, BURK RD : Natural history of cervicovaginal papillomavirus infection in young women. N Engl J Med 338 (7): 423, 1998.

HOHN, H., PILCH, H., GUNZEL, S., NEUKIRCH, C., HILMES, C., KAUFMANN, A., SELIGER, B. AND MAURER, M. J., CD4+ tumor-infiltrating lymphocytes in cervical cancer recognize HLA-DR-restricted peptides provided by human papillomavirus-E7. J Immunol., 163, 5715-22 (1999).

HOPFL, R., WIDSCHWENDTER, A., CHRISTENSEN, N. D., WIELAND, U., ZUMBACH, K., SANDRA, H., PFISTER, H. J., PAWLITA, M. AND HEIM, K., Delayed-type hypersenstivity to HPV16 E7 and humoral immunity to HPV16/18 E6, E7 and HPV 6/11/16/18/31 L1-virus like particles in women with cervical neoplasia. In : X. Castellsague, F. X. Bosch, S. de Sanjose, V. Moreno and J. Ribes (eds.), 18th international papillomavirus conference, pp.299, Institut Catale d'Oncologia, Barcelona, Spain (2000).

JONDAL M, SCHIRMBECK R, REIMANN J : MHC class I-restricted CTL responses to exogenous antigens. Immunity 5 (4): 295,1996

Karlsson, R., Jonsson, M., Edlund, K., Evander, M., Gustaysson, A., Boden, E., Rylander, E. and Wadell, G., Lifetime number of partners as the only independent risk factor for human papillomavirus infection: a population-based study. Sex Transm Dis, 22,119-27 (1995).

KAST W M, ROUXL, CURRENJ, BLOMHJ, VOORDOUWAC, MELOENRH, KOLAEOFSKYD, MELIEF C J: Protection against lethal Sendai virus infection by in vivo priming of virusspecific cytotoxic T lymphocytes with a free synthetic peptide. Proc. Natl. Acad. Sci. U.S.A.88 (6): 2283,1991

KOUTSKY L: Epidemiology of genital human papillomavirus infection. Am J Med 102 (5A): 3,1997.

KURTS C, CARBONE F R, BARNDENM, BLANAS E, ALLISON J, HEATH W R, MILLER J F: CD4+ T cell help impairs CD8+ T cell deletion induced by crosspresentation of self antigens and favors autoimmunity. J Exp Med 186 (12): 2057,1997

Manca, F., Li Pira, G., Fenoglio, D., Fang, S. P., Habeshaw, A., Knight, S. C. and Dalgleish, A. G., Dendritic cells are potent antigen-presenting cells for in vitro induction of primary human CD4+ T-cell lines specific for HIV gp 120. J Acquir Immune Defic Syndr, 7,15-23 (1994).

MARRAZZO J M, STINE K, KOUTSKY L A : Genital human papillomavirus infection in women who have sex with women: a review. Am J Obstet Gynecol 183 (3): 770,2000

MATORRAS R, ARICETA J M, REMENTERIA A, CORRAL J, GUTIERREZ DE TERAN G, DIEZ J, MONTOYA F, RODRIGUEZ-ESCUDERO F J: Human immunodeficiency virus-induced immunosuppression: a risk factor for human papillomavirus infection. Am J Obstet Gynecol 164 (1 Pt 1): 42,1991

McCutcheon, M., Wehner, N., Wensky, A., Kushner, M, Doan, S., Hisao, L., Calabresi, P., Ha, T., Tran, T. V., Tate, K. M., Winkelhake, J. and Spack, E. G., A sensitive ELISPOT assay to detect low-frequency human T lymphocytes. J Immunol Methods, 210,149-66 (1997).

MELIEF, C. J. M., TOES, R. E. M., MEDEMA, J. P., VAN DER BURG, S. H., OSSENDORP, F. AND OFFRINGA, R., Strategies for Immunotherapy of Cancer. Adv. Immunol., 75,235-281 (2000).

Mellman, I., Turley, S. J. and Steinman, R. M., Antigen processing for amateurs and professionals. Trends Cell Biol, 8, 231-7 (1998).

NAIPAL, A. M., D'AMARO, J., RUNING, J. W., VANLEEUWEN, A. AND VAN ROOD, J. J., Automated reading of Propidium Iodide lymphocytotoxicity tests for HLA-DR, MB, MT typing. Tissue Antigens, 24,302-6 (1984).

NIMAKO, M., FINDER, A., WILKINSON, G. W. G., BORYSIEWICZ, L. K. AND MAN, S., Human papillomavirus-specific cytotoxic T lymphocytes in patients with cervical intraepithelial neoplasia grade III. Cancer Res., 57,4855-4861 (1997).

OSSENDORP F, MENGEDE E, CAMPS M, FILIUS R, MELIEF C J M: Specific T helper cell requirement for optimal induction of cytotoxic T lymphocytes against major histocompatibility complex class Il negative tumors. J. Exp. Med. 187 (5): 1, 1998.

PARDOLL, D. M. AND TOPALIAN, S. L., The role of CD4+ T cell responses in antitumor immunity. Curr. Opin. Immunol., 10,588-94 (1998).

Pittet, M. J., Valmori, D., Dunbar, P. R., Speiser, D. E., Lienard, D., Lejeune, F., Fleischhauer, K., Cerundolo, V., Cerottini, J. C. and Romero, P., High frequencies of naive Melan-A/MART-1-specific CD8 (+) T cells in a large proportion of human histocompatibility leukocyte antigen (HLA)-A2 individuals. J. Exp. Med., 190,705-15 (1999).

RAIVIMENSEE, H. G., FRIEDE, T. AND STEVANOVIIC, S., MEW ligands and peptide motifs: first listing. Immunogenetics, 41,178-228 (1995).

REIMANN J, KAUFMANN S H: Alternative antigen processing pathways in anti-infective immunity. Curr Opin Immunol 9 (4): 462,1997

RESSING, M. E., SETTE, A., BRANDT, R. M. P., RUPPERT, J., WENTWORTH, P. A., HARTMAN, M., OSEROFF, C., GREY, H. M., MELIEF, C. J. M. AND KAST, W. M., Human CTL epitopes encoded by human papillomavirus type 16 E6 and E7 identified through in vivo and in vitro immunogenicity studies of HLA-A*0201 binding peptides. J. Immunol., 154,59345943 (1995).

RESSING, M. E., VAN DRIEL, W. J., BRANDT, R. M., KENTER, G. G., DE JONG, J. H., BAUKNECHT, T., FLEUREN, G. J., HOOGERHOUT, P., OFFRINGA, R., SETTE, A., CELIS, E., GREY, H., TRIMBOS, B. J., KAST, W. M. AND MELIEF, C. J., Detection of T helper responses, but not of human papillomavirus-specific cytotoxic T lymphocyte responses, after peptide vaccination of patients with cervical carcinoma. J. Immunother., 23,25566 (2000).

RESSING, M. E., VANDRIEL, W. J., CELIS, E., SETTE, A., BRANDT, R. M. P., HARTMAN, M., ANHOLTS, J. D. H., SCHREUDER, G. M. T., TER HARMSEL, W. B., FLEURE, G. J., TRIMBOS, B. J., KAST, W. M. AND

MELIEF, C. J. M., Occasional memory cytotoxic T-cell responses of patients with human papillomavirus type 16-positive cervical lesions against a human leukocyte antigen-A*0201-restricted E7-encoded epitope. Cancer Res., 56,582-588 (1996).

Rodriguez, A., Regnault, A., Kleijmeer, M., Ricciardi-Castagnoli, P. and Amigorena, S., Selective transport of internalized antigens to the cytosol for MHC class I presentation in dendritic cells. Nat Cell Biol, 1, 362-8 (1999).

SCHEFFNER M, WERNESS B A, HUIBREGTSE J M, LEVINE A J, HOWLEY P M: The E6 oncoprotein encoded by human papillomavirus types 16 and 18 promotes the degradation of p53. Cell 63 (6): 1129,1990.

SCHOENBERGER S P, TOES R E, VAN DER VOORT E I, OFFRINGA R, MELIEF C J: T-cell help for cytotoxic T lymphocytes is mediated by CD40-CD40L interactions. Nature 393 (6684): 480,1998.

Sedlik C, Dadaglio G, Saron M F, Deriaud E, Rojas M, Casal SI, et al., In vivo induction of a high-avidity, high-frequency cytotoxic T-lymphocyte response is associated with antiviral protective immunity. J Virol 2000; 74 (13) : 5769-5775.

SELVAKUMAR R, BORENSTEIN L A, LIN Y L, AHMED R, WETTSTEIN F O: Immunization with non-structural proteins E1 and E2 of cottontail rabbit papillomavirus stimulates regression of virus-induced papillomas. J Virol 69 (1) : 602,1995.

SHIRAI, M., C. D. PENDLETON, J. AHLERS, T. TAKESHITA, M. NEWMAN, AND J. A. BERZOFSKY. 1994. Helper-cytotoxic T lymphocyte (CTL) determinant linkage required for priming of anti-HIV CD8+ CTL in vivo with peptide vaccine constructs. *J Immunol* 152:549.

Thomas, K. K., Hughes, J. P., Kuypers, J. M., Kiviat, N. B., Lee, S. K., Adam, D. E. and Koutsky, L. A., Concurrent and sequential acquisition of different genital human papillomavirus types [In Process Citation]. *J Infect Dis,* 182,1097-102 (2000).

TOES R E, OFFRINGA R, BLOM R J, MELIEF C J, KAST W M: Peptide vaccination can lead to enhanced tumor growth through specific T-cell tolerance induction. Proc Natl Acad Sci USA 93 (15): 7855, 1996a.

TOES R E, BLOM R J, OFFRINGA R, KAST W M, MELIEF C J: Enhanced tumor outgrowth after peptide vaccination. Functional deletion of tumor-specific CTL induced by peptide vaccination can lead to the inability to reject tumors. J Immunol 156 (10): 3911,1996b TOES, R. E. M., OSSENDORP, F., OFFRINGA, R. AND MELIEF, C. J. M., CD4 T cells and their role in antitumor immune responses. J. Exp. Med., 189,753-756 (1999).

VAN DER BURG, S. H., KWAPPENBERG, K. M., GELUK, A., VANDER KRUK, M., PONTESILLI, O., HOVENKAMP, E., FRANKEN, K. L., VANMEIJGAARDEN, K. E., DRIJFHOUT, J. W., OTTENHOFF, T. H., MELIEF, C. J. AND OFFRINGA, R., Identification of a conserved universal Th epitope in HIV-1 reverse transcriptase that is processed and presented to HIV-specific CD4+ T cells by at least four unrelated HLA-DR molecules. J. Immunol., 162,152-60 (1999).

VAN DER BURG, S. H., K. M. C. KWAPPENBERG, T. O'NEILL, R. M. P. BRANDT, C. J. M. MELIEF, J. K. HICKLING, R. OFFRINGA (2001): Pre-clinical safety and efficacy of TA-CIN, a recombinant HPV16 L2E6E7 fusion protein vaccine, in homologous and heterologous prime-boost regimens. Vaccine, 19: 3652-3660

WANEBO, H. J., JUN, M. Y., STRONG, E. W. AND OETTGEN, H., T-cell deficiency in patients with squamous cell cancer of the head and neck. Am J Surg, 130,445-51 (1975).

ZUR HAUSEN H: Papillomavirus infections-a major cause of human cancers. Biochimica et Biophysica Acta 1288: F55,1996.

---

The invention claimed is:

1. An immunogenic pharmaceutical composition comprising a peptide of 32 to 45 contiguous amino acids of E7 protein of type 16 human papilloma virus (HPV) as a subunit, comprising a T helper cell epitope consisting of residues 35-50 of the HPV type 16 E7 protein and an immune-stimulating amount of a pharmaceutically acceptable adjuvant.

2. The immunogenic composition of claim 1, wherein the peptide has a length of 32-40 amino acids.

3. The immunogenic composition of claim 1, wherein the peptide has a length of 32-35 amino acids.

4. The immunogenic composition of claim 1, wherein the peptide consists of residues 22-56 of HPV 16 E7.

5. The immunogenic composition of claim 1, further comprising a peptide comprising residues 46-75, 51-70, 61-76, 311-325, 316-330, 346-355 or 351-365 of HPV16 E2.

6. The immunogenic composition of claim 1, further comprising a peptide comprising residues 50-62 or 43-77 of HPV 16 E7.

7. The immunogenic composition of claim 1, further comprising a peptide comprising residues 121-142 or 127-140 of HPV 16 E6.

8. The immunogenic composition of claim 1, wherein the adjuvant is selected from the group consisting of
(a) an exosome,
(b) poly I:C,
(c) poly I:poly C12U,
(d) monophosphoryl lipid A,
(e) a CpG-containing nucleic acid,
(f) a CD40 ligand, and
(g) a mixture of any of (a)-(f).

9. The immunogenic composition of claim 8, wherein the CD40 ligand is an anti-CD40 antibody.

* * * * *

SEQUENCE LISTING

```
<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: minimal E1A-derived CTL epitope

<400> SEQUENCE: 1

Ser Gly Pro Ser Asn Thr Pro Pro Glu Ile
1               5                   10

<210> SEQ ID NO 2
<211> LENGTH: 33
<212> TYPE: PRT
<213> ORGANISM: Artificial Sequence
<220> FEATURE:
<223> OTHER INFORMATION: minimal CTL epitope of adenovirus E1A protein

<400> SEQUENCE: 2

Arg Glu Cys Asn Ser Ser Thr Asp Ser Cys Asp Ser Gly Pro Ser Asn
1               5                   10                  15

Thr Pro Pro Glu Ile His Pro Val Val Arg Leu Cys Pro Ile Ile Lys
            20                  25                  30

Pro
```

```
<210> SEQ ID NO 3
<211> LENGTH: 9
<212> TYPE: PRT
<213> ORGANISM: Artificial Sequence
<220> FEATURE:
<223> OTHER INFORMATION: minimal 9 amino acid long CTL epitope

<400> SEQUENCE: 3

Arg Ala His Tyr Asn Ile Val Thr Phe
1               5

<210> SEQ ID NO 4
<211> LENGTH: 13
<212> TYPE: PRT
<213> ORGANISM: Artificial Sequence
<220> FEATURE:
<223> OTHER INFORMATION: HA 308-319

<400> SEQUENCE: 4

Pro Lys Tyr Val Lys Gln Asn Thr Leu Lys Leu Ala Thr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: hsp65 3-13

<400> SEQUENCE: 5

Lys Thr Ile Ala Tyr Asp Glu Glu Ala Arg Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: HA 308-319

<400> SEQUENCE: 6

Pro Lys Phe Val Lys Gln Asn Thr Lys Leu Ala Thr
1               5                   10

<210> SEQ ID NO 7
<211> LENGTH: 24
<212> TYPE: PRT
<213> ORGANISM: Artificial Sequence
<220> FEATURE:
<223> OTHER INFORMATION: Ii 80-103

<400> SEQUENCE: 7

Leu Pro Lys Pro Pro Lys Pro Val Ser Lys Met Arg Met Ala Thr Pro
1               5                   10                  15

Leu Leu Met Gln Ala Leu Pro Met
            20

<210> SEQ ID NO 8
<211> LENGTH: 30
<212> TYPE: PRT
<213> ORGANISM: Artificial Sequence
<220> FEATURE:
<223> OTHER INFORMATION: HPV16-E2 derived peptide

<400> SEQUENCE: 8

Phe Asn Ser Ser His Lys Gly Arg Ile Asn Cys Asn Ser Asn Thr Thr
1               5                   10                  15
```

```
Pro Ile Val His Leu Lys Gly Asp Ala Asn Thr Leu Lys Cys
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: HPV16-E2 derived peptide

<400> SEQUENCE: 9

Thr Pro Ile Val His Leu Lys Gly Asp Ala Asn Thr Leu Lys Cys Leu
1               5                   10                  15

Arg Tyr Arg Phe Lys Lys His Cys Thr Leu Tyr Thr Ala Val
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: HPV16-E2 derived peptide

<400> SEQUENCE: 10

Leu Arg Tyr Arg Phe Lys Lys His Cys Thr Leu Tyr Thr Ala Val Ser
1               5                   10                  15

Ser Thr Trp His Trp Thr Gly His Asn Val Lys His Lys Ser
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: HPV16-E2 derived peptide

<400> SEQUENCE: 11

Ser Ser Thr Trp His Trp Thr Gly His Asn Val Lys His Lys Ser Ala
1               5                   10                  15

Ile Val Thr Leu Thr Tyr Asp Ser Glu Trp Gln Arg Asp Gln
            20                  25                  30

<210> SEQ ID NO 12
<211> LENGTH: 35
<212> TYPE: PRT
<213> ORGANISM: Artificial Sequence
<220> FEATURE:
<223> OTHER INFORMATION: HPV16-E2 derived peptide

<400> SEQUENCE: 12

Ala Ile Val Thr Leu Thr Tyr Asp Ser Glu Trp Gln Arg Asp Gln Phe
1               5                   10                  15

Leu Ser Gln Val Lys Ile Pro Lys Thr Ile Thr Val Ser Thr Gly Phe
            20                  25                  30

Met Ser Ile
        35

<210> SEQ ID NO 13
<211> LENGTH: 32
<212> TYPE: PRT
<213> ORGANISM: Artificial Sequence
<220> FEATURE:
<223> OTHER INFORMATION: minimal CTL epitope of adenovirus E1A protein
```

```
<400> SEQUENCE: 13

Arg Glu Cys Asn Ser Ser Thr Asp Ser Cys Asp Ser Gly Pro Ser Asn
1               5                   10                  15

Thr Pro Pro Glu Ile His Pro Val Val Arg Leu Cys Pro Ile Lys Pro
            20                  25                  30

<210> SEQ ID NO 14
<211> LENGTH: 34
<212> TYPE: PRT
<213> ORGANISM: Artificial Sequence
<220> FEATURE:
<223> OTHER INFORMATION: HPV16-E7 derived peptides

<400> SEQUENCE: 14

Gly Gln Ala Glu Pro Asp Arg Ala His Asn Ile Val Thr Phe Cys Cys
1               5                   10                  15

Lys Cys Asp Ser Thr Leu Arg Leu Cys Val Gln Ser Thr His Val Asp
            20                  25                  30

Ile Arg
```